(12) United States Patent
Beavis et al.

(10) Patent No.: US 12,202,855 B2
(45) Date of Patent: Jan. 21, 2025

(54) MODIFIED T CELLS AND USES THEREOF

(71) Applicant: PETER MACCALLUM CANCER INSTITUTE, Melbourne (AU)

(72) Inventors: Paul Beavis, Reservoir (AU); Philip Darcy, Yallambie (AU)

(73) Assignee: Peter MacCallum Cancer Institute, Melbourne (AU)

( * ) Notice: Subject to any disclaimer, the term of this patent is extended or adjusted under 35 U.S.C. 154(b) by 884 days.

(21) Appl. No.: 17/255,201

(22) PCT Filed: Jun. 25, 2019

(86) PCT No.: PCT/AU2019/050660
§ 371 (c)(1),
(2) Date: Dec. 22, 2020

(87) PCT Pub. No.: WO2020/000035
PCT Pub. Date: Jan. 2, 2020

(65) Prior Publication Data
US 2021/0379107 A1    Dec. 9, 2021

(30) Foreign Application Priority Data
Jun. 25, 2018 (AU) ................................ 2018902260

(51) Int. Cl.
| | | |
|---|---|---|
| *A61K 35/17* | (2015.01) | |
| *A61K 39/00* | (2006.01) | |
| *A61K 45/06* | (2006.01) | |
| *A61P 35/00* | (2006.01) | |
| *C07K 14/52* | (2006.01) | |
| *C07K 14/705* | (2006.01) | |
| *C07K 14/725* | (2006.01) | |
| *C07K 16/32* | (2006.01) | |
| *C12N 5/0783* | (2010.01) | |
| *C12N 15/85* | (2006.01) | |

(52) U.S. Cl.
CPC .......... *A61K 45/06* (2013.01); *A61K 39/4611* (2023.05); *A61K 39/4631* (2023.05); *A61K 39/4644* (2023.05); *A61K 39/464406* (2023.05); *A61K 39/464416* (2023.05); *A61P 35/00* (2018.01); *C07K 14/52* (2013.01); *C07K 14/7051* (2013.01); *C07K 14/70521* (2013.01); *C07K 16/32* (2013.01); *C12N 5/0636* (2013.01); *C12N 5/0638* (2013.01); *C12N 15/85* (2013.01); *A61K 2239/38* (2023.05); *A61K 2239/49* (2023.05); *A61K 2239/50* (2023.05); *C07K 2319/02* (2013.01)

(58) Field of Classification Search
CPC . C12N 5/0636; C07K 14/70532; A61K 35/17
See application file for complete search history.

(56) References Cited

FOREIGN PATENT DOCUMENTS

| | | | |
|---|---|---|---|
| CN | 111849913 B * | 5/2021 | ......... A61K 38/1709 |
| WO | WO 2016/049641 | 3/2016 | |
| WO | WO-2018038945 A1 * | 3/2018 | ............. A61K 35/12 |

OTHER PUBLICATIONS

An et al. "Construction of a new anti-CD19 chimeric antigen receptor and the anti-leukemia function study of the transduced T cells" Oncotarget, vol. 7, No. 9, 10638-10649, 2016 (Year: 2016).*
Wang et al. "Targeting FLT3 in acute myeloid leukemia using ligand-based chimeric antigen receptor-engineered T cells" Journal of Hematology & Oncology (2018) 11:60, 12 pages (Year: 2018).*
Yong et al. "CAR T-cell therapy of solid tumors" Immunology and Cell Biology, 95, 356-363, 2017 (Year: 2017).*
Merriam-Wbster Medical Definition "secrete" 1 page, last updated Sep. 7, 2024 (Year: 2024).*
NCI Dictionary of Cancer Terms "secrete" 1 page, accessed Sep. 4, 2024 (Year: 2024).*
Lai et al. "Adoptive cellular therapy with T cells expressing the dendritic cell growth factor Flt3L drives epitope spreading and antitumor immunity" Nature Immunology | vol. 21 | 914 Aug. 2020 | 914-926 | (Year: 2020).*
CN111849913B—English Translation, 34 pages, accessed Sep. 4, 2024 (Year: 2024).*
Boshart et al., "A very strong enhancer is located upstream of an immediate early gene of human cytomegalovirus", Cell, vol. 41:521-530 (1985).
Bøyum, "Isolation of mononuclear cells and granulocytes from human blood", Scandinavian Journal of Clinical Laboratory Investigation, vol. 21 (Suppl. 97, Paper IV): 77-89 (1968).
Desch et al., "Dendritic cell subsets require cis-activation for cytotoxic CD8 T-cell induction", Nature Communications, vol. 5:1-13 (2014).
Dijkema et al., "Cloning and expression of the chromosomal immune interferon gene of the rat", The EMBO Journal vol. 4(3):761-767, (1985).
Gorman et al., "The Rous sarcoma virus long terminal repeat is a strong promoter when introduced into a variety of eukaryotic cells by DNA-mediated transfection", Proceedings of the National Academy of Science. USA, vol. 79:6777-6781, (1982).
Jelinek et al. , "TLR3-Specific double-stranded RNA Oligonucleotide adjuvants induce dendritic cell cross-presentation, CTL responses, and antiviral protection", Journal of Immunology, vol. 186:2422-2429 (2011).
John et al., "Anti-PD-1 antibody therapy potently enhances the eradication of established tumors by gene-modified T cells", Clinical Cancer Research, vol. 19:5636-5646 (2013).

(Continued)

*Primary Examiner* — Thane Underdahl
(74) *Attorney, Agent, or Firm* — Knobbe, Martens Olson & Bear, LLP

(57) ABSTRACT

The present invention generally relates to T cells that are modified to enhance the efficiency of adoptive cellular therapy by modulating dendritic cell activity, a composition comprising modified T cells, vectors and methods for the treatment of cancer comprising administering modified T cells. In particular, the present invention provides modified T cells for use in adoptive cellular therapies for the treatment of solid tumours.

9 Claims, 54 Drawing Sheets
Specification includes a Sequence Listing.

(56) References Cited

OTHER PUBLICATIONS

Kalos et al., "T Cells with chimeric antigen receptors have potent antitumor effects and can establish memory in patients with advanced ldukemia", Science Translational Medicine, vol. 3(95):95ra73, pp. 1-11 (2011).

Mardiana et al., "A multifunctional role for adjuvant anti-4-1BB therapy in augmenting antitumor response by chimeric antigen receptor T cells", Microenvironment and Immunology, Cancer Research, American Assoc. for Cancer Research, vol. 77(6): 1296-1309, Abstract of a thesis <URL:http://hdl.handle.net/11343/219339>, published online Jan. 12, 2017.

Maude et al., "Chimeric antigen receptor T cells for sustained remissions in leukemia", The New England Journal of Medicine, 371(16):1507-17 (2014).

Mayer et al., "Selective and efficient generation of functional Batf3-dependent CD103+ dendritic cells from mouse bone marrow", Blood, 124(20):3081-3091 (2014).

Meixlsperger et al., "CD141+ dendritic cells produce prominent amounts of IFN-α after dsRNA recognition and can be targeted via DEC-205 in humanized mice", Blood, vol. 121(25):5034-44 (2013).

Oh et al., "TLR7 enables cross-presentation by multiple dendritic cell subsets through a tupe I IFN-dependent pathway", Blood, vol. 118(11):3028-3038 (2011).

Pulido et al., "TIM-3 regulates CD103+ dendritic cell function and response to chemotherapy in breast cancer", Cancer Cell, 33(1):60-74 (2018).

Ritchie et al., "Persistence and efficacy of second generation CAR T Cell against the LeY antigen in acute myeloid leukemia", Molecular Therapy, vol. 21(11):2122-2129 (2013).

Riediger et al., "Fms-like tyrosine kinase 3 receptor ligand (Flt3L)-based vaccination administered with an adenoviral vector prevents tumor growth of colorectal cancer in a BALB/c mouse model", J. of Cancer Research and Clinical Oncology, 139:2097-2110 (2013).

Rosenberg et al., "Use of tumor-infiltrating lymphocytes and interleukin-2 in the immunotherapy of patients with metastatic melanoma", New England Journal of Medicine, 319(25): 1676-1680 (1988).

Sade-Feldman et al., "Defining T cell states associated with response to checkpoint immunotherapy in melanoma", Cell, 175(4):998-1013 (2018).

Spranger et al., "Tumor-residing Batf3 dendritic cells are required for effector T cell trafficking and adoptive T cell therapy", Cancer Cell, 31:711-23 (2017).

Wang et al., "Targeting FLT3 in acute myeloid leukemia using ligand-based chimeric antigen receptor-engineered T cells", Journal of Hematology & Oncology, vol. 11(60):1-12 (2018).

Ward et al., "Binding activities of a repertoire of single immunoglobulin variable domains secreted from *Escherichia coli*", Letters to Nature, vol. 341:544-6 (1989).

Westwood et al., "The Lewis-Y carbohydrate antigen is expressed by many human tumors and can serve as a target for genetically redirected T cells despite the presence of soluble antigen in serum", Journal of Immunotherapy, vol. 32(3):292-301 (2009).

Yeku et al., "Armored CAR T-cells: utilizing cytokines and proinflammatory ligands to enhance CAR T-cell anti-tumour efficacy", Biochemical Society Transactions, 44(2):412-418 (2016).

\* cited by examiner

A

B

E

F

G

H

I

J

K

L

E

F

G

H

I

J

C

D

G

H

A

B

SEQUENCE LISTING

<160> NUMBER OF SEQ ID NOS: 3

<210> SEQ ID NO 1
<211> LENGTH: 7212
<212> TYPE: DNA
<213> ORGANISM: Homo sapiens

<400> SEQUENCE: 1

| | | | | | |
|---|---|---|---|---|---|
| taaagatacc | aggcgtttcc | ccctggaagc | tccctcgtgc | gctctcctgt | tccgaccctg | 60 |
| ccgcttaccg | gatacctgtc | cgcctttctc | ccttcgggaa | gcgtggcgct | ttctcatagc | 120 |
| tcacgctgta | ggtatctcag | ttcggtgtag | gtcgttcgct | ccaagctggg | ctgtgtgcac | 180 |
| gaacccccg | ttcagcccga | ccgctgcgcc | ttatccggta | actatcgtct | tgagtccaac | 240 |
| ccggtaagac | acgacttatc | gccactggca | gcagccactg | gtaacaggat | tagcagagcg | 300 |
| aggtatgtag | gcggtgctac | agagttcttg | aagtggtggc | ctaactacgg | ctacactaga | 360 |
| agaacagtat | ttggtatctg | cgctctgctg | aagccagtta | ccttcggaaa | aagagttggt | 420 |
| agctcttgat | ccggcaaaca | aaccaccgct | ggtagcggtg | gtttttttgt | ttgcaagcag | 480 |
| cagattacgc | gcagaaaaaa | aggatctcaa | gaagatcctt | tgatcttttc | tacgggtct | 540 |
| gacgctcagt | ggaacgaaaa | ctcacgttaa | gggattttgg | tcatgagatt | atcaaaaagg | 600 |
| atcttcacct | agatcctttt | aaattaaaaa | tgaagtttta | aatcaatcta | aagtatatat | 660 |
| gagtaaactt | ggtctgacag | ttaccaatgc | ttaatcagtg | aggcacctat | ctcagcgatc | 720 |
| tgtctatttc | gttcatccat | agttgcctga | ctccccgtcg | tgtagataac | tacgatacgg | 780 |
| gagggcttac | catctggccc | cagtgctgca | atgataccgc | gagacccacg | ctcaccggct | 840 |
| ccagatttat | cagcaataaa | ccagccagcc | ggaagggccg | agcgcagaag | tggtcctgca | 900 |
| actttatccg | cctccatcca | gtctattaat | tgttgccggg | aagctagagt | aagtagttcg | 960 |
| ccagttaata | gtttgcgcaa | cgttgttgcc | attgctacag | gcatcgtggt | gtcacgctcg | 1020 |
| tcgtttggta | tggcttcatt | cagctccggt | tcccaacgat | caaggcgagt | tacatgatcc | 1080 |
| cccatgttgt | gcaaaaaagc | ggttagctcc | ttcggtcctc | cgatcgttgt | cagaagtaag | 1140 |
| ttggccgcag | tgttatcact | catggttatg | gcagcactgc | ataattctct | tactgtcatg | 1200 |
| ccatccgtaa | gatgcttttc | tgtgactggt | gagtactcaa | ccaagtcatt | ctgagaatag | 1260 |
| tgtatgcggc | gaccgagttg | ctcttgcccg | gcgtcaatac | gggataatac | cgcgccacat | 1320 |
| agcagaactt | taaaagtgct | catcattgga | aaacgttctt | cggggcgaaa | actctcaagg | 1380 |
| atcttaccgc | tgttgagatc | cagttcgatg | taacccactc | gtgcacccaa | ctgatcttca | 1440 |
| gcatctttta | ctttcaccag | cgtttctggg | tgagcaaaaa | caggaaggca | aaatgccgca | 1500 |
| aaaaagggaa | taagggcgac | acggaaatgt | tgaatactca | tactcttcct | ttttcaatat | 1560 |
| tattgaagca | tttatcaggg | ttattgtctc | atgagcggat | acatatttga | atgtatttag | 1620 |
| aaaaataaac | aaataggggt | tccgcgcaca | tttccccgaa | aagtgccacc | tgacgtctaa | 1680 |
| gaaaccatta | ttatcatgac | attaacctat | aaaaataggc | gtatcacgag | gccctttcgt | 1740 |
| ctcgcgcgtt | tcggtgatga | cggtgaaaac | ctctgacaca | tgcagctccc | ggagacggtc | 1800 |
| acagcttgtc | tgtaagcgga | tgccgggagc | agacaagccc | gtcagggcgc | gtcagcgggt | 1860 |
| gttggcgggt | gtcggggctg | gcttaactat | gcggcatcag | agcagattgt | actgagagtg | 1920 |
| caccatatgc | ggtgtgaaat | accgcacaga | tgcgtaagga | gaaaataccg | catcaggcgc | 1980 |
| cattcgccat | tcaggctgcg | caactgttgg | gaagggcgat | cggtgcgggc | ctcttcgcta | 2040 |
| ttacgccagc | tggcgaaagg | gggatgtgct | gcaaggcgat | taagttgggt | aacgccaggg | 2100 |

```
ttttcccagt cacgacgttg taaaacgacg gcgcaaggaa tggtgcatgc aaggagatgg    2160
cgcccaacag tccccggcc acggggcctg ccaccatacc cacgccgaaa caagcgctca    2220
tgagcccgaa gtggcgagcc cgatcttccc catcggtgat gtcggcgata taggcgccag    2280
caaccgcacc tgtggcgccg gtgatgccgg ccacgatgcg tccggcgtag aggcgattag    2340
tccaatttgt taaagacagg atatcagtgg tccaggctct agttttgact caacaatatc    2400
accagctgaa gcctatagag tacgagccat agataaaata aaagatttta tttagtctcc    2460 agaaaaggg gggaatgaaa gaccccacct gtaggtttgg caagctagct taagtaacgc    2520
cattttgcaa ggcatggaaa atacataact gagaatagag aagttcagat caaggttagg    2580
aacagagaga cagcagaata tgggccaaac aggatatctg tggtaagcag ttcctgcccc    2640
ggctcagggc caagaacaga tggtcccag atgcggtccc gccctcagca gtttctagag    2700
aaccatcaga tgtttccagg gtgccccaag gacctgaaat gaccctgtgc cttatttgaa    2760
ctaaccaatc agttcgcttc tcgcttctgt tcgcgcgctt ctgctcccg agctcaataa    2820 aagagcccac aacccctcac tcggcgcgcc agtcctccga tagactgcgt cgcccgggta    2880
cccgtattcc caataaagcc tcttgctgtt tgcatccgaa tcgtggactc gctgatcctt    2940
gggagggtct cctcagattg attgactgcc cacctcgggg gtctttcatt tggaggttcc    3000
accgagattt ggagacccct gcccagggac caccgacccc ccgccggga ggtaagctgg    3060 ccagcggtcg tttcgtgtct gtctctgtct ttgtgcgtgt ttgtgccggc atctaatgtt    3120
tgcgcctgcg tctgtactag ttagctaact agctctgtat ctggcggacc cgtggtggaa    3180
ctgacgagtt ctgaacaccc ggccgcaacc ctgggagacg tcccagggac tttggggcc    3240 gtttttgtgg cccgacctga ggaagggagt cgatgtggaa tccgaccccg tcaggatatg    3300
tggttctggt aggagacgag aacctaaaac agttcccgcc tccgtctgaa ttttgctttc    3360
cggtttggaa ccgaagccgc gcgtcttgtc tgctgcagcg ctgcagcatc gttctgtgtt    3420
gtctctgtct gactgtgttt ctgtatttgt ctgaaaatta gggccagact gttaccactc    3480
ccttaagttt gaccttaggt cactggaaag atgtcgagcg gatcgctcac aaccagtcgg    3540
tagatgtcaa gaagagacgt tgggttacct tctgctctgc agaatggcca acctttaacg    3600
tcggatggcc gcgagacggc accttttaacc gagacctcat cacccaggtt aagatcaagg    3660
tcttttcacc tggcccgcat ggacacccag accaggtccc ctacatcgtg acctgggaag    3720
ccttggcttt tgaccccct ccctgggtca agccctttgt acaccctaag cctccgcctc    3780
ctcttcctcc atccgcccg tctctccccc ttgaacctcc tcgttcgacc ccgcctcgat    3840
cctcccttta tccagccctc actccttctc taggcgccgg aattagatct caccatgaca    3900
gtgctggcgc cagcctggag cccaaattcc tccctgttgc tgctgttgct gctgctgagt    3960
ccttgcctgc gggggacacc tgactgttac ttcagccaca gtcccatctc ctccaacttc    4020
aaagtgaagt ttagagagtt gactgaccac ctgcttaaag attacccagt cactgtggcc    4080
gtcaatcttc aggacgagaa gcactgcaag gccttgtgga gcctcttcct agcccagcgc    4140
tggatagagc aactgaagac tgtggcaggg tctaagatgc aaacgcttct ggaggacgtc    4200
aacaccgaga tacattttgt cacctcatgt accttccagc cctaccagaa atgtctgcga    4260
ttcgtccaga ccaacatctc ccacctcctg aaggacacct gcacacagct gcttgctctg    4320
aagccctgta tcgggaaggc ctgccagaat ttctctcggt gcctgaggt gcagtgccag    4380 ccggactcct ccaccctgct gcccccaagg agtcccatag ccctagaagc cacggagctc    4440
```

```
ccagagcctc ggcccaggca gctgttgctc ctgctgctgc tgctgctgcc tctcacactg    4500
gtgctgctgg cagccgcctg gggccttcgc tggcaaaggg caagaaggag ggggagctc    4560
caccctgggg tgcccctccc ctcccatccc taggaattcc gccccccccc ctaacgttac    4620
tggccgaagc cgcttggaat aaggccggtg tgcgtttgtc tatatgttat tttccaccat    4680
attgccgtct tttggcaatg tgagggcccg gaaacctggc cctgtcttct tgacgagcat    4740
tcctagggggg ctttcccctc tcgccaaagg aatgcaaggt ctgttgaatg tcgtgaagga    4800
agcagttcct ctggaagctt cttgaagaca aacaacgtct gtagcgaccc tttgcaggca    4860
gcggaacccc ccacctggcg acaggtgcct ctgcggccaa agccacgtg tataagatac     4920
acctgcaaag gcggcacaac cccagtgcca cgttgtgagt tggatagttg tggaaagagt    4980
caaatggctc tcctcaagcg tattcaacaa ggggctgaag gatgcccaga aggtacccca    5040
ttgtatggga tctgatctgg ggcctcggtg cacatgcttt acatgtgttt agtcgaggtt    5100
aaaaaaacgt ctaggccccc cgaaccacgg ggacgtggtt ttcctttgaa aaacacgatg    5160
ataatatggc cacaaccatg gacgggccgc gcctgctgct gttgctgctt ctggggggtgt    5220
cccttggagg tgccaaggag gcatgcccca caggcctgta cacacacagc ggtgagtgct    5280
gcaaagcctg caacctgggc gagggtgtgg cccagccttg tggagccaac cagaccgtgt    5340
gtgagccctg cctggacagc gtgacgttct ccgacgtggt gagcgcgacc gagccgtgca    5400
agccgtgcac cgagtgcgtg gggctccaga gcatgtcggc gccgtgcgtg gaggccgacg    5460
acgccgtgtg ccgctgcgcc tacggctact accaggatga gacgactggg cgctgcgagg    5520
cgtgccgcgt gtgcgaggcg ggctcgggcc tcgtgttctc ctgccaggac aagcagaaca    5580
ccgtgtgcga ggagtgcccc gacggcacgt attccgacga ggccaaccac gtggacccgt    5640
gcctgccctg caccgtgtgc gaggacaccg agcgccagct ccgcgagtgc acacgctggg    5700
ccgacgccga gtgcgaggag atccctggcc gttggattac acggtccaca ccccccagagg    5760
gctcggacag cacagccccc agcacccagg agcctgaggc acctccagaa caagacctca    5820
tagccagcac ggtggcaggt gtggtgacca cagtgatggg cagctcccag cccgtggtga    5880
cccgaggcac caccgacaac ctcatccctg tctattgctc catcctggct gctgtggttg    5940
tgggccttgt ggcctacata gccttcaaga ggtggaacag tcatcgatat cctcgaggtc    6000
accgcggtct agagtcgacc tgcagccaag cttatcgata aaataaaaga ttttatttag    6060
tctccagaaa aaggggggaa tgaaagaccc cacctgtagg tttggcaagc tagcttaagt    6120
aacgccattt tgcaaggcat ggaaaataca taactgagaa tagagaagtt cagatcaagg    6180
ttaggaacag agagacagca gaatatgggc caaacaggat atctgtggta agcagttcct    6240
gccccggctc agggccaaga acagatggtc cccagatgcg gtcccgccct cagcagtttc    6300
tagagaacca tcagatgttt ccagggtgcc ccaaggacct gaaatgaccc tgtgccttat    6360
ttgaactaac caatcagttc gcttctcgct tctgttcgcg cgcttctgct ccccgagctc    6420
aataaaagag cccacaaccc ctcactcggc gcgccagtcc tccgatagac tgcgtcgccc    6480
gggtacccgt gtatccaata aaccctcttg cagttgcatc cgacttgtgg tctcgctgtt    6540
ccttgggagg gtctcctctg agtgattgac taccgctcag cggggggtcttt tcatgggtaa    6600
cagtttcttg aagttggaga caacattct gagggtagga gtcgaatatt aagtaatcct    6660
gactcaatta gccactgttt tgaatccaca tactccaata ctcctgaaat agttcattat    6720
ggacagcgca gaaagagctg gggagaattg tgaaattgtt atccgctcac aattccacac    6780
aacatacgag ccggaagcat aaagtgtaaa gcctggggtg cctaatgagt gagctaactc    6840
```

| | |
|---|---|
| acattaattg cgttgcgctc actgcccgct ttccagtcgg aaacctgtc gtgccagctg | 6900 |
| cattaatgaa tcggccaacg cgcggggaga ggcggtttgc gtattgggcg ctcttccgct | 6960 |
| tcctcgctca ctgactcgct gcgctcggtc gttcggctgc ggcgagcggt atcagctcac | 7020 |
| tcaaaggcgg taatacggtt atccacagaa tcagggata acgcaggaaa gaacatgtga | 7080 |
| gcaaaaggcc agcaaaaggc caggaaccgt aaaaaggccg cgttgctggc gttttttccat | 7140 |
| aggctccgcc cccctgacga gcatcacaaa atcgacgct caagtcgag gtggcgaaac | 7200 |
| ccgacaggac ta | 7212 |

<210> SEQ ID NO 2
<211> LENGTH: 7458
<212> TYPE: DNA
<213> ORGANISM: Murine endogenous retrovirus

<400> SEQUENCE: 2

| | |
|---|---|
| tttgaaagac ccacccgta ggtggcaagc tagcttaagt aacgccactt tgcaaggcat | 60 |
| ggaaaatac ataactgaga atagaaaagt tcagatcaag gtcaggaaca agaaacagc | 120 |
| tgaataccaa acaggatatc tgtggtaagc ggttcctgcc ccggctcagg gccaagaaca | 180 |
| gatgagacag ctgagtgatg ggccaaacag gatatctgtg gtaagcagtt cctgccccgg | 240 |
| ctcggggcca agaacagatg gtccccagat gcggtccagc cctcagcagt ttctagtgaa | 300 |
| tcatcagatg tttccagggt gccccaagga cctgaaaatg accctgtacc ttatttgaac | 360 |
| taaccaatca gttcgcttct cgcttctgtt cgcgcgcttc cgctctccga gctcaataaa | 420 |
| agagcccaca acccctcact cggcgcgcca gtcttccgat agactgcgtc gcccgggtac | 480 |
| ccgtattccc aataaagcct cttgctgttt gcatccgaat cgtggtctcg ctgttccttg | 540 |
| ggagggtctc ctctgagtga ttgactaccc acgacggggg tctttcattt gggggctcgt | 600 |
| ccggatttg gagaccctg cccaggacc accgaccac caccgggag taagctggcc | 660 |
| agcaacttat ctgtgtctgt ccgattgtct agtgtctatg tttgatgtta tgcgcctgcg | 720 |
| tctgtactag ttagctaact agctctgtat ctggcggacc cgtggtggaa ctgacgagtt | 780 |
| ctgaacaccc ggccgcaacc ctgggagacg tcccaggac tttgggggcc gttttttgtgg | 840 |
| cccgacctga ggaagggagt cgatgtggaa tccgacccg tcaggatatg tggttctggt | 900 |
| aggagacgag aacctaaaac agttcccgcc tccgtctgaa ttttttgcttt cggtttggaa | 960 |
| ccgaagccgc gcgtcttgtc tgctgcagcg ctgcagcatc gttctgtgtt gtctctgtct | 1020 |
| gactgtgttt ctgtatttgt ctgaaaatta gggccagact gttaccactc ccttaagttt | 1080 |
| gaccttaggt cactggaaag atgtcgagcg gatcgctcac aaccagtcgg tagatgtcaa | 1140 |
| gaagagacgt tgggttacct tctgctctgc agaatggcca acctttaacg tcggatggcc | 1200 |
| gcgagacggc acctttaacc gagacctcat cacccaggtt aagatcaagg tcttttcacc | 1260 |
| tggcccgcat ggacacccag accaggtccc ctacatcgtg acctgggaag ccttggcttt | 1320 |
| tgacccccct cccctgggtca agccctttgt acaccctaag cctccgcctc ctcttcctcc | 1380 |
| atccgccccg tctctccccc ttgaacctcc tcgttcgacc ccgcctcgat cctcccttta | 1440 |
| tccagccctc actccttctc taggcgccgg aattcgttgt accatggatt ttcaggtgca | 1500 |
| gattttcagc ttcctgctaa tcagtgcctc agtcataatg tctagacagg tacaactgca | 1560 |
| gcagtcagga cctgaactga agaagcctgg agagacagtc aagatctcct gcaaggcctc | 1620 |
| tgggtatcct ttcacaaact atggaatgaa ctgggtgaag caggctccag acagggttt | 1680 |

```
aaagtggatg ggctggatta acacctccac tggagagtca acatttgctg atgacttcaa    1740
gggacggttt gacttctctt tggaaacctc tgccaacact gcctatttgc agatcaacaa    1800
cctcaaaagt gaagacatgg ctacatattt ctgtgcaaga tgggaggttt accacggcta    1860
cgttccttac tggggccaag ggaccacggt caccgtttcc tctggcggtg gcggttctgg    1920
tggcggtggc tccggcggtg gcggttctga catccagctg acccagtctc acaaattcct    1980
gtccacttca gtaggagaca gggtcagcat cacctgcaag gccagtcagg atgtgtataa    2040
tgctgttgcc tggtatcaac agaaaccagg acaatctcct aaacttctga tttactcggc    2100
atcctcccgg tacactggag tcccttctcg cttcactggc agtggctctg gccggatt t   2160
cactttcacc atcagcagtg tgcaggctga agacctggca gtttatttct gtcagcaaca    2220
ttttcgtact ccattcacgt tcggctcggg gacaaaattg gagatcgaac aaaaactcat    2280
ctcagaagag gatctgaatg gggtcaccgt ctcttcagcg ctgagcaact ccatcatgta    2340
cttcagccac ttcgtgccgg tcttcctgcc agcgaagccc accacgacgc agcgccgcg    2400
accaccaaca ccggcgccca ccatcgcgtc gcagccctg tccctgcgcc cagaggcgtg    2460
ccggccagcg gcgggggggcg cagtgcacac gaggggggctg gatcctaagc tgttttgggc    2520
actggtcgtg gttgctggag tcctgttttg ttatggcttg ctagtgacag tggctctttg    2580
tgttatctgg acaaatagta gaaggaacag actccttcaa agtgactaca tgaacatgac    2640
tccccggagg cctgggctca ctcgaaagcc ttaccagccc tacgcccctg ccagagactt    2700
tgcagcgtac cgccccctcg agagagcaaa attcagcagg agtgctgaga ctgctgccaa    2760
cctgcaggac cccaaccagc tctacaatga gctcaatcta gggcgaagag aggaatatga    2820
cgtcttggag aagaagcggg ctcgggatcc agagatggga ggcaaacagc agaggaggag    2880
gaaccccag gaaggcgtat acaatgcact gcagaaagac aagatggcag aagcctacag    2940
tgagatcggc acaaaggcg agaggcggag aggcaagggg cacgatggcc tttaccaggg    3000
tctcagtact gccaccaagg acacctatga tgccctgcat atgcagaccc tggccctcg    3060
ctaactcgag gatccggctg tggaatgtgt gtcagttagg gtgtggaaag tccccaggct    3120
ccccagcagg cagaagtatg caaagcatgc atctcaatta gtcagcaacc aggtgtggaa    3180
agtccccagg ctccccagca ggcagaagta tgcaaagcat gcatctcaat tagtcagcaa    3240
ccatagtccc gcccctaact ccgcccatcc cgcccctaac tccgcccagt tccgcccatt    3300
ctccgcccca tggctgacta attttttta tttatgcaga ggccgaggcc gcctcggcct    3360
ctgagctatt ccagaagtag tgaggaggct ttttggagg cctaggcttt tgcaaaaagc    3420
tggggctgca ggtcgaggcg gatctgatca agagacagga tgaggatcgt ttcgcatgat    3480
tgaacaagat ggattgcacg caggttctcc ggccgcttgg gtggagaggc tattcggcta    3540
tgactgggca caacagacaa tcggctgctc tgatgccgcc gtgttccggc tgtcagcgca    3600
ggggcgcccg gttcttttg tcaagaccga cctgtccggt gccctgaatg aactgcagga    3660
cgaggcagcg cggctatcgt ggctggccac gacgggcgtt ccttgcgcag ctgtgctcga    3720
cgttgtcact gaagcgggaa gggactggct gctattgggc gaagtgccgg gcaggatct    3780
cctgtcatct caccttgctc ctgccgagaa agtatccatc atggctgatg caatgcggcg    3840
gctgcatacg cttgatccgg ctacctgccc attcgaccac caagcgaaac atcgcatcga    3900
gcgagcacgt actcggatgg aagccggtct tgtcgatcag gatgatctgg acgaagagca    3960
tcaggggctc gcgccagccg aactgttcgc caggctcaag gcgcgcatgc ccgacggcga    4020
ggatctcgtc gtgacccatg gcgatgcctg cttgccgaat atcatggtgg aaaatggccg    4080
```

```
cttttctgga ttcatcgact gtggccggct gggtgtggcg gaccgctatc aggacatagc   4140
gttggctacc cgtgatattg ctgaagagct tggcggcgaa tgggctgacc gcttcctcgt   4200
gctttacggt atcgccgctc ccgattcgca gcgcatcgcc ttctatcgcc ttcttgacga   4260
gttcttctga gcgggactct ggggttcgat aaaataaaag attttattta gtctccagaa   4320
aaaggggga atgaaagacc ccacctgtag gtttggcaag ctagcttaag taacgccatt   4380
ttgcaaggca tggaaaaata cataactgag aatagaaag ttcagatcaa ggtcaggaac   4440
agatggaaca gctgaatatg gccaaacag atatctgtg gtaagcagtt cctgccccgg   4500
ctcagggcca agaacagatg gaacagctga atatgggcca acaggatat ctgtggtaag   4560
cagttcctgc cccggctcag ggccaagaac agatggtccc cagatgcggt ccagccctca   4620
gcagtttcta gagaaccatc agatgtttcc agggtgcccc aaggacctga atgaccctg   4680
tgccttattt gaactaacca atcagttcgc ttctcgcttc tgttcgcgcg cttctgctcc   4740
ccgagctcaa taaagagcc cacaacccct cactcggggc gccagtcctc cgattgactg   4800
agtcgcccgg gtaccgtgt atccaataaa ccctcttgca gttgcatccg acttgtggtc   4860
tcgctgttcc ttgggagggt ctcctctgag tgattgacta cccgtcagcg ggggtctttc   4920
atttgggggc tcgtccggga tcgggagacc cctgcccagg gaccaccgac ccaccaccgg   4980
gaggtaagct ggctgcctcg cgcgtttcgg tgatgacggt gaaaacctct gacacatgca   5040
gctcccggag acggtcacag cttgtctgta agcggatgcc gggagcagac aagcccgtca   5100
gggcgcgtca gcgggtgttg gcgggtgtcg ggcgcagcc atgacccagt cacgtagcga   5160
tagcggagtg tatactggct taactatgcg gcatcagagc agattgtact gagagtgcac   5220
catatgcggt gtgaaatacc gcacagatgc gtaaggagaa ataccgcat caggcgctct   5280
tccgcttcct cgctcactga ctcgctgcgc tcggtcgttc ggctgcggcg agcggtatca   5340
gctcactcaa aggcggtaat acggttatcc acagaatcag gggataacgc aggaaagaac   5400
atgtgagcaa aaggccagca aaaggccagg aaccgtaaaa aggccgcgtt gctggcgttt   5460
ttccataggc tccgccccc tgacgagcat cacaaaaatc gacgctcaag tcagaggtgg   5520
cgaaacccga caggactata aagataccag gcgtttcccc ctggaagctc cctcgtgcgc   5580
tctcctgttc cgaccctgcc gcttaccgga tacctgtccg cctttctccc ttcgggaagc   5640
gtggcgcttt ctcatagctc acgctgtagg tatctcagtt cggtgtaggt cgttcgctcc   5700
aagctgggct gtgtgcacga accccccgtt cagcccgacc gctgcgcctt atccggtaac   5760
tatcgtcttg agtccaaccc ggtaagacac gacttatcgc cactggcagc agccactggt   5820
aacaggatta gcagagcgag gtatgtaggc ggtgctacag agttcttgaa gtggtggcct   5880
aactacggct acactagaag gacagtattt ggtatctgcg ctctgctgaa gccagttacc   5940
ttcggaaaaa gagttggtag ctcttgatcc ggcaaacaaa ccaccgctgg tagcggtggt   6000
ttttttgttt gcaagcagca gattacgcgc agaaaaaaag gatctcaaga agatcctttg   6060
atcttttcta cggggtctga cgctcagtgg aacgaaaact cacgttaagg gattttggtc   6120
atgagattat caaaaaggat cttcacctag atccttttaa attaaaaatg aagttttaaa   6180
tcaatctaaa gtatatatga gtaaacttgg tctgacagtt accaatgctt aatcagtgag   6240
gcacctatct cagcgatctg tctatttcgt tcatccatag ttgcctgact ccccgtcgtg   6300
tagataacta cgatacggga gggcttacca tctggcccca gtgctgcaat gataccgcga   6360
gacccacgct caccggctcc agatttatca gcaataaacc agccagccgg aagggccgag   6420
```

```
cgcagaagtg gtcctgcaac tttatccgcc tccatccagt ctattaattg ttgccgggaa      6480
gctagagtaa gtagttcgcc agttaatagt ttgcgcaacg ttgttgccat tgctgcaggc      6540
atcgtggtgt cacgctcgtc gtttggtatg gcttcattca gctccggttc ccaacgatca      6600
aggcgagtta catgatcccc catgttgtgc aaaaaagcgg ttagctcctt cggtcctccg      6660
atcgttgtca gaagtaagtt ggccgcagtg ttatcactca tggttatggc agcactgcat      6720
aattctctta ctgtcatgcc atccgtaaga tgcttttctg tgactggtga gtactcaacc      6780
aagtcattct gagaatagtg tatgcggcga ccgagttgct cttgcccggc gtcaacacgg      6840
gataataccg cgccacatag cagaacttta aaagtgctca tcattggaaa acgttcttcg      6900
gggcgaaaac tctcaaggat cttaccgctg ttgagatcca gttcgatgta acccactcgt      6960
gcacccaact gatcttcagc atcttttact ttcaccagcg tttctgggtg agcaaaaaca      7020
ggaaggcaaa atgccgcaaa aaagggaata agggcgacac ggaaatgttg aatactcata      7080
ctcttccttt ttcaatatta ttgaagcatt tatcagggtt attgtctcat gagcggatac      7140
atatttgaat gtatttagaa aaataaacaa ataggggttc cgcgcacatt tccccgaaaa      7200
gtgccacctg acgtctaaga aaccattatt atcatgacat taacctataa aaataggcgt      7260
atcacgaggc cctttcgtct tcaagaattg ctagcaattg ctagcaattg ctagcaattc      7320
ataccagatc accgaaaact gtcctccaaa tgtgtccccc tcacactccc aaattcgcgg      7380
gcttctgcct cttagaccac tctaccctat tccccacact caccggagcc aaagccgcgg      7440
cccttccgtt tctttgct                                                   7458

<210> SEQ ID NO 3
<211> LENGTH: 7926
<212> TYPE: DNA
<213> ORGANISM: homosapiens

<400> SEQUENCE: 3
tttgaaagac cccacccgta ggtggcaagc tagcttaagt aacgccactt tgcaaggcat        60
ggaaaaatac ataactgaga atagaaaagt tcagatcaag gtcaggaaca agaaacagc       120 tgaataccaa acaggatatc tgtggtaagc ggttcctgcc ccggctcagg gccaagaaca       180
gatgagacag ctgagtgatg ggccaaacag gatatctgtg gtaagcagtt cctgccccgg       240
ctcggggcca agaacagatg gtccccagat gcggtccagc cctcagcagt ttctagtgaa       300
tcatcagatg tttccagggt gccccaagga cctgaaaatg accctgtacc ttatttgaac       360
taaccaatca gttcgcttct cgcttctgtt cgcgcgcttc cgctctccga gctcaataaa       420
agagcccaca acccctcact cggcgcgcca gtcttccgat agactgcgtc gcccgggtac       480
ccgtattccc aataaagcct cttgctgttt gcatccgaat cgtggtctcg ctgttccttg       540
ggagggtctc ctctgagtga ttgactaccc acgacggggg tctttcattt gggggctcgt       600 ccggatttg gagaccccctg cccagggacc accgacccac caccgggagg taagctggcc       660
agcaacttat ctgtgtctgt ccgattgtct agtgtctatg tttgatgtta tgcgcctgcg       720
tctgtactag ttagctaact agctctgtat ctggcggacc cgtggtggaa ctgacgagtt       780
ctgaacaccc ggccgcaacc ctgggagacg tcccagggac tttgggggcc gtttttgtgg       840
cccgacctga ggaagggagt cgatgtggaa tccgaccccg tcaggatatg tggttctggt       900
aggagacgag aacctaaaac agttcccgcc tccgtctgaa ttttgctttc ggtttggaa       960 ccgaagccgc gcgtcttgtc tgctgcagcg ctgcagcatc gttctgtgtt gtctctgtct      1020
gactgtgttt ctgtatttgt ctgaaaatta gggccagact gttaccactc ccttaagttt      1080
```

```
gaccttaggt cactggaaag atgtcgagcg gatcgctcac aaccagtcgg tagatgtcaa    1140
gaagagacgt tgggttacct tctgctctgc agaatggcca acctttaacg tcggatggcc    1200
gcgagacggc acctttaacc gagacctcat cacccaggtt aagatcaagg tcttttcacc    1260
tggcccgcat ggacacccag accaggtccc ctacatcgtg acctgggaag ccttggcttt    1320
tgacccccct ccctgggtca agcccttttgt acaccctaag cctccgcctc ctcttcctcc    1380
atccgccccg tctctccccc ttgaacctcc tcgttcgacc ccgcctcgat cctcccttta    1440
tccagccctc actccttctc taggcgccgg aattcgcggc cgtgacaaga gttactaaca    1500
gcccctctct ccaagctcac ttacaggctc tctacttagt ccagcacgaa gtctggagac    1560
ctctggcggc agcctaccaa gaacaactgg accgaccggt ggtacctcac ccttaccgag    1620
tcggcgacac agtgtgggtc cgccgacacc agactaagaa cctagaacct cgctggaaag    1680
gaccttacac agtcctgctg accaccccca ccgccctcaa agtagacggc atcgcagctt    1740
ggatacacgc cgcccacgtg aaggctgccg accccggggg tggaccatcc tctagactga    1800
cgcggccgct acgtaccatg attttcaggt gcagatttt cagcttcctg ctaatcagtg    1860
cctcagtcat aatgtctaga caggtacaac tgcagcagtc aggacctgaa ctgaagaagc    1920
ctggagagac agtcaagatc tcctgcaagg cctctgggta tcctttcaca aactatggaa    1980
tgaactgggt gaagcaggct ccaggacagg gtttaaagtg gatgggctgg attaacacct    2040
ccactggaga gtcaacattt gctgatgact caagggacg gtttgacttc tctttggaaa    2100
cctctgccaa cactgcctat ttgcagatca acaacctcaa aagtgaagac atggctacat    2160
atttctgtgc aagatgggag gtttaccacg gctacgttcc ttactgggc caagggacca    2220 cggtcaccgt ttcctctggc ggtggcggtt ctggtggcgg tggctccggc ggtggcggtt    2280
ctgacatcca gctgacccag tctcacaaat tcctgtccac ttcagtagga gacagggtca    2340
gcatcacctg caaggccagt caggatgtgt ataatgctgt tgcctggtat caacagaaac    2400
caggacaatc tcctaaactt ctgatttact cggcatcctc ccggtacact ggagtccctt    2460
ctcgcttcac tggcagtggc tctgggccgg atttcacttt caccatcagc agtgtgcagg    2520
ctgaagacct ggcagtttat ttctgtcagc aacattttcg tactccattc acgttcggct    2580
cggggacaaa attggagatc gaacaaaaac tcatctcaga agaggatctg aatggggtca    2640
ccgtctcttc agcgctgagc aactccatca tgtacttcag ccacttcgtg ccggtcttcc    2700
tgccagcgaa gcccaccacg acgccagcgc cgcgaccacc aacaccggcg cccaccatcg    2760
cgtcgcagcc cctgtccctg cgcccagagg cgtgccggcc agcggcgggg ggcgcagtgc    2820
acacgagggg gctggatccc ttttgggtgc tggtggtggt tggtggagtc ctggcttgct    2880
atagcttgct agtaacagtg gccttttatta ttttctgggt gaggagtaag aggagcaggc    2940
tcctgcacag tgactacatg aacatgactc ccgccgccc cgggcccacc cgcaagcatt    3000
accagcccta tgccccacca cgcgacttcg cagcctatcg ctccctcgag agagtgaagt    3060
tcagcaggag cgcagacgcc cccgcgtacc agcagggcca gaaccagctc tataacgagc    3120
tcaatctagg acgaagagag gagtacgatg ttttggacaa gagacgtggc cgggaccctg    3180
agatgggggg aaagccgaga aggaagaacc ctcaggaagg cctgtacaat gaactgcaga    3240
aagataagat ggcggaggcc tacagtgaga ttgggatgaa aggcgagcgc cggaggggca    3300
aggggcacga tggcctttac cagggtctca gtacagccac caaggacacc tacgacgccc    3360
ttcacatgca ggccctgccc cctcgctaac tcgagcggga tcaattccgc ccccccccta    3420
```

-continued

```
acgttactgg ccgaagccgc ttggaataag gccggtgtgc gtttgtctat atgttatttt    3480
ccaccatatt gccgtctttt ggcaatgtga gggcccggaa acctggccct gtcttcttga    3540
cgagcattcc tagggtctt tccctctcg ccaaaggaat gcaaggtctg ttgaatgtcg    3600
tgaaggaagc agttcctctg gaagcttctt gaagacaaac aacgtctgta gcgaccnttt    3660
```

```
ctgcggcgag cggtatcagc tcactcaaag gcggtaatac ggttatccac agaatcaggg      5880
gataacgcag gaaagaacat gtgagcaaaa ggccagcaaa aggccaggaa ccgtaaaaag      5940
gccgcgttgc tggcgttttt ccataggctc cgcccccctg acgagcatca caaaaatcga      6000
cgctcaagtc agaggtggcg aaacccgaca ggactataaa gataccaggc gtttccccct      6060
ggaagctccc tcgtgcgctc tcctgttccg accctgccgc ttaccggata cctgtccgcc      6120
tttctccctt cgggaagcgt ggcgctttct catagctcac gctgtaggta tctcagttcg      6180
gtgtaggtcg ttcgctccaa gctgggctgt gtgcacgaac cccccgttca gcccgaccgc      6240
tgcgccttat ccggtaacta tcgtcttgag tccaacccgg taagacacga cttatcgcca      6300
ctggcagcag ccactggtaa caggattagc agagcgaggt atgtaggcgg tgctacagag      6360
ttcttgaagt ggtggcctaa ctacggctac actagaagga cagtatttgg tatctgcgct      6420
ctgctgaagc cagttacctt cggaaaaaga gttggtagct cttgatccgg caaacaaacc      6480
accgctggta gcggtggttt ttttgtttgc aagcagcaga ttacgcgcag aaaaaaagga      6540
tctcaagaag atcctttgat cttttctacg ggtctgacg ctcagtggaa cgaaaactca      6600
cgttaaggga ttttggtcat gagattatca aaaaggatct tcacctagat ccttttaaat      6660
taaaaatgaa gttttaaatc aatctaaagt atatatgagt aaacttggtc tgacagttac      6720
caatgcttaa tcagtgaggc acctatctca gcgatctgtc tatttcgttc atccatagtt      6780
gcctgactcc ccgtcgtgta gataactacg atacgggagg gcttaccatc tggccccagt      6840
gctgcaatga taccgcgaga cccacgctca ccggctccag atttatcagc aataaaccag      6900
ccagccggaa gggccgagcg cagaagtggt cctgcaactt tatccgcctc catccagtct      6960
attaattgtt gccgggaagc tagagtaagt agttcgccag ttaatagttt gcgcaacgtt      7020
gttgccattg ctgcaggcat cgtggtgtca cgctcgtcgt ttggtatggc ttcattcagc      7080
tccggttccc aacgatcaag gcgagttaca tgatccccca tgttgtgcaa aaaagcggtt      7140
agctccttcg gtcctccgat cgttgtcaga agtaagttgg ccgcagtgtt atcactcatg      7200
gttatggcag cactgcataa ttctcttact gtcatgccat ccgtaagatg cttttctgtg      7260
actggtgagt actcaaccaa gtcattctga gaatagtgta tgcggcgacc gagttgctct      7320
tgcccggcgt caacacggga taataccgcg ccacatagca gaactttaaa agtgctcatc      7380
attggaaaac gttcttcggg gcgaaaactc tcaaggatct taccgctgtt gagatccagt      7440
tcgatgtaac ccactcgtgc acccaactga tcttcagcat cttttacttt caccagcgtt      7500
tctgggtgag caaaaacagg aaggcaaaat gccgcaaaaa agggaataag ggcgacacgg      7560
aaatgttgaa tactcatact cttcctttt caatattatt gaagcattta tcagggttat      7620
tgtctcatga gcggatacat atttgaatgt atttagaaaa ataaacaaat aggggttccg      7680
cgcacatttc cccgaaaagt gccacctgac gtctaagaaa ccattattat catgacatta      7740
acctataaaa ataggcgtat cacgaggccc tttcgtcttc aagaattcat accagatcac      7800
cgaaaactgt cctccaaatg tgtccccctc acactcccaa attcgcgggc ttctgcctct      7860
tagaccactc taccctattc cccacactca ccggagccaa agccgcggcc cttccgtttc      7920
tttgct                                                                7926
```

MODIFIED T CELLS AND USES THEREOF

CROSS REFERENCE TO RELATED APPLICATIONS

The present application is a U.S. national phase application under 35 U.S.C. § 371 of International Application No. PCT/AU2019/050660, filed on Jun. 25, 2019, designating the United States and published in English as WO 2020/000035 A1 on Jan. 2, 2020, which claims priority to AU application No. 2018902260, filed on Jun. 25, 2018. The content of each of these applications is expressly incorporated by reference in its entirety.

FIELD OF THE INVENTION

The present invention generally relates to T cells that are modified to enhance the efficiency of adoptive cellular therapy by modulating dendritic cell activity, a composition comprising modified T cells, vectors and methods for the treatment of cancer comprising administering modified T cells. In particular, the present invention provides modified T cells for use in adoptive cellular therapies for the treatment of solid tumours.

BACKGROUND OF THE INVENTION

Adoptive cellular therapy (ACT) using chimeric antigen receptor (CAR) T cells have been highly successful in treating haematological malignancies, such as such as acute lymphoblastic leukaemia (ALL) and chronic lymphocytic leukaemia (CLL) (Kalos et al. 2011, *Science Translational Medicine*, 3(95): 95ra73; Maude et al. 2014, *New England Journal of Medicine*, 371(16): 1507-17), but their success in solid tumours has been limited due to immunosuppression in the local tumour microenvironment. Tumour immunosuppression is fundamental to both the initiation and progression of tumours. Tumours use several mechanisms that facilitate immunosuppression including anti-inflammatory cytokine production, recruitment of subsets of regulatory immune cells comprising regulatory T cells (Tregs) and myeloid-derived suppressor cells (MDSCs), negative co-stimulation of effector T cells and the production of immunosuppressive metabolites. In the context of solid tumours, the inherent heterogeneity of tumour antigen expression also presents a barrier to the successful adaptation of ACT for use in the treatment of solid tumours. Significant therapeutic opportunity exists in modifying the tumour microenvironment from immunosuppressive to immune-activating to overcome the heterogeneity of tumour antigen expression. One such therapeutic approach is to enhance anti-tumour immunity via the innate immune response.

$CD141^+$ dendritic cells are highly efficient at cross-presenting tumour antigens and produce high levels of pro-inflammatory cytokines such as interleukin-12 (IL-12). The presence of $CD141^+$ dendritic cells has been shown to correlate with high levels of $CD8^+$ T cell infiltrate in melanoma (Spranger et al. 2017 *Cancer Cell*, 31: 711-23). Furthermore, in humanised mouse models, $CD141^+$ dendritic cells have been shown to be the most potent subset of human dendritic cells in terms of cytokine production and the ability to induce $CD4^+$ T cell responses (Meixlsperger et al. 2013, *Blood*, 121: 5034-44). Murine $CD103^+$ dendritic cells also exhibit similar characteristics to human $CD141^+$ dendritic cells.

Engineering T cells to enhance $CD141^+/CD103^+$ dendritic cell differentiation and function has the potential to overcome the issues associated with the inherent heterogeneity of tumour antigen expression in solid tumours by promoting de novo endogenous anti-tumour immune responses. In addition, $CD141^+/CD103^+$ dendritic cells are potent producers of IL-12 and therefore, increasing the number of $CD141^+/CD103^+$ dendritic cells has the potential to convert the tumour microenvironment from immunosuppressive to immunostimulatory. Finally, $CD141^+/CD103^+$ dendritic cells have also been shown to be crucial to the efficacy of ACT via the enhancement of T cell trafficking to the tumour site due to their ability to secrete high amounts of CXCL9/10 (Spranger, supra).

Consequently, there is a need to generate modified T cells that can promote the differentiation of $CD103^+/CD141^+$ dendritic cells to enhance ACT.

SUMMARY OF THE INVENTION

The present inventors have determined that T cells that are modified to express FMS-like tyrosine kinase ligand 3 (FLT3L) promote the differentiation of $CD141^+/CD103^+$ dendritic cells, which enhance anti-tumour T cell responses.

Accordingly, in one aspect of the present invention there is provided an isolated T cell that is modified to express exogenous FLT3L.

In a second aspect, the present invention provides a pharmaceutical composition comprising an isolated T cell that is modified to express exogenous FLT3L in accordance with the invention.

In a third aspect, the present invention provides a method for treating cancer comprising administration of a therapeutically effective amount of an isolated T cell that is modified to express exogenous FLT3L in accordance with the invention or a pharmaceutical composition comprising an isolated T cell that is modified to express exogenous FLT3L in accordance with the invention.

In a fourth aspect, the present invention provides a use of an isolated T cell that is modified to express exogenous FLT3L in accordance with the invention in the manufacture of a medicament for the treatment of cancer.

In a fifth aspect, the present invention provides a vector comprising a nucleic acid encoding FLT3L operably linked to a T cell-specific regulatory element.

In a sixth aspect, the present invention provides a viral particle comprising a nucleic acid encoding FLT3L.

In a seventh aspect, the present invention provides a method for treating cancer comprising taking a blood sample from a subject, isolating T cells from the blood sample, culturing the isolated T cells in vitro with the vectors according to the invention under conditions such that the nucleic acid encoded by the vector is expressed, and administering a therapeutically effective amount of the T cells to the subject.

In various alternative embodiments, the modified T cells are further modified to express a chimeric antigen receptor (CAR), wherein the CAR comprises an antigen binding domain and at least one signaling domain.

U/mouse) from day 0-5 and anti-PD-1 or isotype control (200 µg/mouse) on days 0, 4, 8 and 12 post-treatment. Data represents mean±SEM, n=8 mice per group. **p<0.001 (Two-way ANOVA).

Figure 2:
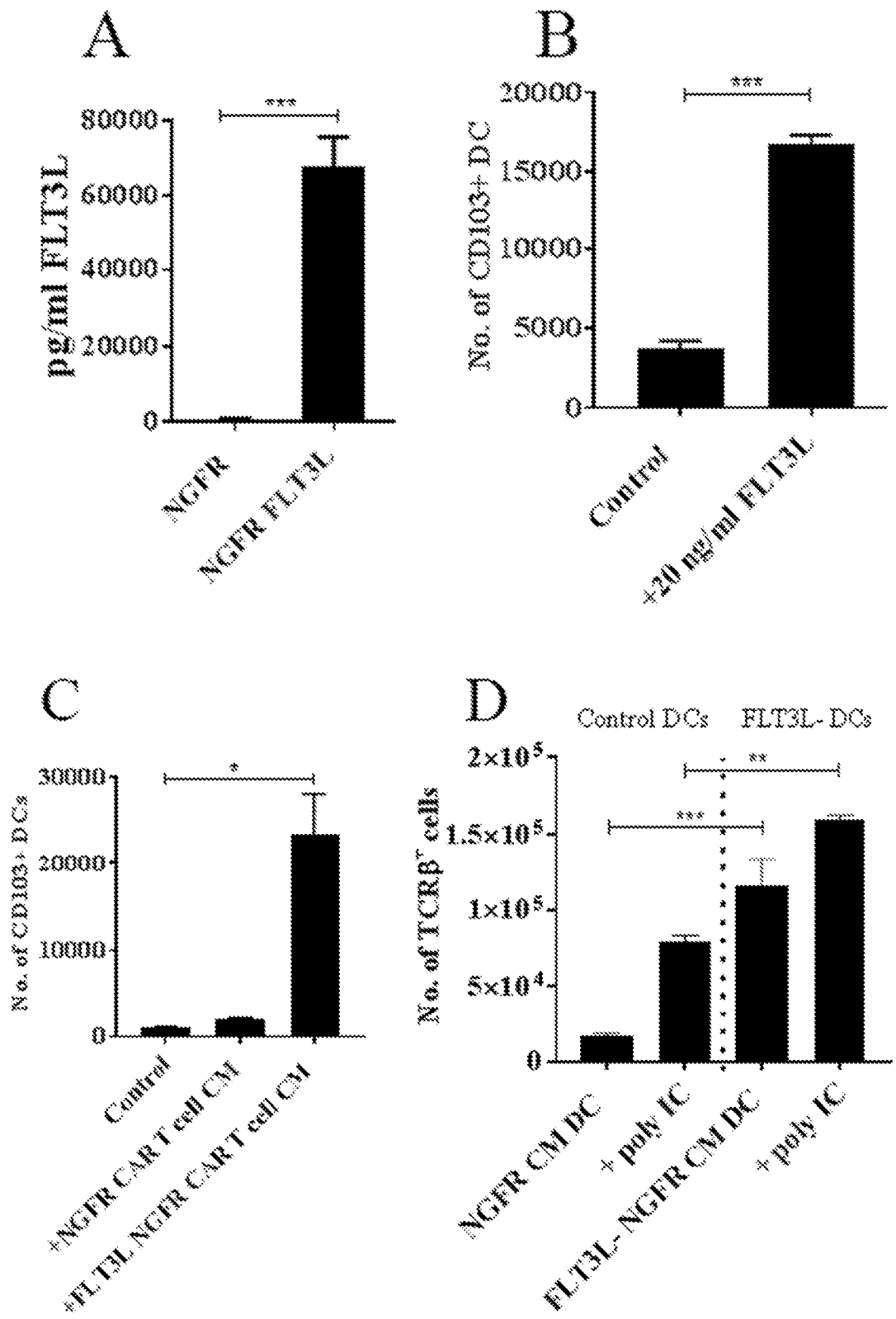
Figure 2:
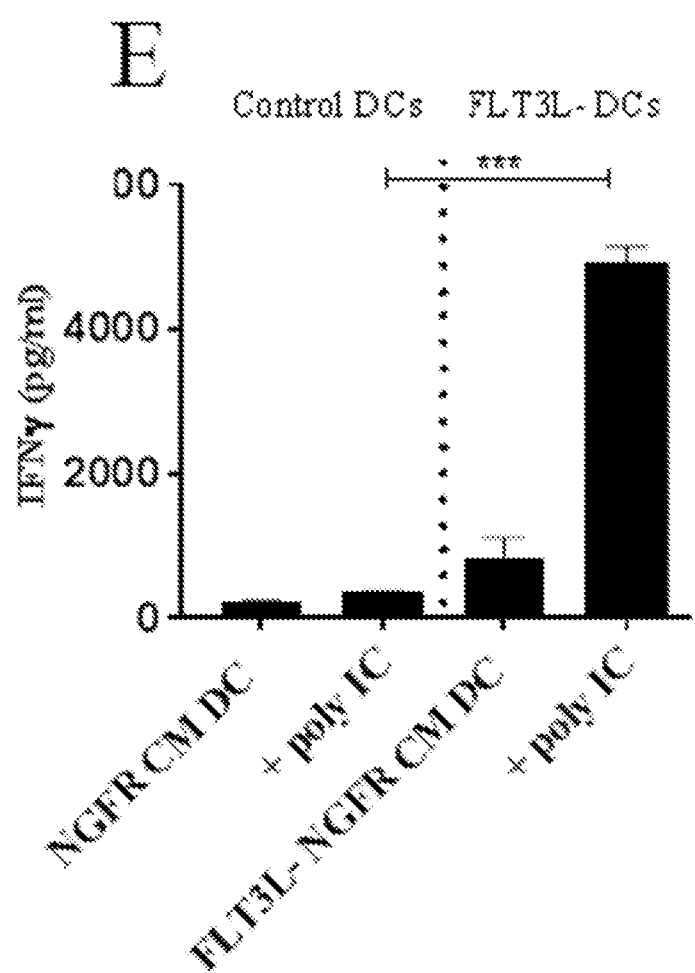

FIG. 2 shows that FLT3L-expressing CAR T cells induce the differentiation of $CD103^+$ DCs which exhibit superior APC function. (A-E) A graphical representation of (A) FLT3L production (pg/mL; y-axis) in the supernatant of CAR T cells produced from wild-type splenocytes transduced with an anti-Her2 CAR and NGFR-FLT3L or control NGFR (x-axis). Data represents mean±SEM of n=6, *p<0.001 (Student's T test); (B) the number of $CD103^+$ DCs (y-axis) generated from the bone marrow of wild type mice using 25 ng/mL GM-CSF and 20 ng/mL of FLTL3 (x-axis); or (C) the conditioned media of NGFR-FLT3L CAR T cells or NGFR control CAR T cells (x-axis); (D) the number of viable $TCRβ^+$ cells (y-axis) generated from the co-culturing of $2×10^4$ DCs from (C) with $4×10^4$ naïve OT-IT cells in the presence of SIINFEKL peptide (1 µg/mL) in the presence or absence of polyinosinic:polycytidylic acid (polyIC; y-axis); and (E) the concentration of IFNγ (pg/mL; y-axis) in the supernatants was determined. (B)-(E) Data represented as the mean±SD of triplicate cultures from a representative experiment of n>3. * p<0.001, **p<0.01, *p<0.05 (One way ANOVA/Tukey's).

Figure 3:
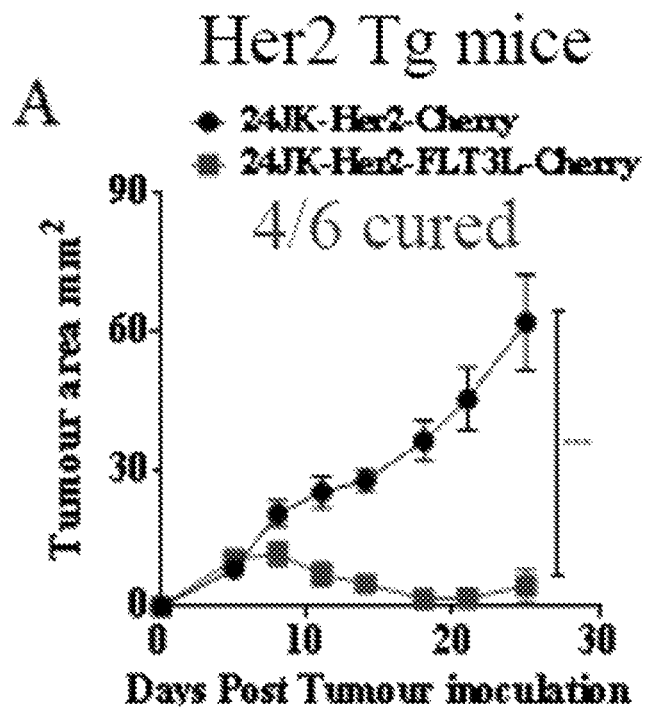
Figure 3:
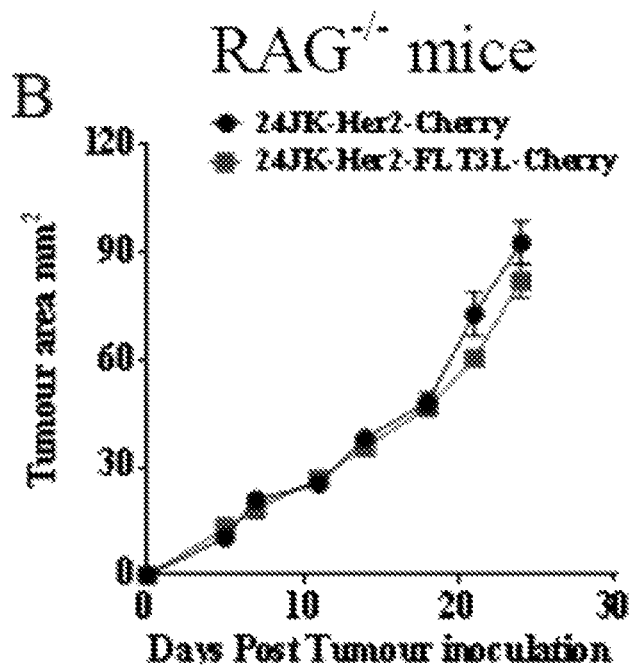
Figure 3:
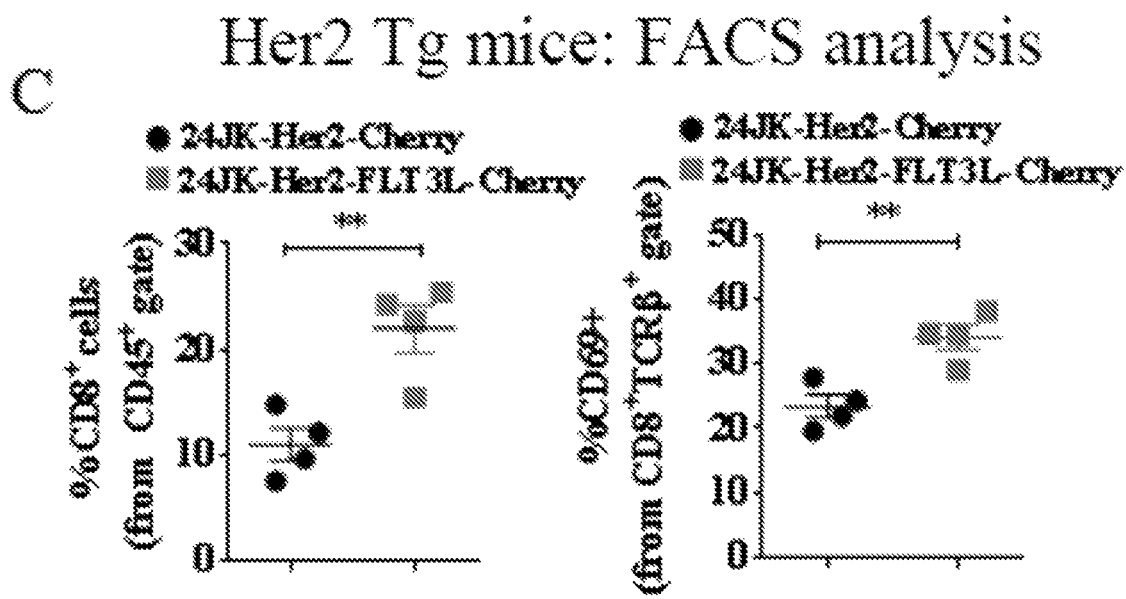

FIG. 3 shows FLT3L expression at the tumour site enhances anti-tumour immunity. A graphical representation of tumour area ($mm^2$; y-axis) against time (days post-tumour inoculation; x-axis) for (A) Her2 transgenic (Tg) and (B) $RAG^{-/-}$ mice sub-cutaneously injected with $5×10^5$ 24 JK-Her2 tumour cells engineered to express FLT3L; (C) $CD8^+$ frequency (%; y-axis) and (D) CD69 expression (%; y-axis) in the tumour-infiltrating lymphocytes from tumours excised at 8 days post-tumour inoculation. Data is represented as mean±SEM of 4-6 mice per group. *p<0.001, p<0.01 (A Two-way ANOVA/Tukey's, C Unpaired t test).

Figure 4:
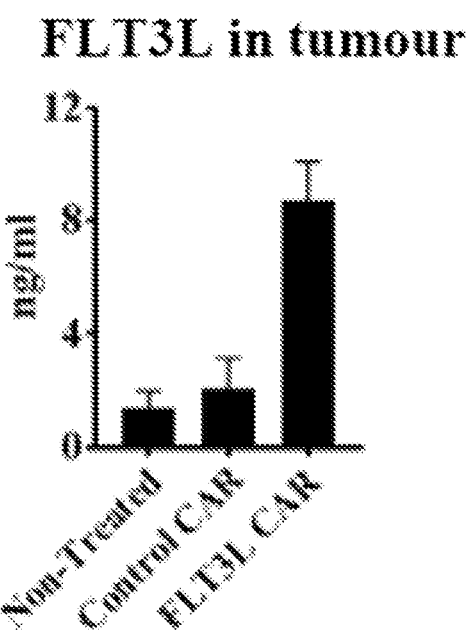
Figure 4:
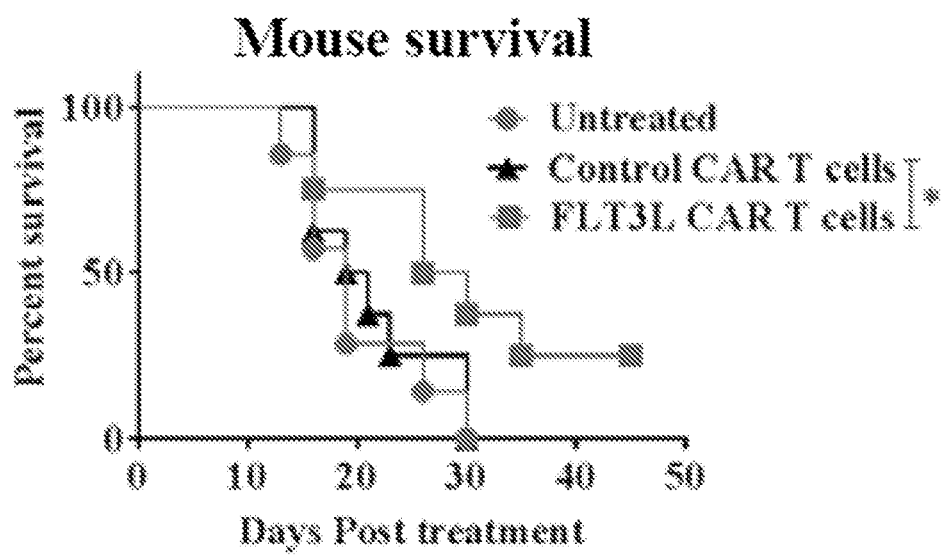
Figure 4:
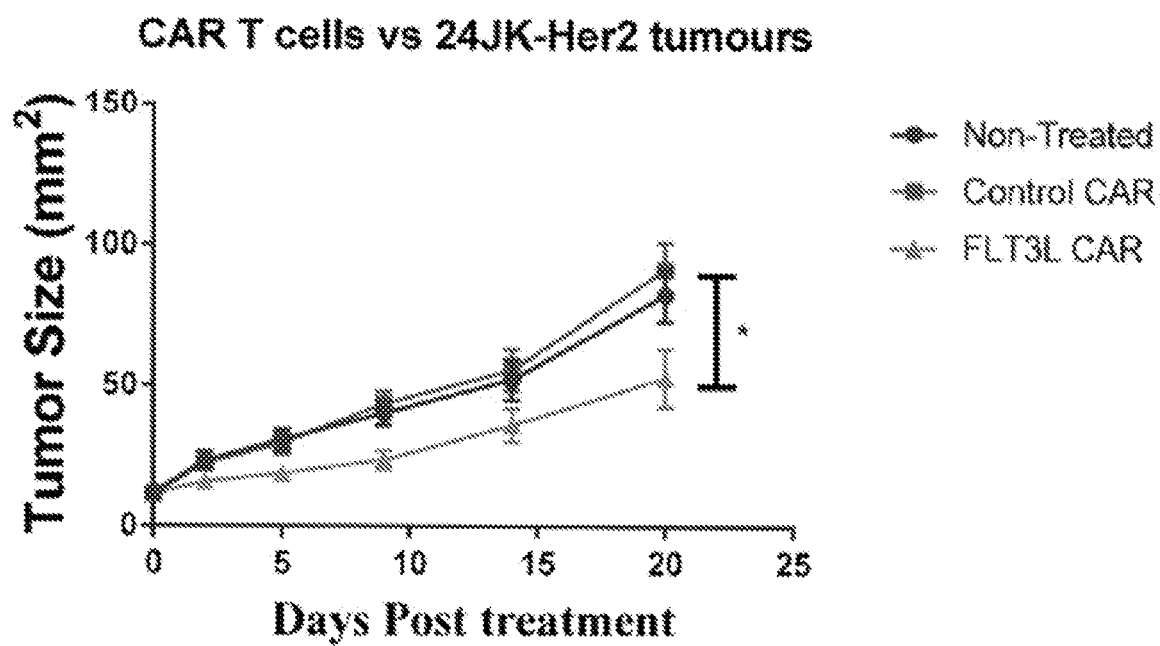

FIG. 4 shows FLT3L-expressing anti-Her2 CAR T cells elicit greater therapeutic efficacy. Her2 transgenic mice were injected with $5×10^5$ 24 JK-Her2 tumour cells engineered to express FLT3L, at day 9 mice were irradiated (0.5 Gy) and were treated with $1×10^7$ anti-Her2 CAR T cells on days 9 and 10, mice were also treated with 50,000 U/IL-2 on days 9-13. (A) A graphical representation of concentration of FLT3L (ng/mL; y-axis) of tumours six days post-treatment with FLT3L CAR T cells or control CAR T cells (x-axis). Data is the mean±SD of 2-3 mice per group. (B) A graphical representation of survival (%; y-axis) against time (days post-treatment; x-axis) in mice treated with FLT3L CAR T cells or control CAR T cells when the tumour size was >100 $mm^2$. (C) A graphical representation of tumour size (mm2; y-axis) against time (days post-treatment; x-axis) in mice treated with FLT3L CAR T cells or control CAR T cells when the tumour size was >100 $mm^2$. n=6 mice per group. *p<0.05, Log rank.

Figure 5:
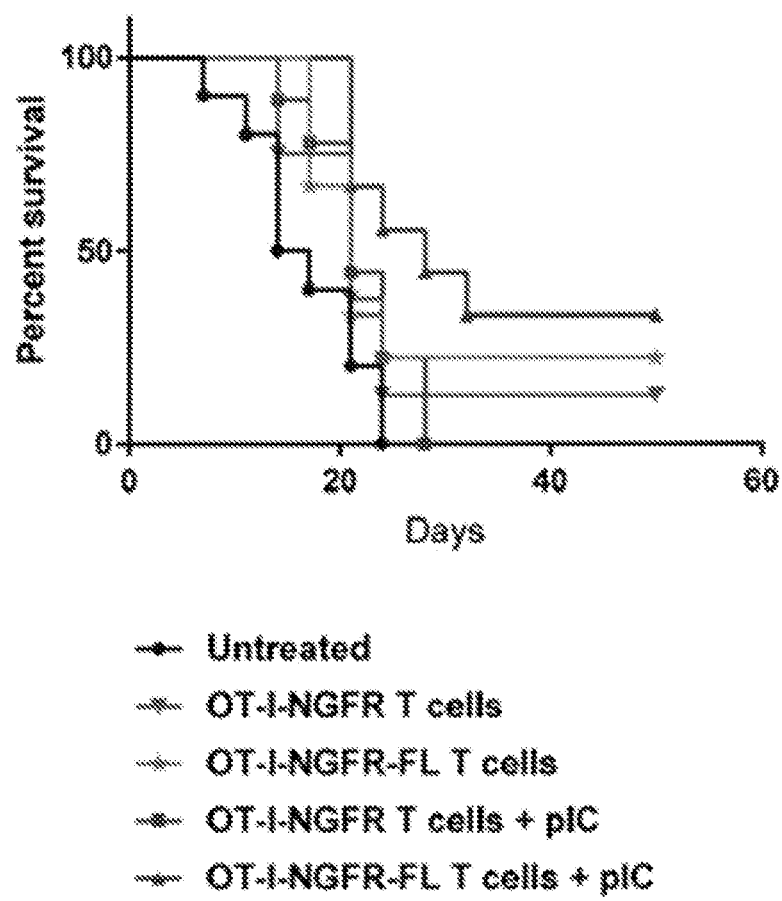

FIG. 5 shows FLT3L-expressing OT-I cells elicit greater therapeutic efficacy. A graphical representation of survival (%; y-axis) against time (days post-treatment; x-axis) in mice treated with FLT3L OT-I cells or control OT-I cells when the tumour size was >100 $mm^2$, both in the presence or absence of polyinosinic:polycytidylic acid (pIC).

Figure 6:
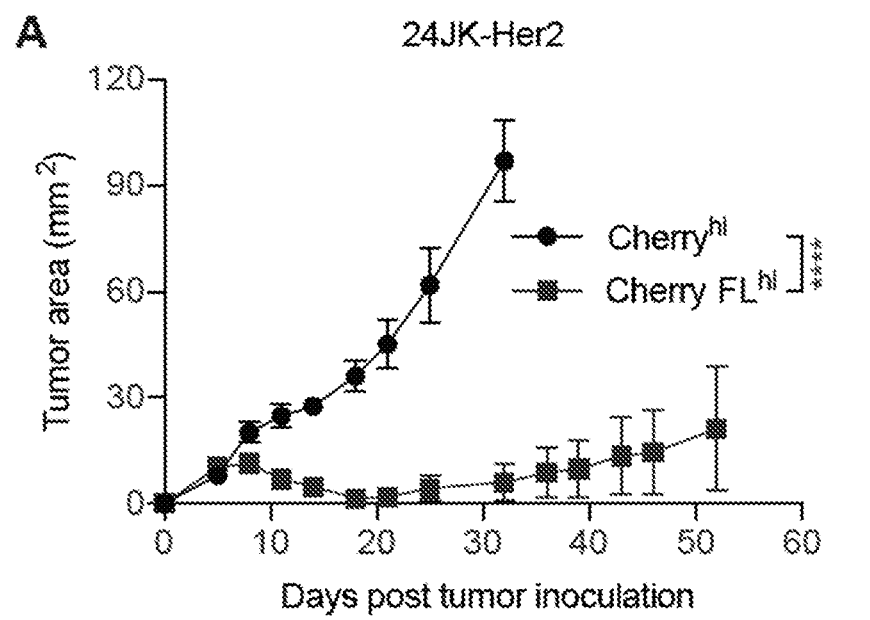
Figure 6:
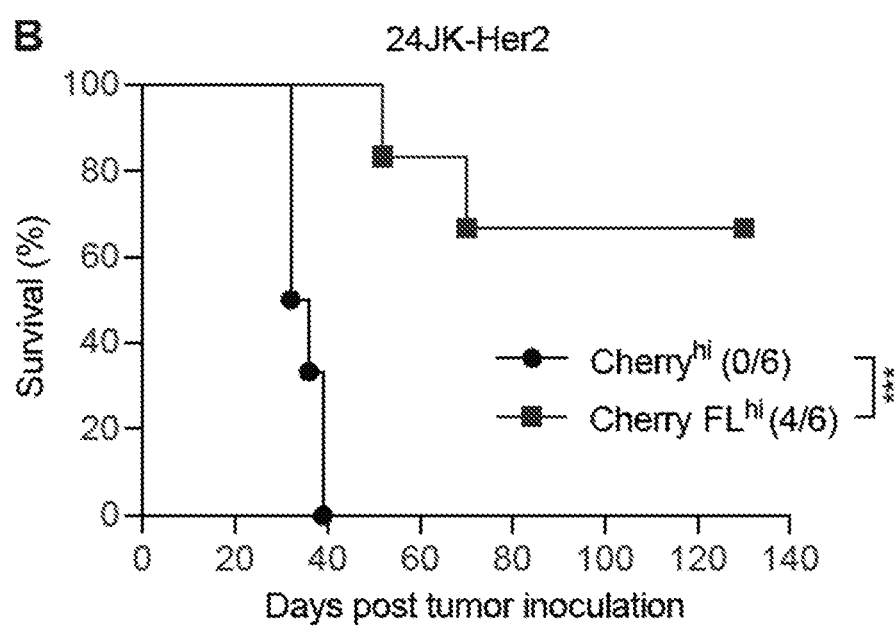
Figure 6:
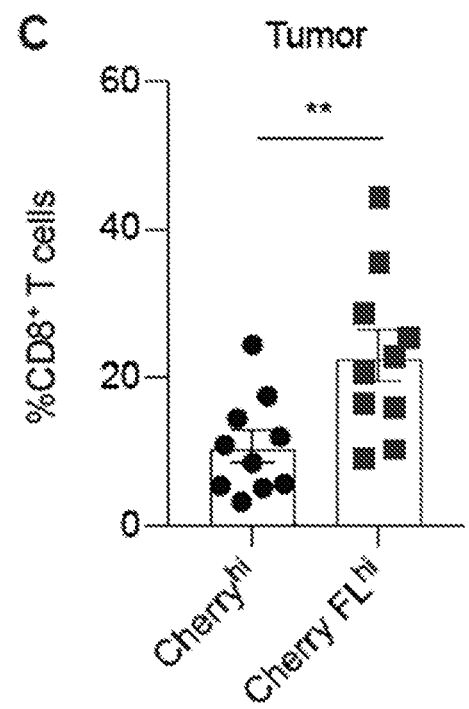
Figure 6:
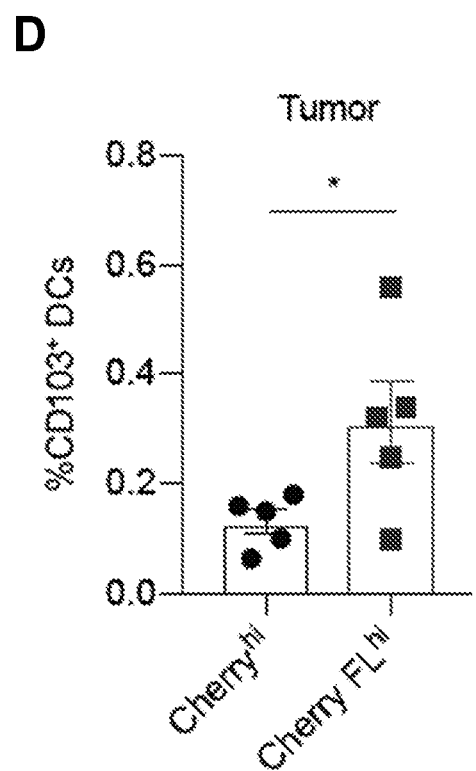
Figure 6:
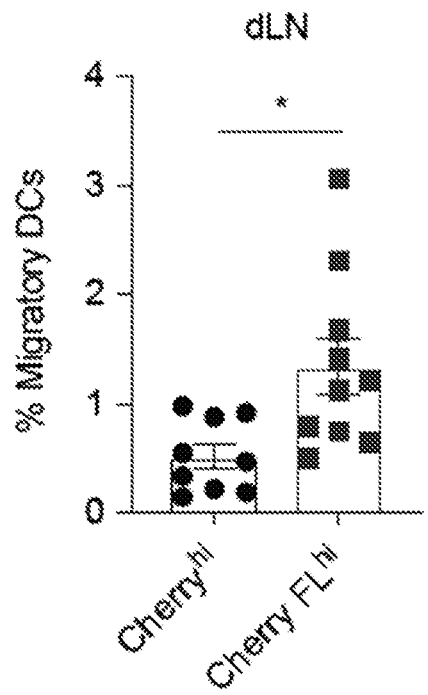
Figure 6:
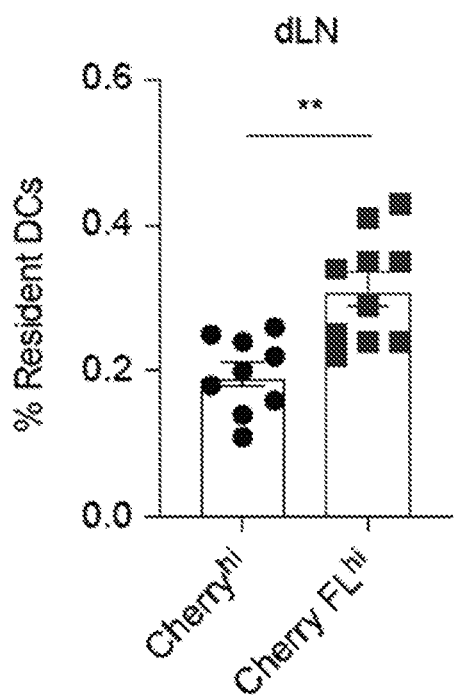
Figure 6:
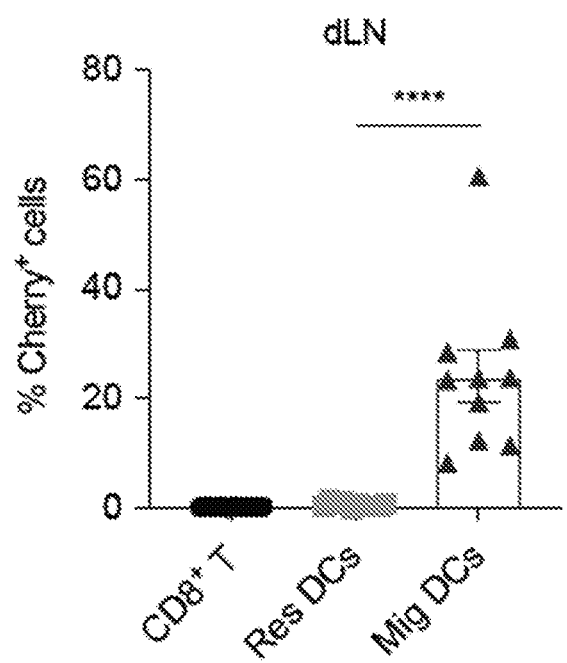
Figure 6:
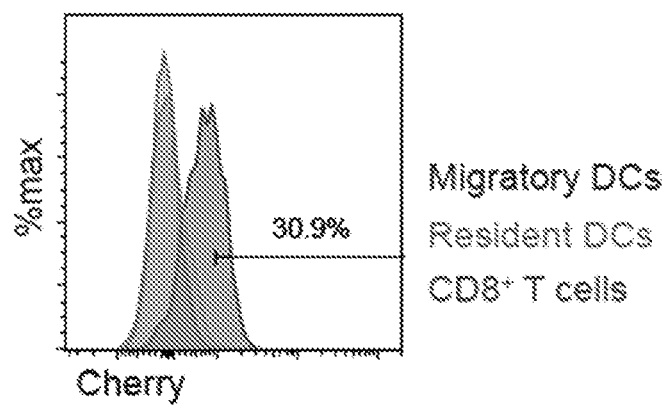
Figure 6:
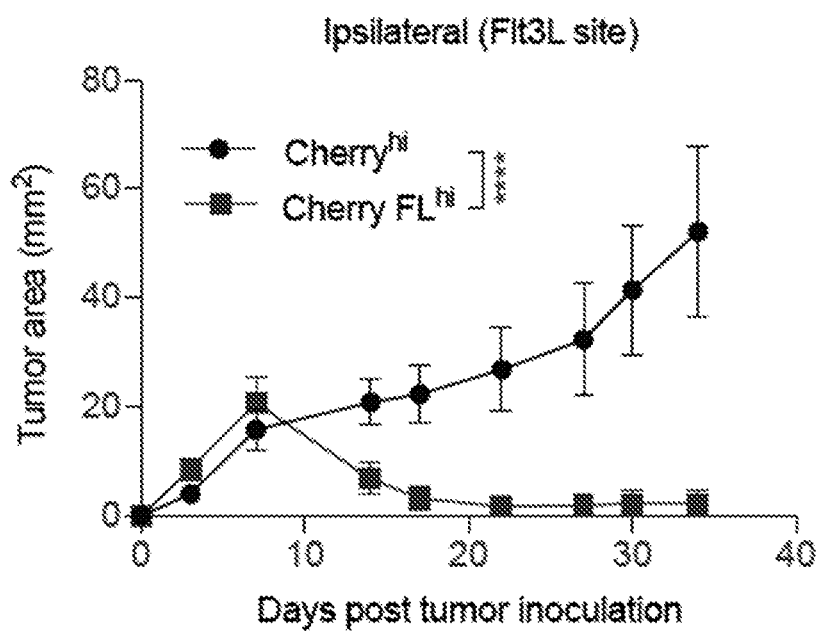
Figure 6:
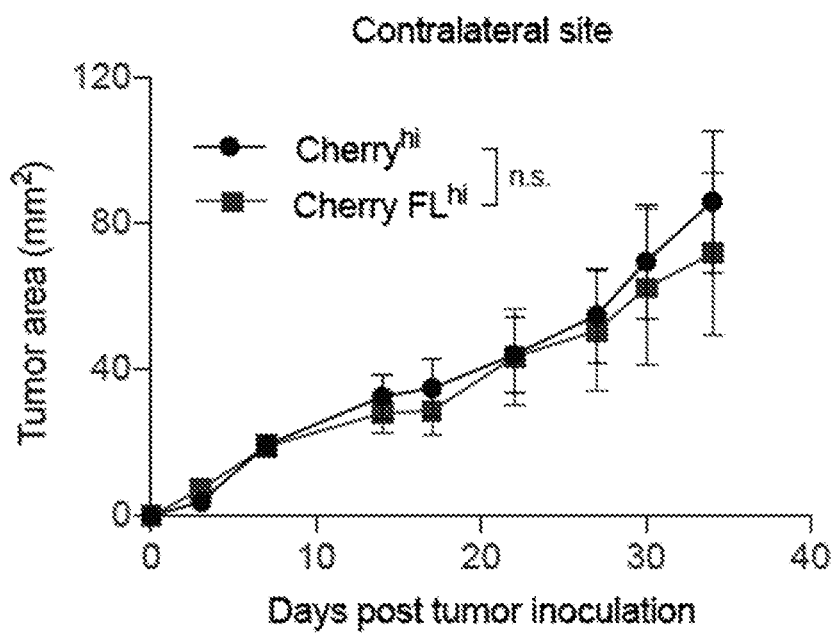
Figure 6:
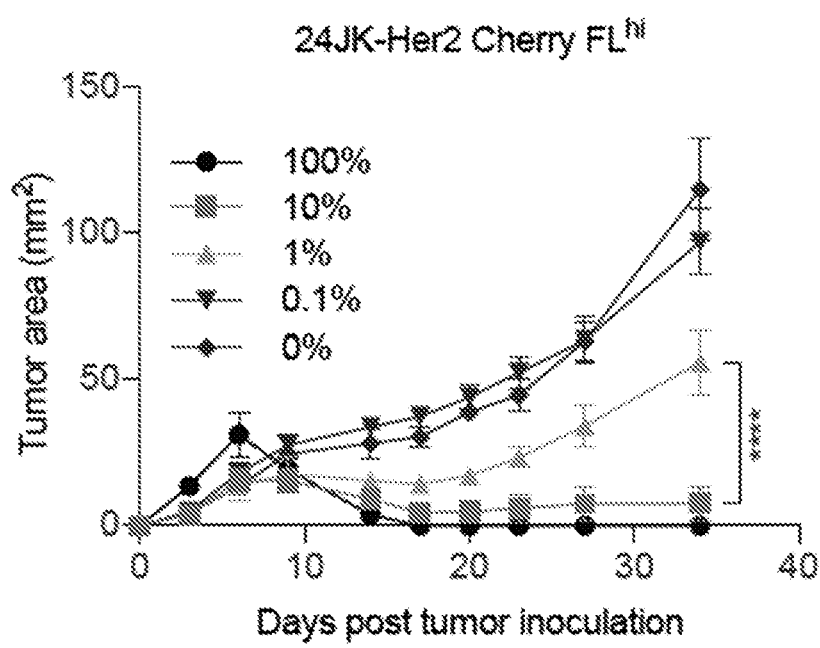
Figure 6:
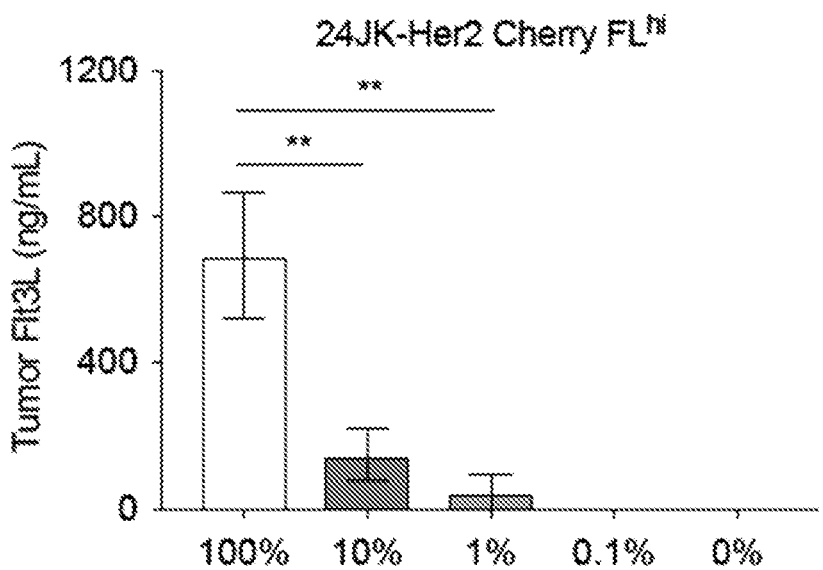
Figure 6:
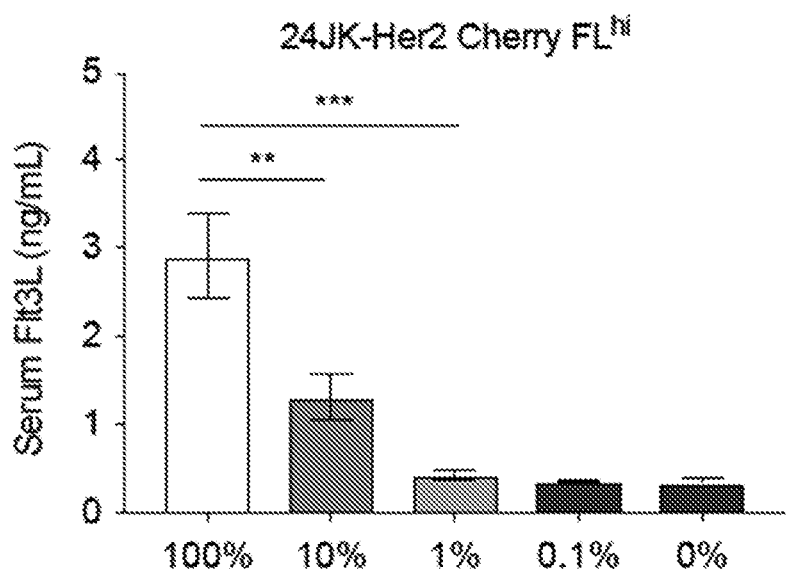
Figure 6:
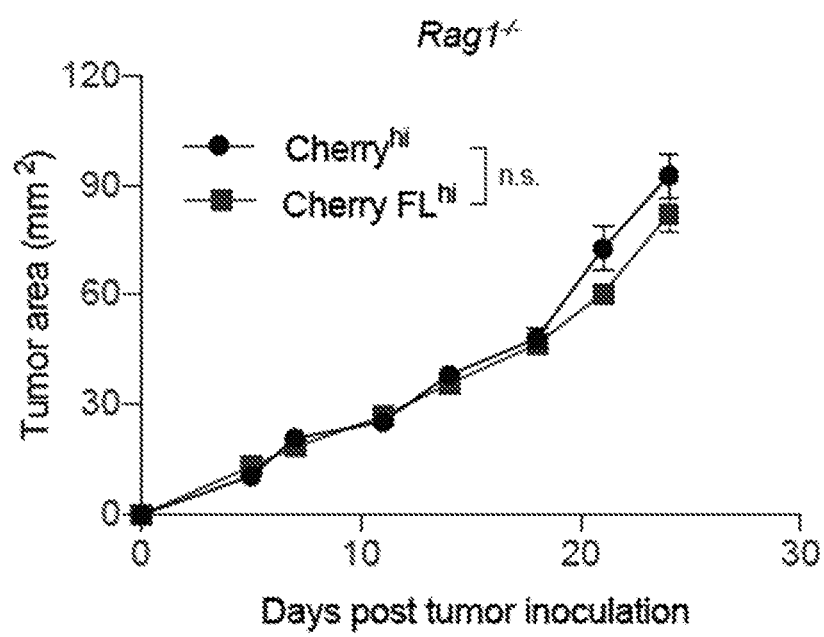

FIG. 6 shows that FLT3L expression induces tumour regression. (A) A graphical representation of tumour area ($mm^2$; y-axis) against time (days post-tumour inoculation; x-axis) in $hHer2^{+/-}$ mice subcutaneously injected with $5×10^5$ 24 JK-Her2 tumour cells engineered to express FLT3L (Cherry $FL^{hi}$) or control cells ($Cherry^{hi}$); (B) A graphical representation of survival (%; y-axis) against time (days post-tumour inoculation) in $hHer2^{+/-}$ mice subcutaneously injected with Cherry $FL^{hi}$ or $Cherry^{hi}$; (C-E) A graphical representation of (C) $CD8^+$ T cell frequency (%; y-axis), (D) $CD103^+$ DC frequency (%; y-axis), (E) migratory DC frequency (%; y-axis), and (F) resident DC frequency (%; y-axis) from tumours and tumour-draining lymph nodes (dLN) excised at 9 days post-tumour inoculation; (G-H) A graphical representation of $Cherry^+$ cell frequency (%; y-axis) in the respective populations; (I-J) A graphical representation of tumour size ($mm^2$; y-axis) against time (days post-tumour inoculation; x-axis) in mice inoculated on (I) the right (i.e., ipsilateral) flank or (J) the left (i.e., the contralateral) flank with either Cherry $FL^{hi}$ or $Cherry^{hi}$ cells; (K) A graphical representation of tumour size ($mm^2$; y-axis) against time (days post-tumour inoculation; x-axis) following titration of different ratios of Cherry $FL^{hi}$ and $Cherry^{hi}$ cells inoculated into the right flank of $hHer2^{+/-}$ transgenic mice; (L-M) A graphical representation of FLT3L concentration in (L) tumours and (M) serum (ng/mL; y-axis) against titration ratios of Cherry $FL^{hi}$ and $Cherry^{hi}$ cells (%; x-axis) at 6 days post-inoculation; and (N) A graphical representation of tumour size ($mm^2$; y-axis) against time (days post-tumour inoculation; x-axis) in $Rag1^{-/-}$ mice subcutaneously injected with $5×10^5$ Cherry $FL^{hi}$ or $Cherry^{hi}$ cells. Data is shown as mean±SEM of 3-10 mice per group. **p<0.0001, *p<0.001, **p<0.01, *p<0.05, n.s. not significant (A, I, J, K and N two-way ANOVA; G, L and M one-way ANOVA; C, D, E and F unpaired student's t test; and B Mantel-Cox test).

Figure 7:
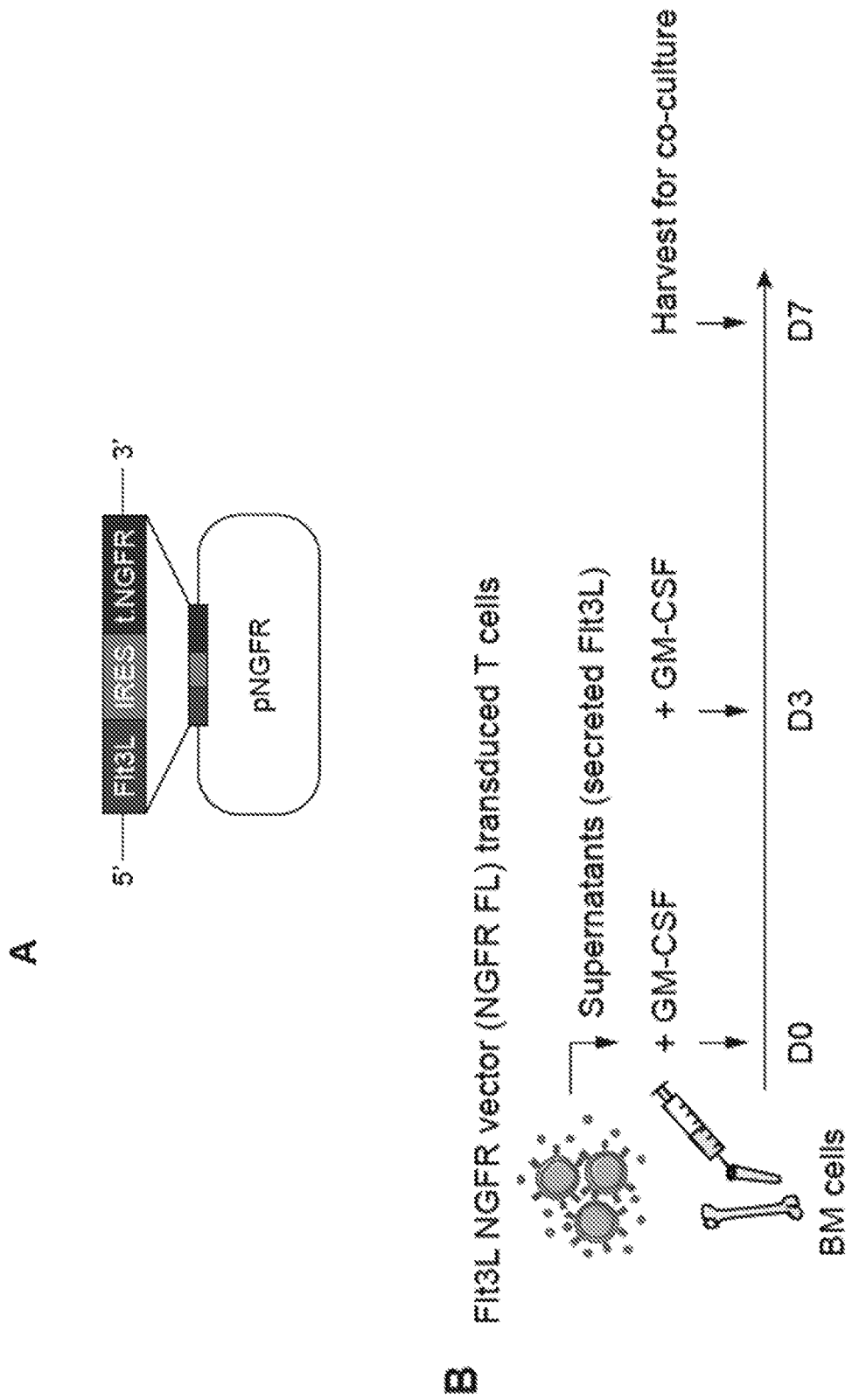
Figure 7:
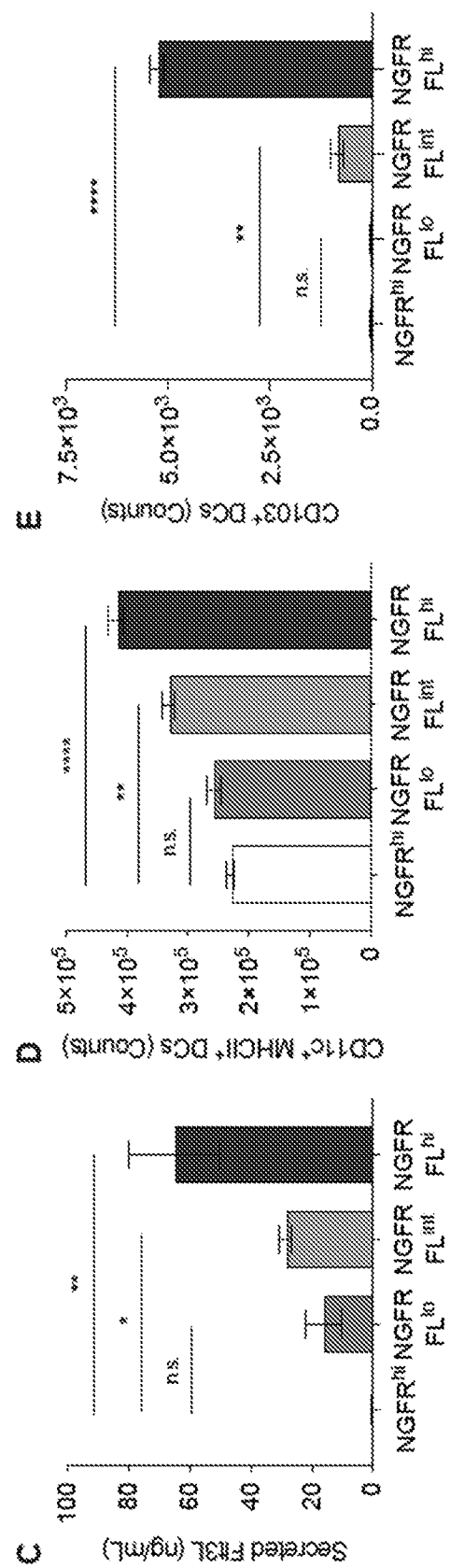
Figure 7:
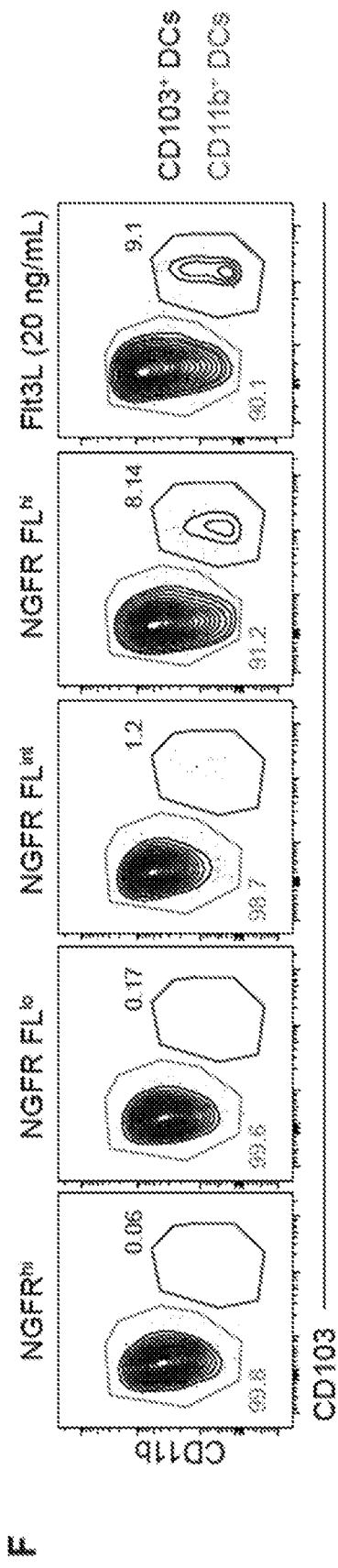
Figure 7:
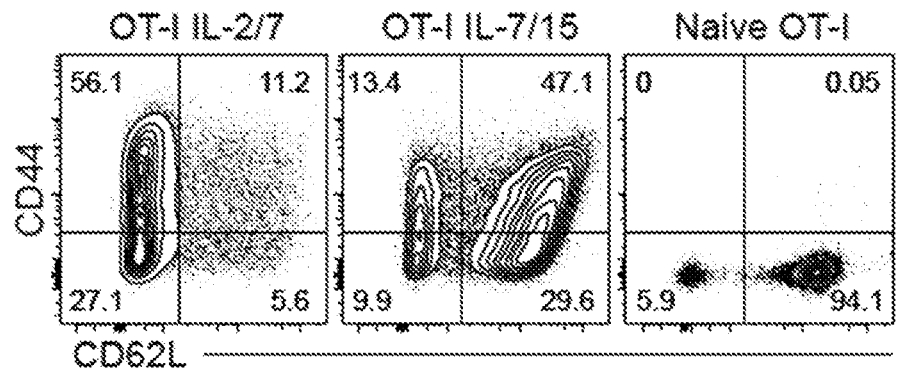
Figure 7:
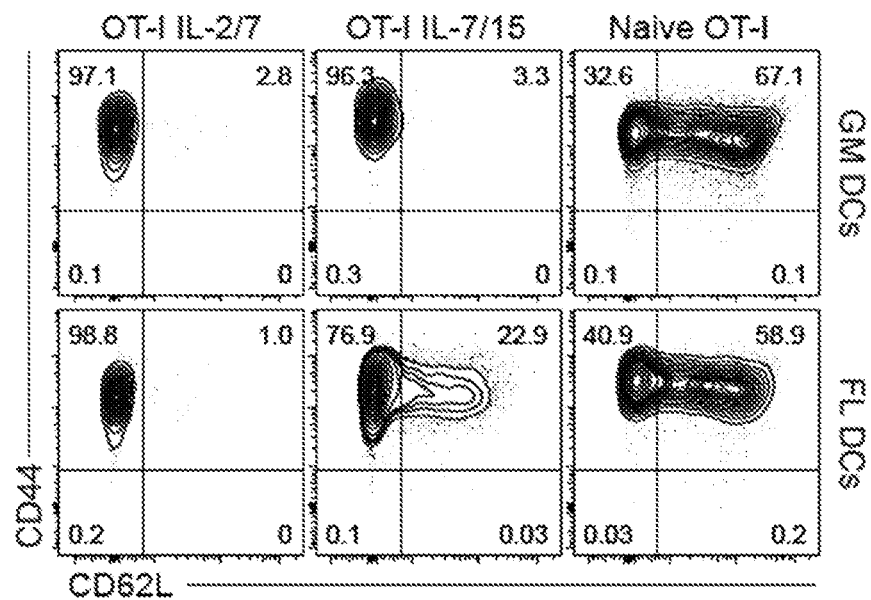
Figure 7:
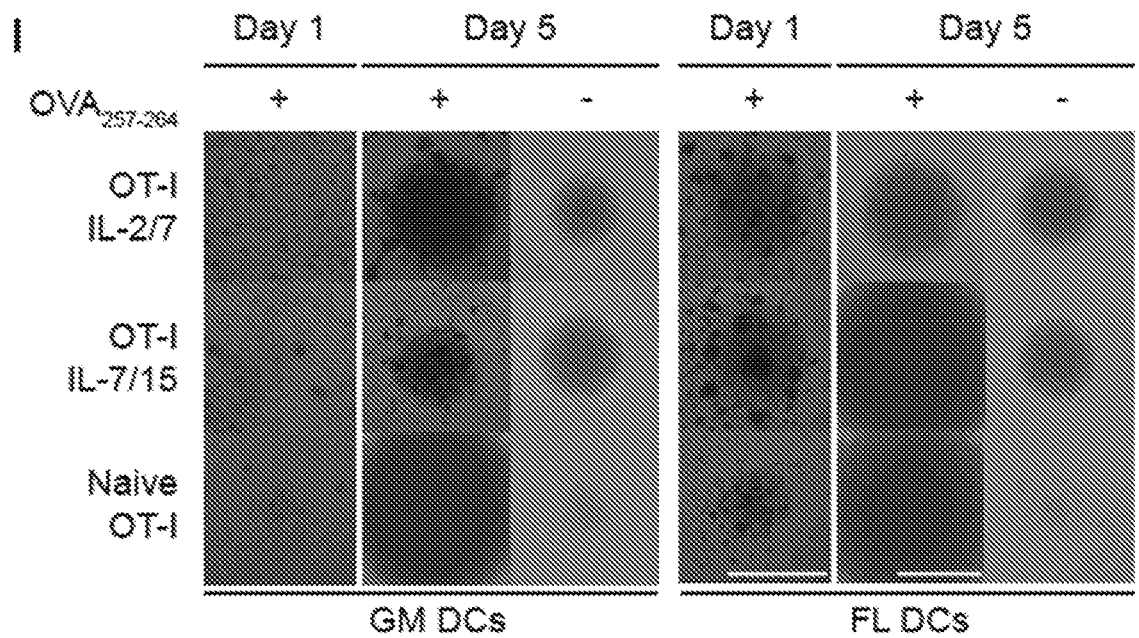
Figure 7:
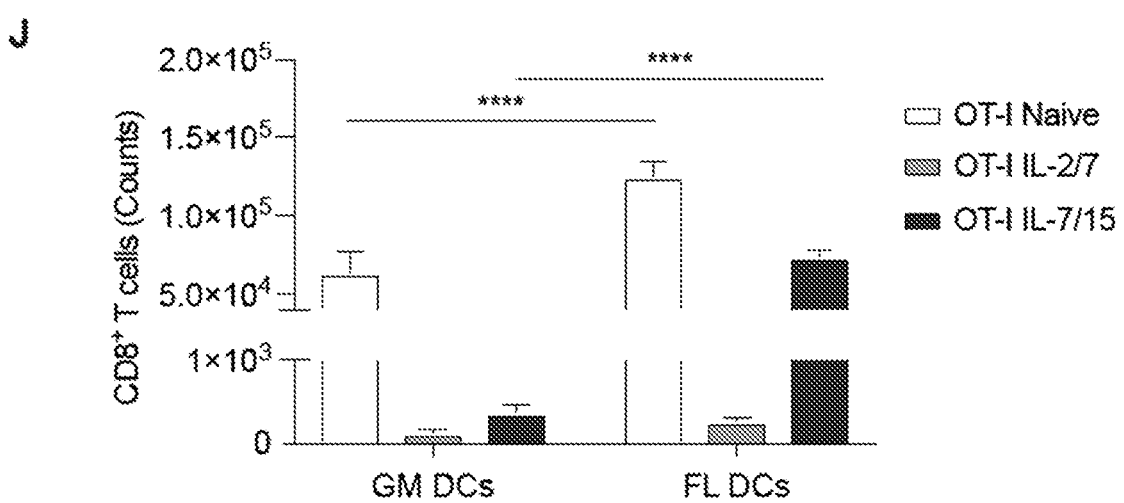

FIG. 7 shows that FLT3L-expressing T cells induce the differentiation of $CD103^+$ DCs which induce superior T cell expansion in vitro. (A) A schematic representation of a FLT3L NGFR (NGFR FL) plasmid vector used to transduce T cells; (B) A schematic representation of transduction of murine C57BL/6 splenocytes with NGFR FL; (C) A graphical representation of secreted FLT3L (ng/mL; y-axis) in the supernatants of transduced T cells at day 7 post-activation; (D-F) A graphical representation of (D) $CD11c^+$ $MHCII^+$ DCs (counts; y-axis) and (E and F) $CD103^+$ DCs (counts; y-axis) at day 7 post-isolation from the bone marrow; (G) A graphical representation of expression of CD44 (y-axis) and CD62L (x-axis) on pre-conditioned OT-I T cells and naïve OT-I T cells; (H) A graphical representation of expression of CD62L (x-axis) and CD44 (y-axis) following co-culture of pre-conditioned OT-I T cells with in vitro differentiated OVA257-264 SIINFEKL peptide pulsed GM DCs (no FLT3L supplementation) or FL DCs (with FLT3L supplementation) at day 5 post-activation; (I) A photographic representation of T cell proliferation following co-culture of pre-conditioned OT-I T cells with in vitro differentiated OVA257-264 SIINFEKL peptide pulsed GM DCs (no FLT3L supplementation) or FL DCs (with FTL3L supplementation); and (J) A graphical representation of absolute number of OT-I T cells (counts; y-axis). Data is shown as mean±SEM of n=3, n.s. not significant, *p<0.05, p<0.01, **p<0.0001 (C-E and J, one-way ANOVA).

Figure 8:
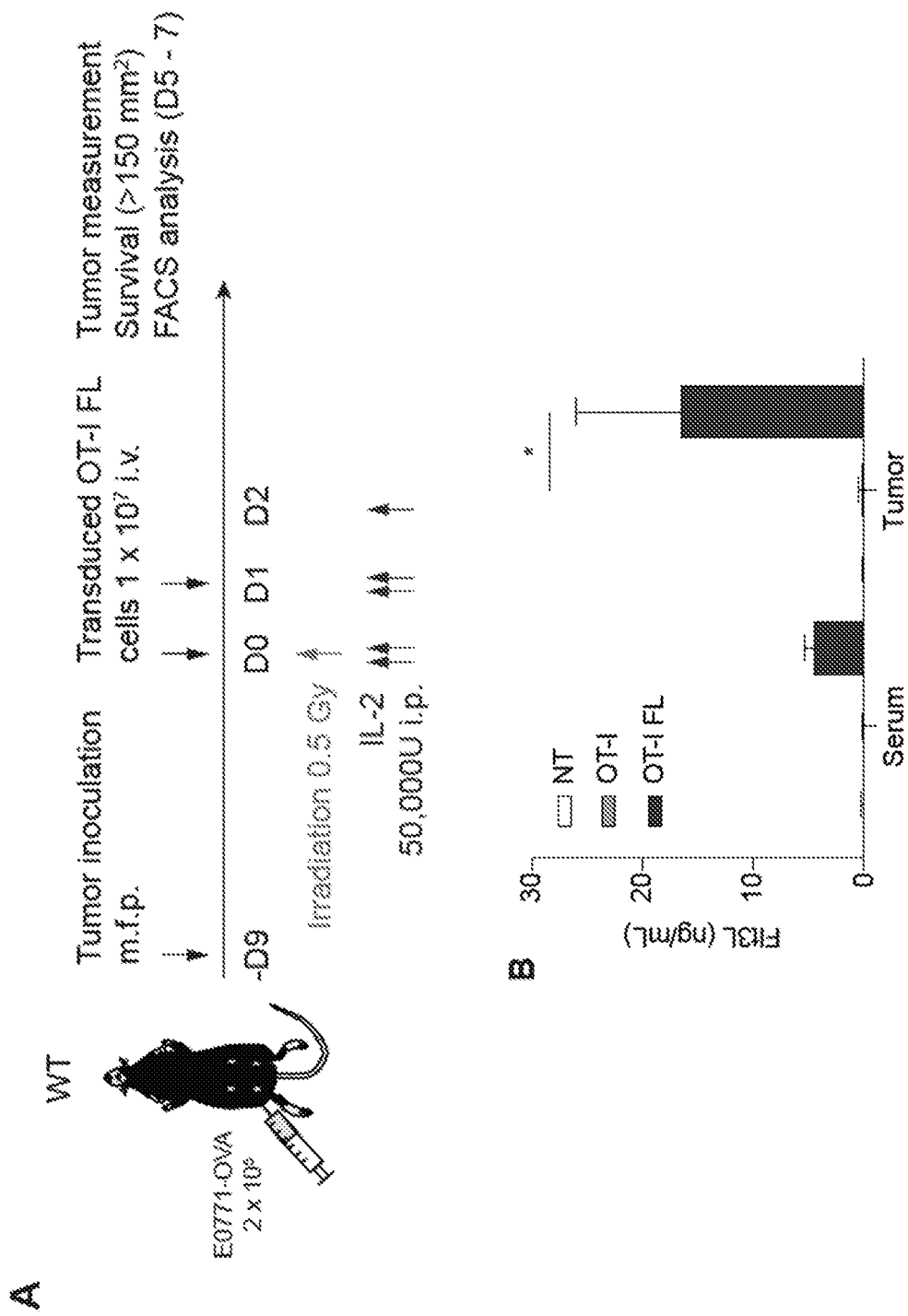
Figure 8:
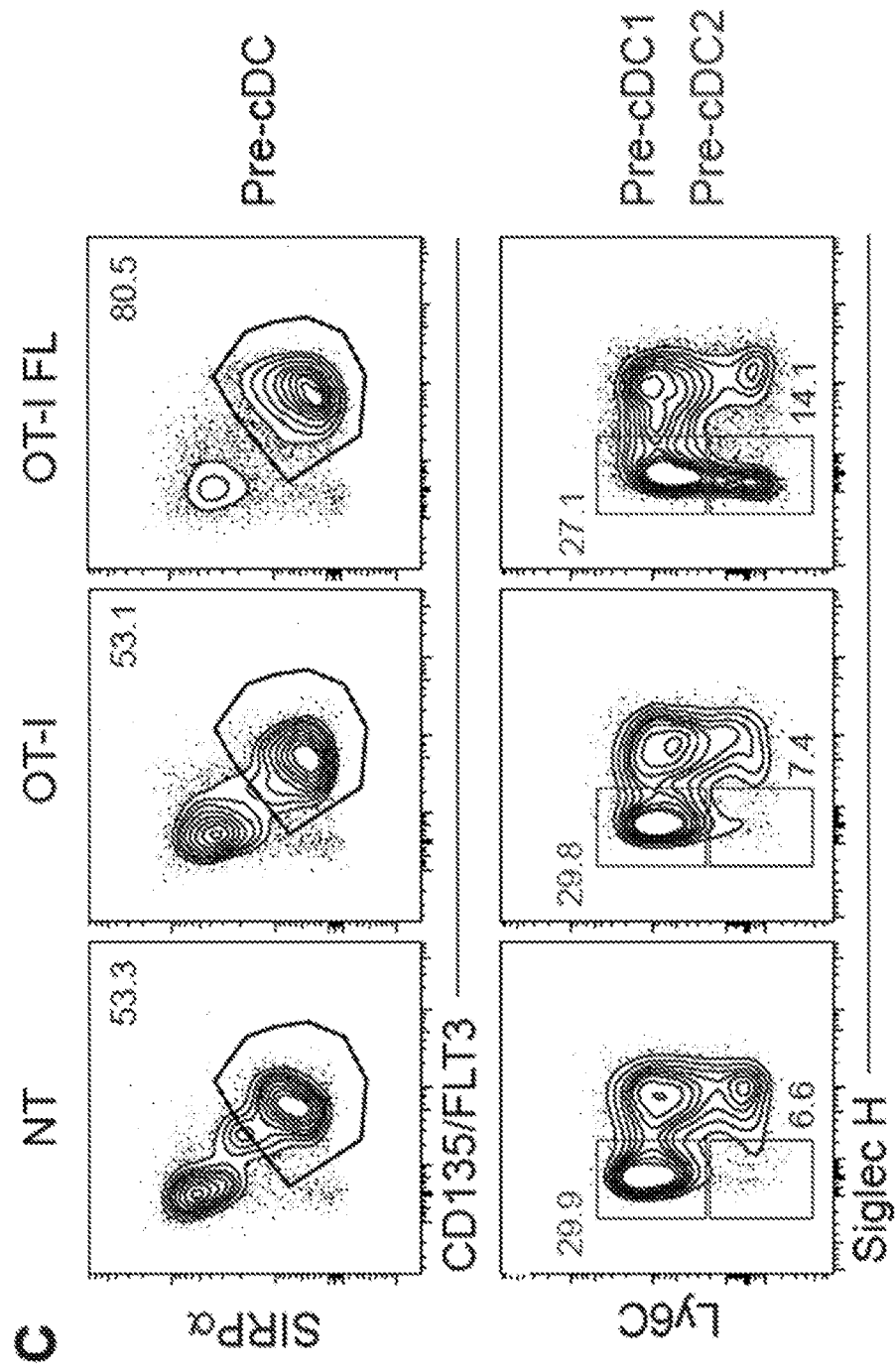
Figure 8:
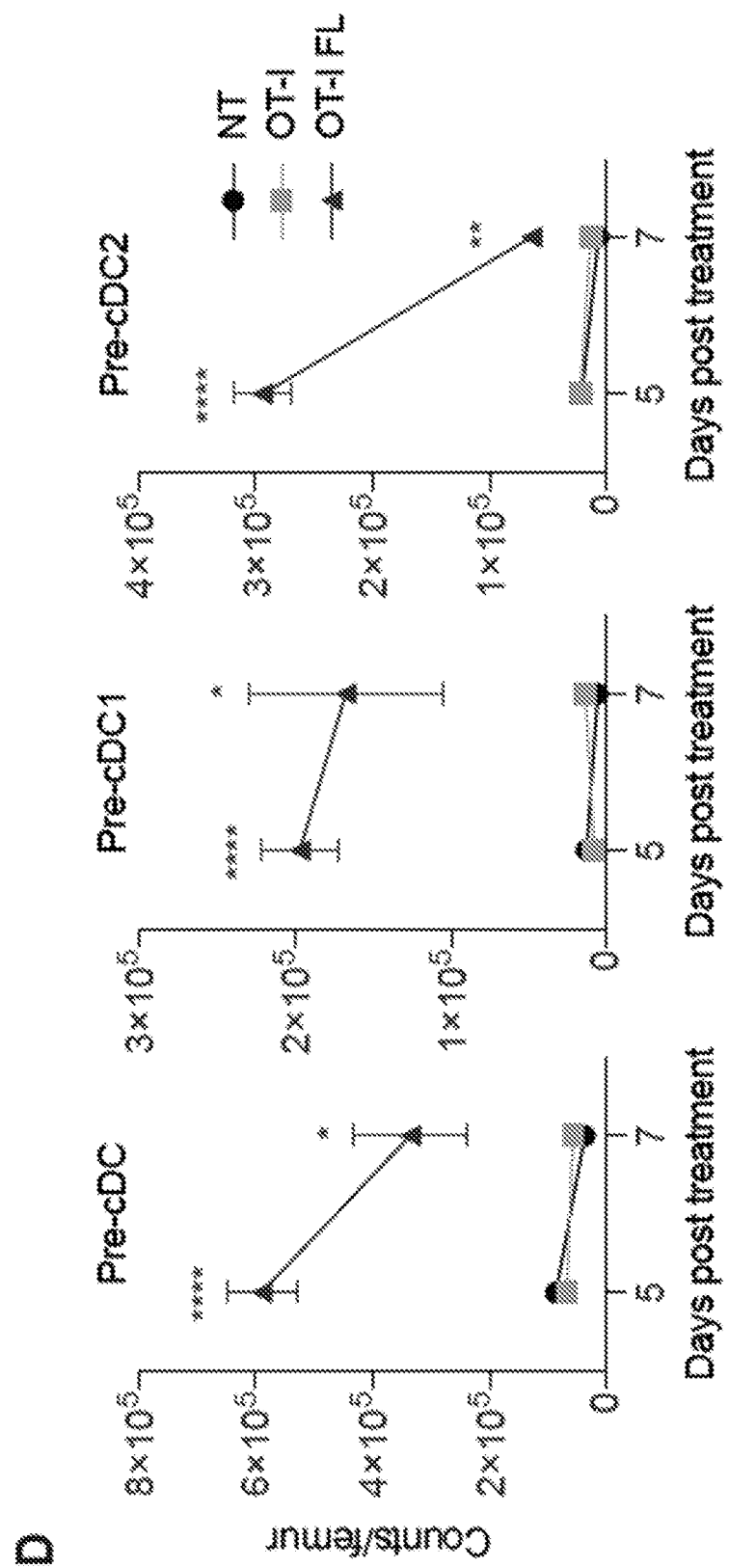
Figure 8:
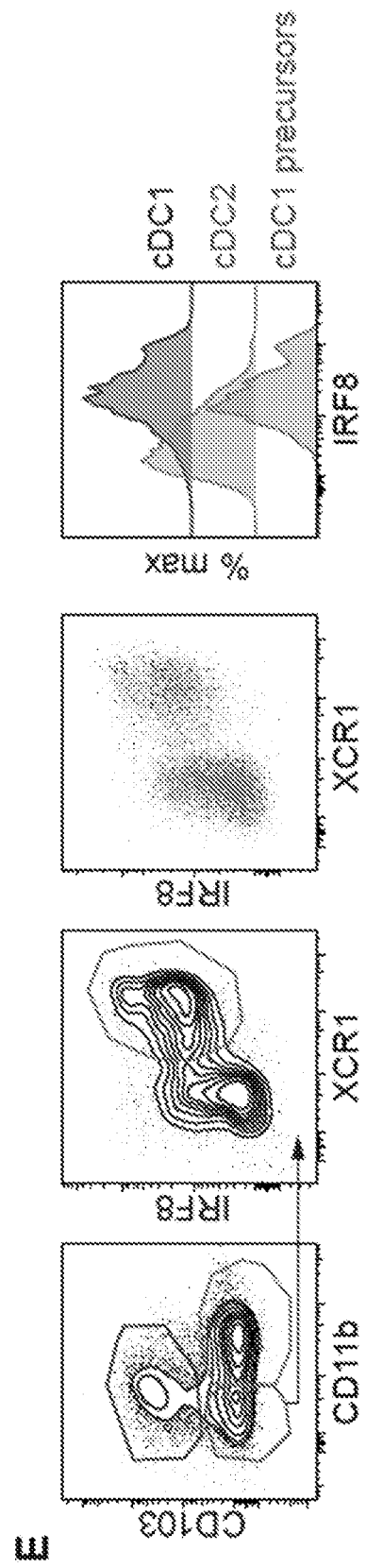
Figure 8:
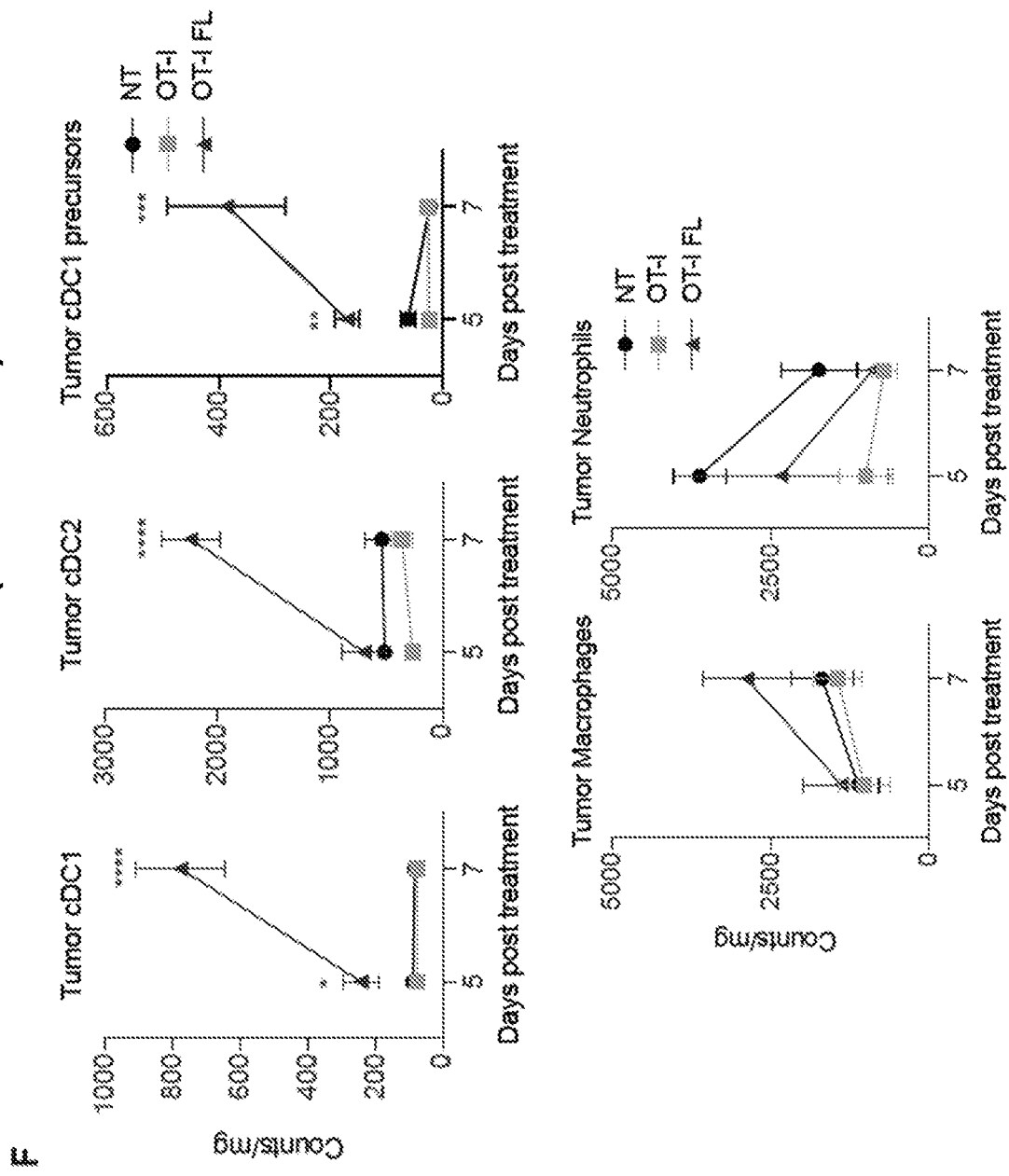
Figure 8:
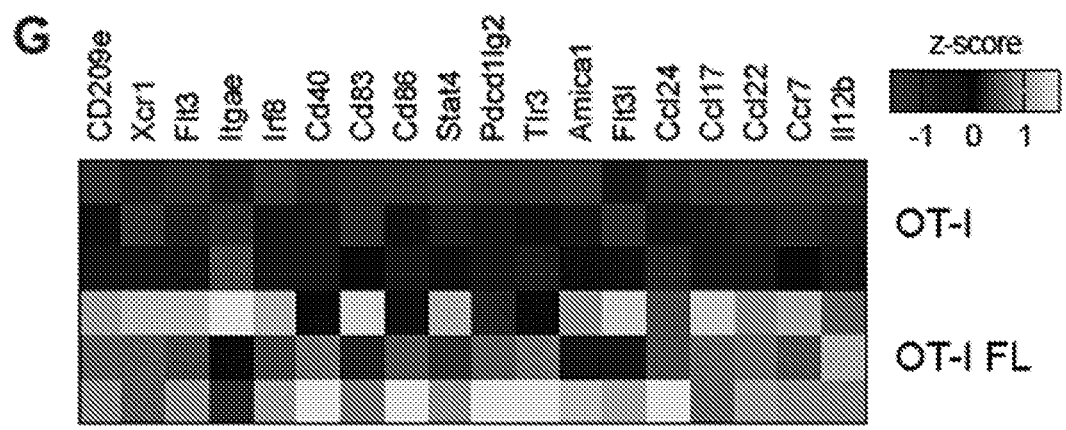
Figure 8:
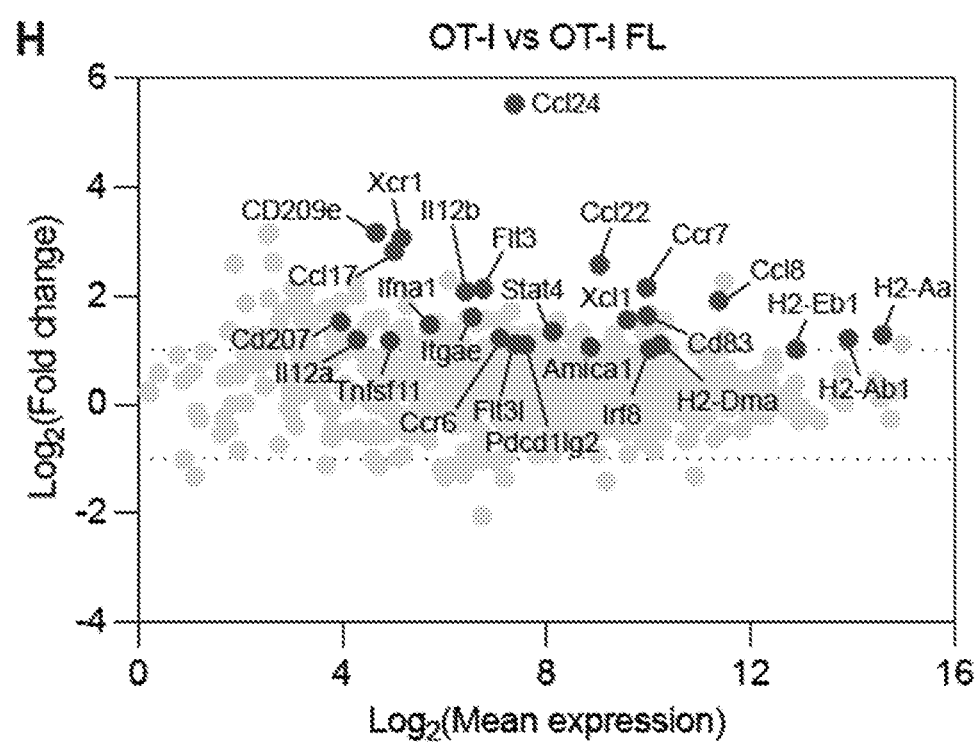
Figure 8:
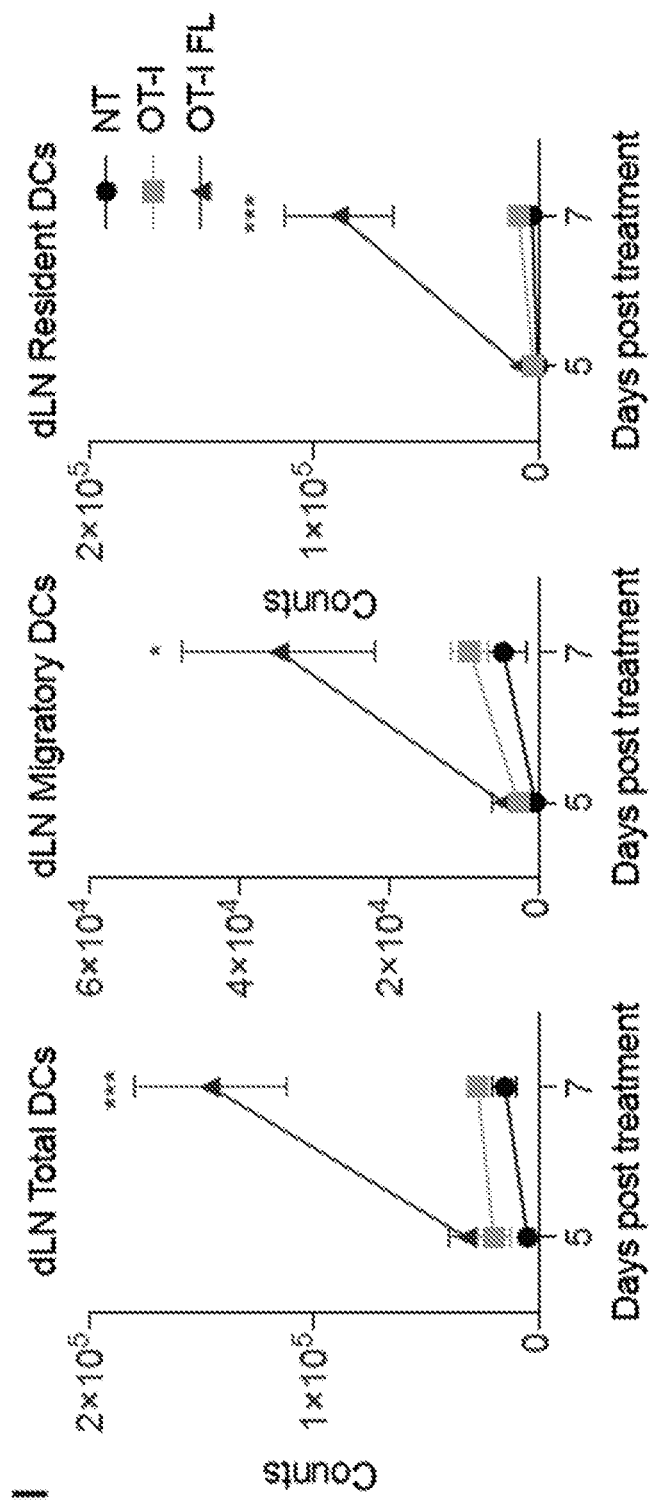

FIG. 8 shows that adoptive transfer of FLT3L-secreting T cells expands CD103+ cDCs. (A) A schematic representation of OT-I adoptive transfer and treatment of E0771-OVA tumour model; (B) A graphical representation of FLT3L expression (ng/mL; y-axis) in the tumours and blood sera of wild-type mice inoculated with E0771-OVA tumour cells; (C) A graphical representation of the proportion of DC precursors (pre-cDC) in the bone marrow at day 7 post-treatment; (D) A graphical representation of the proportion of pre-cDC in the bone marrow (counts per femur; y-axis) against time (days post-treatment; x-axis) measured at day 5 or day 7 post-treatment; (E) A graphical representation of the gating strategy for conventional DC type I (cDC1), type 2 (cDC2) and cDC1 precursors in the tumour; (F) A graphical representation of absolute numbers of cDC1, cDC2 and cDC1 precursors and other myeloid cell subsets in the tumour (counts per mg of tumour tissue; y-axis) against time (days post-treatment; x-axis) measured at day 5 and day 7 post-treatment; (G) Heat map of differentially expressed DC related genes following treatment with OT-I or OT-I FLT3L T cells; (H) A graphical representation of fold change in expression ($Log_2$(fold change); y-axis) against mean expression ($Log_2$(mean expression); x-axis); and (I) A graphical representation of absolute numbers of DC subsets in the tumour dLN (counts; y-axis) against time (days post-treatment; x-axis). Data is shown as mean±SEM of n=3-12 mice per group of two pooled independent experiments, *p<0.05, p<0.01, *p<0.001, ****p<0.0001 (one-way ANOVA).

Figure 9:
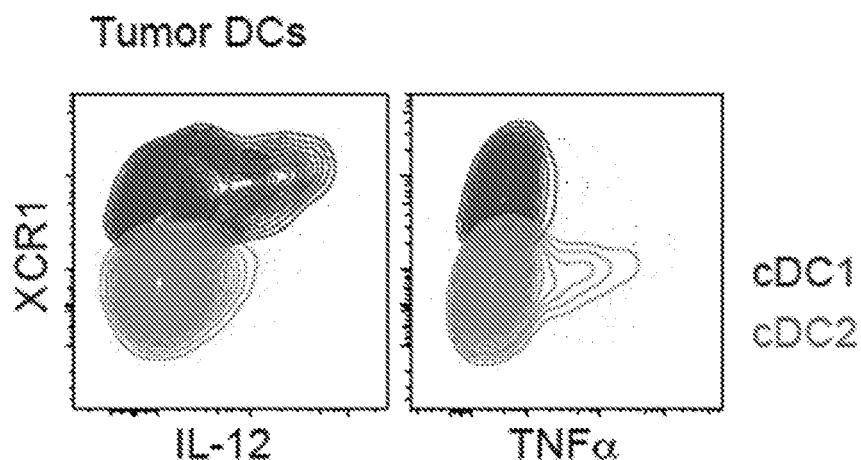
Figure 9:
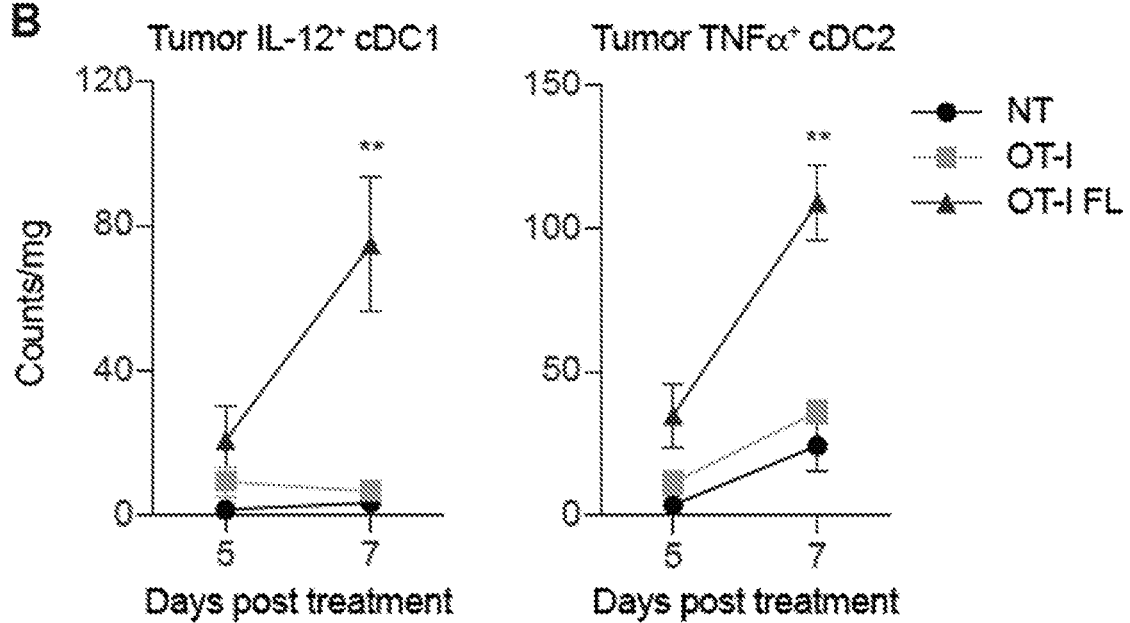
Figure 9:
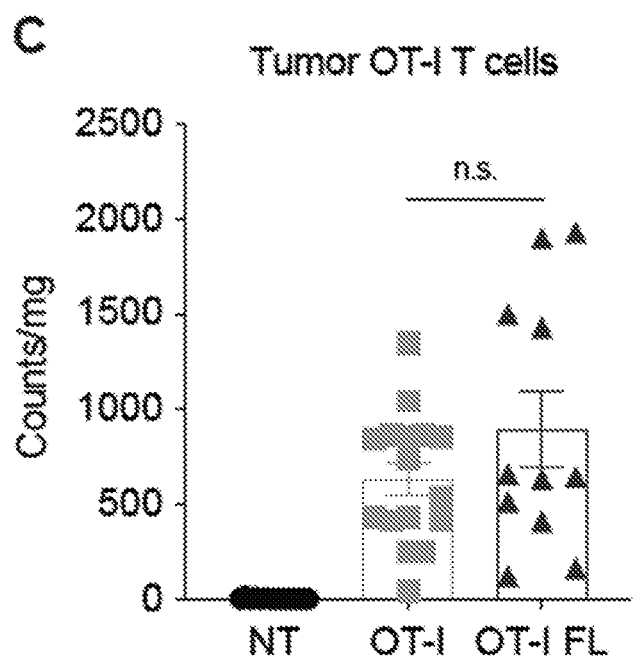
Figure 9:
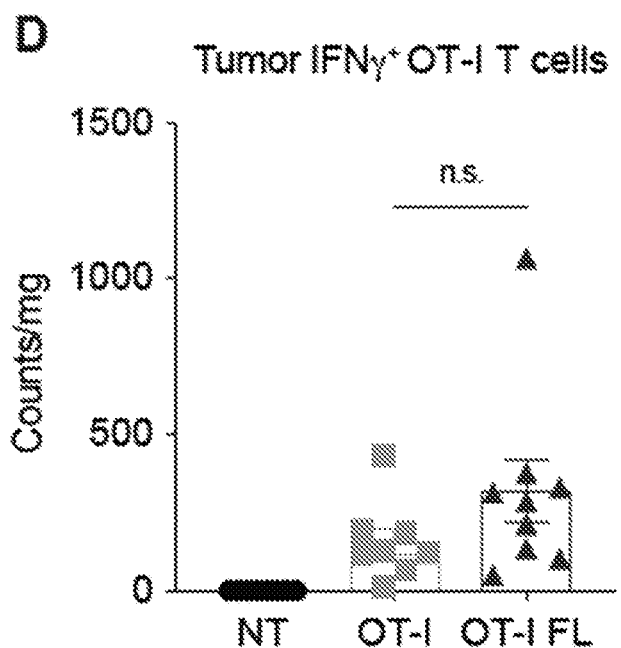
Figure 9:
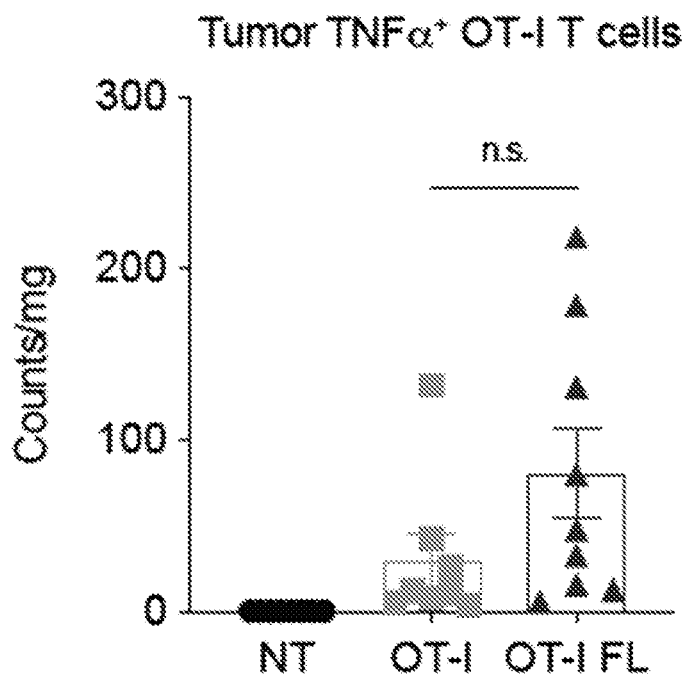
Figure 9:
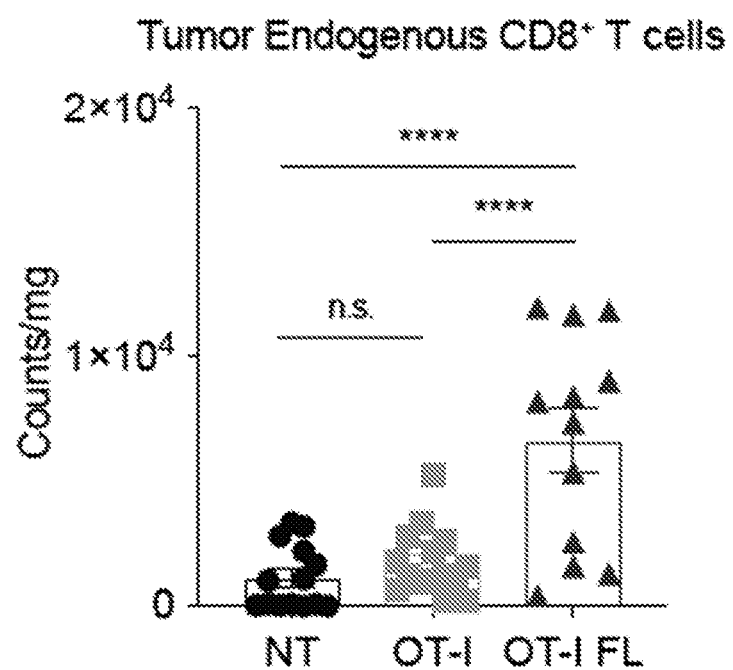
Figure 9:
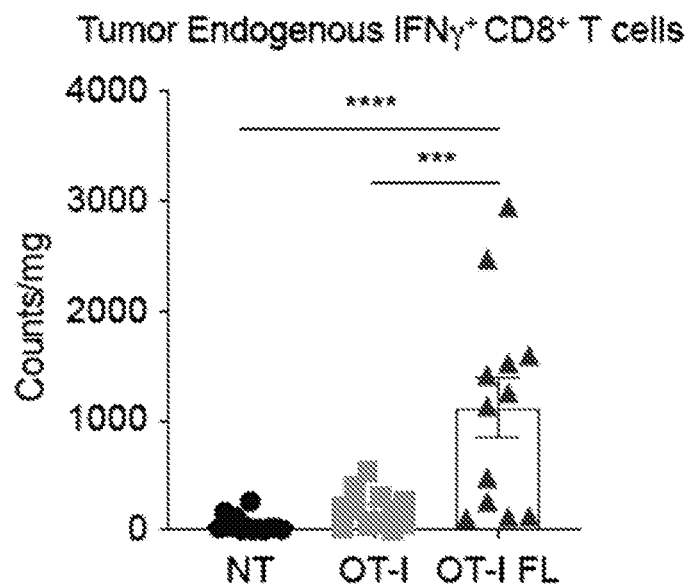
Figure 9:
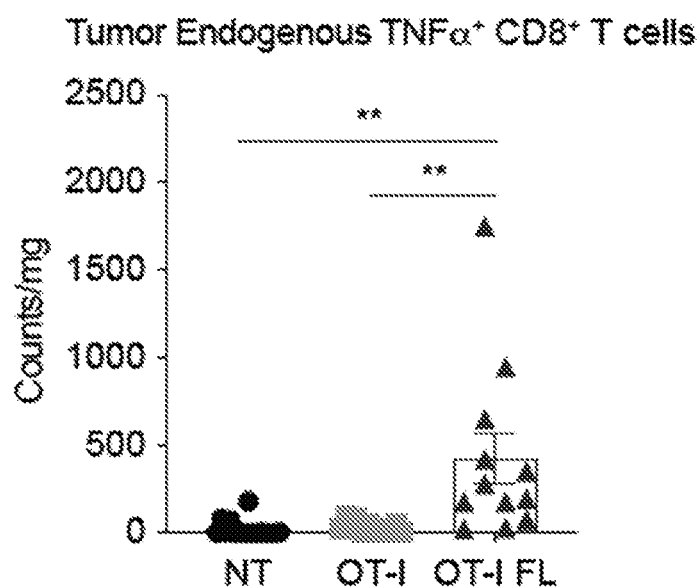
Figure 9:
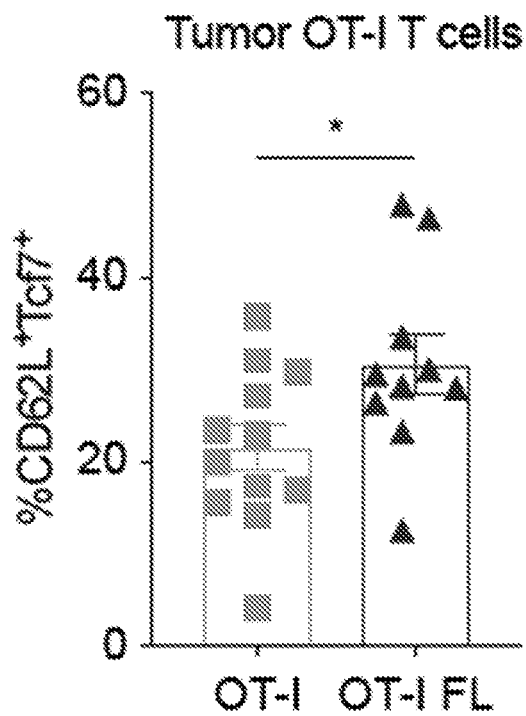
Figure 9:
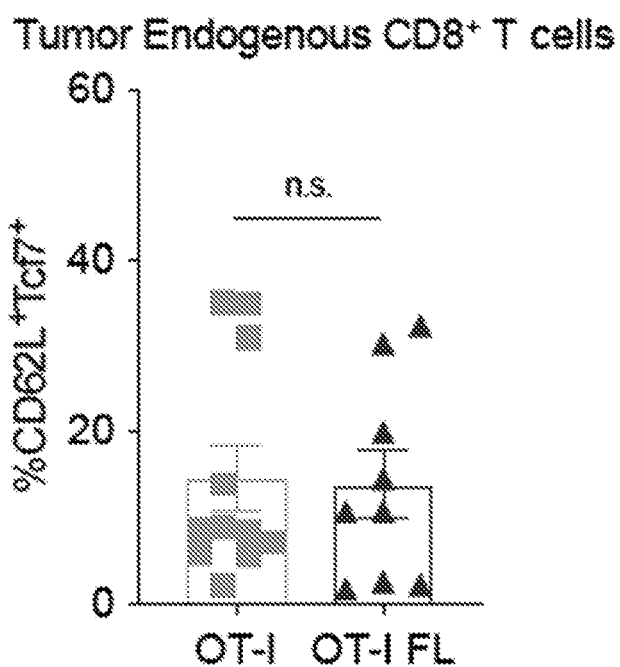
Figure 9:
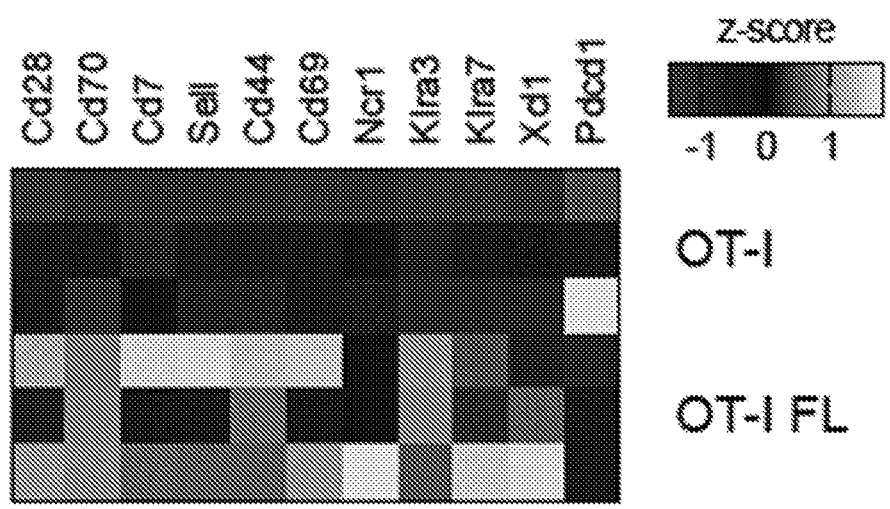

FIG. 9 shows that DC expansion enhances infiltration of functional host $CD8^+$ T cells at the tumour site. (A) A graphical representation of expression of IL-12 and TNFα (x-axis) by cDC1s and cDC2s; (B) A graphical representation of absolute number of IL-12 secreting cDC1 and TNFα secreting cDC2 in tumours (counts per mg of tumour; y-axis) against time (days post-treatment; x-axis); (C-E) A graphical representation of absolute numbers of tumour (C) OT-I T cells, (D) OT-I T cells, and (E) $TNFα^+$ OT-I T cells (counts per mg or tumour; y-axis); (F-H) A graphical representation of absolute numbers of tumour endogenous (F) $CD8^+$ T cells, (G) $CD8^+$ T cells, and (H) $TNFα^+$ $CD8^+$ T cells; (I-J) A graphical representation of the proportion of (I) adoptively transferred OT-I T cells and (J) endogenous $CD8^+$ T cells expressing a $CD62L^+$ $Tcf7^+$ phenotype (%; y-axis); (K) Heat map of differentially expressed T and NK cell related genes between OT-I and OT-I FL tumours. Data is shown as mean±SEM of n=3-12 mice per group of two pooled independent experiments, n. s. not significant, *p<0.05, p<0.01, *p<0.001, ****p<0.0001 (one-way ANOVA).

Figure 10:
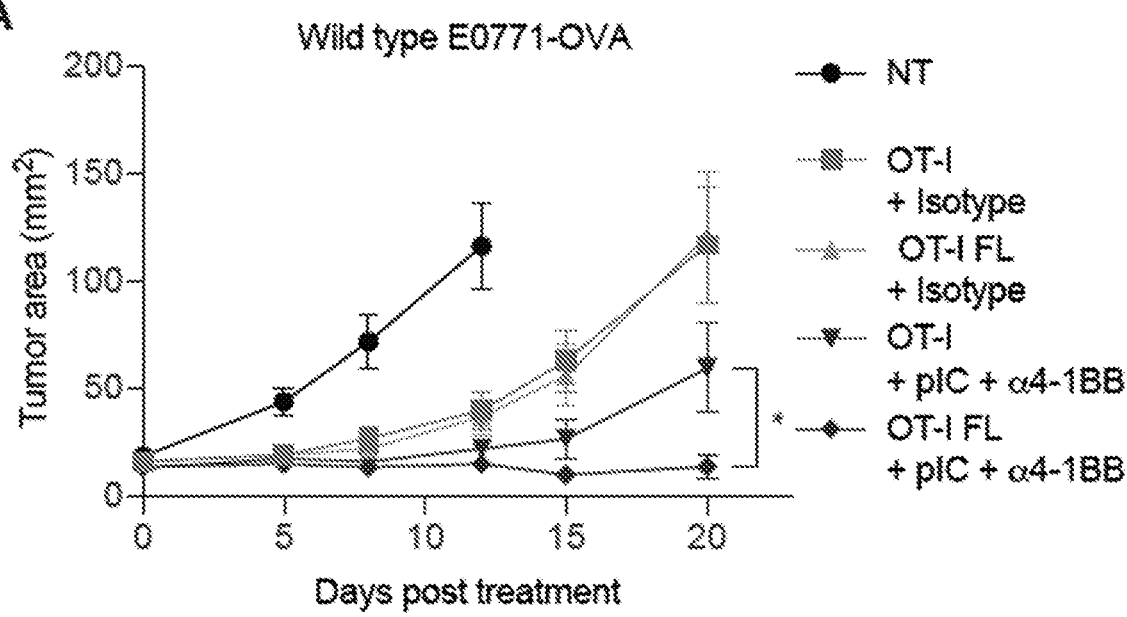
Figure 10:
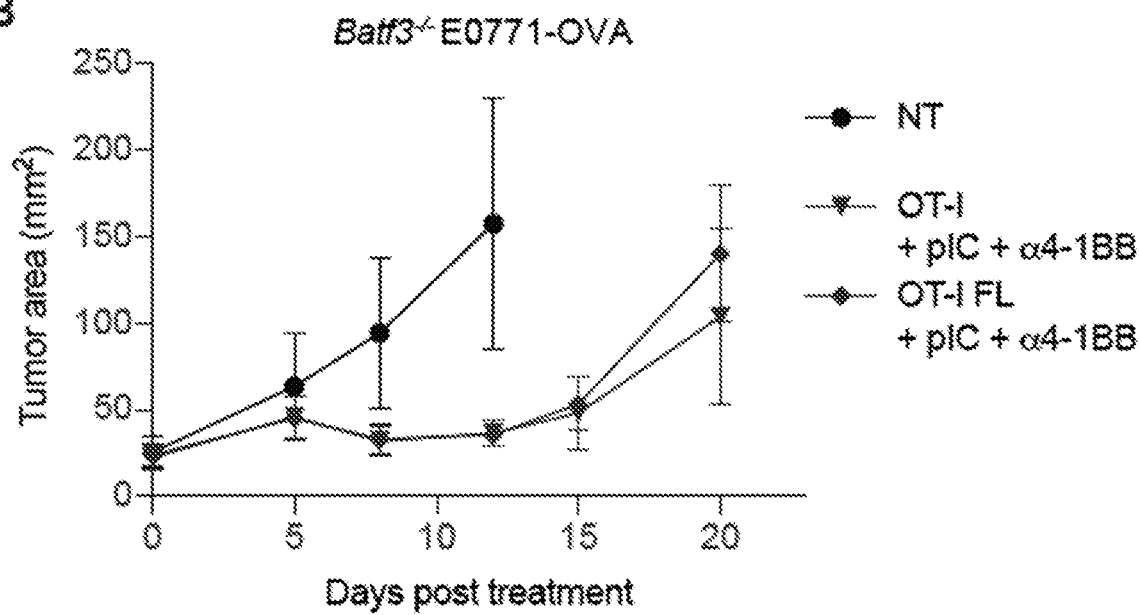
Figure 10:
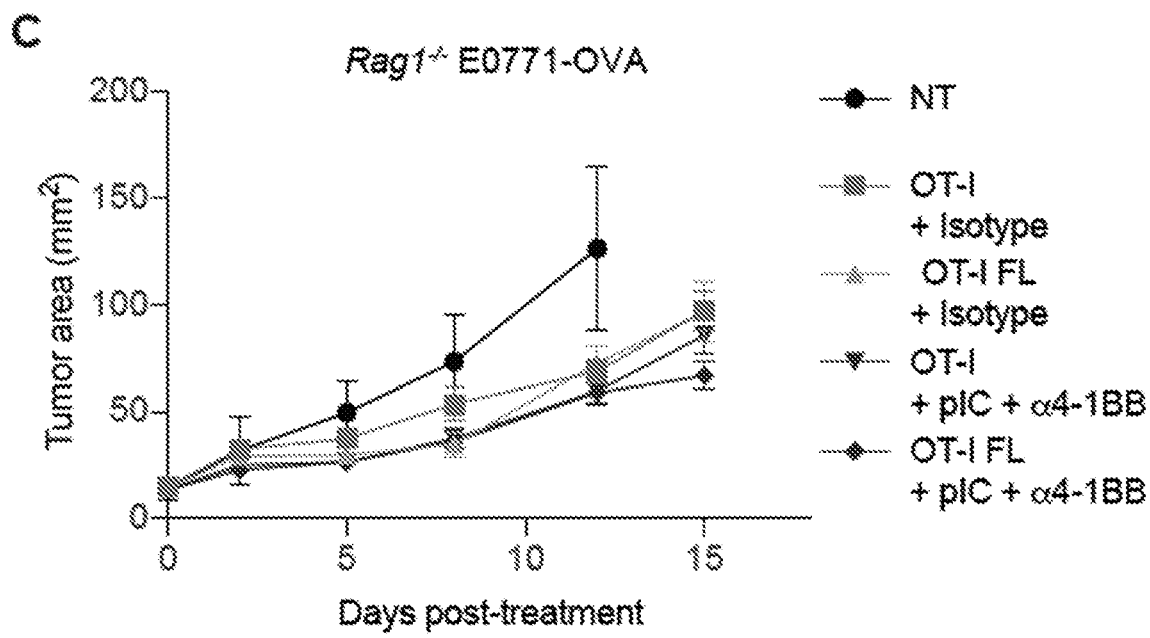
Figure 10:
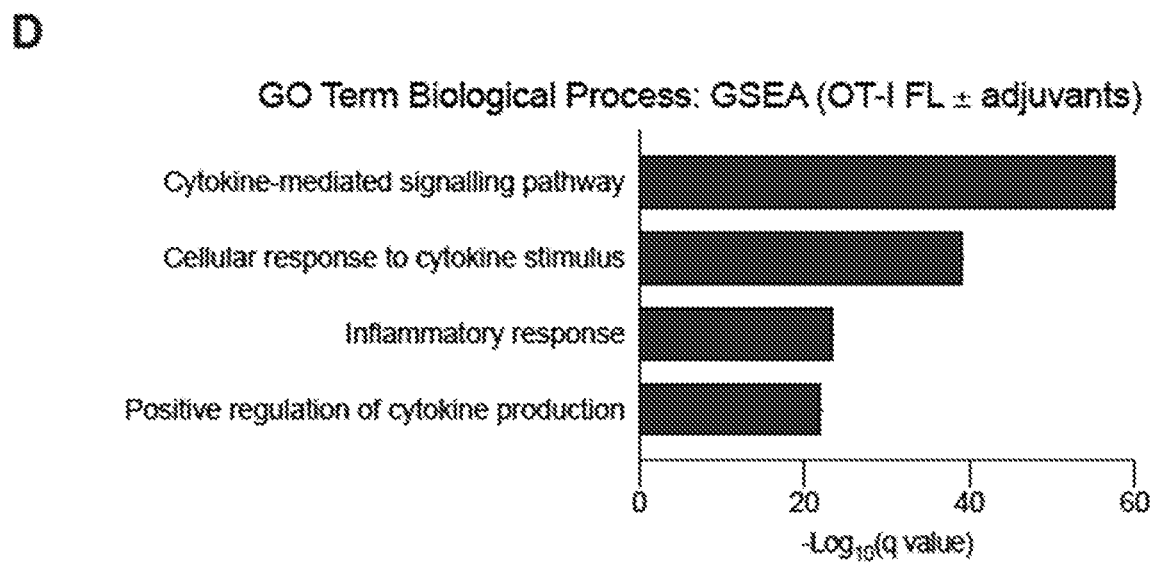
Figure 10:
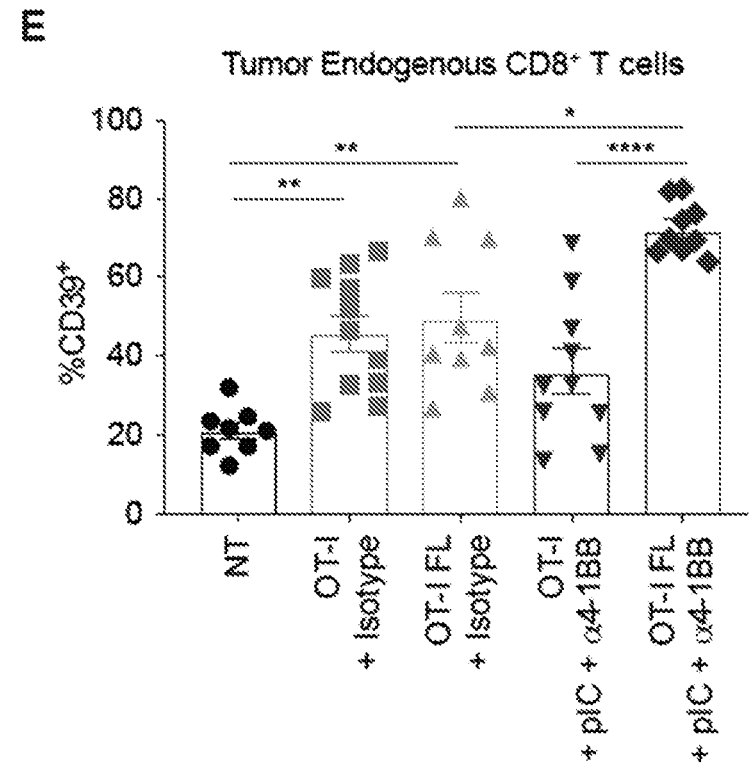
Figure 10:
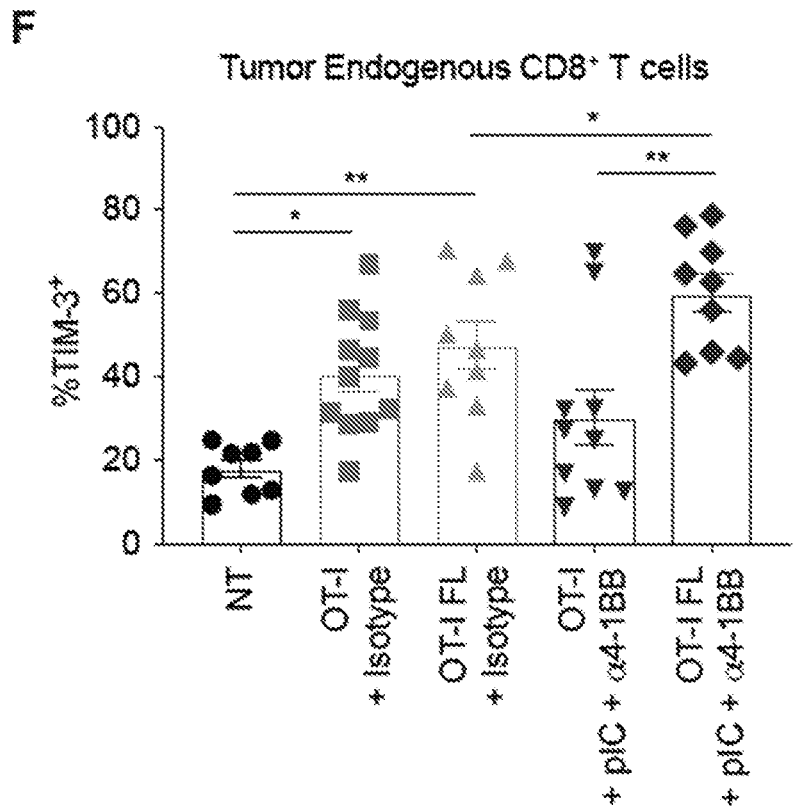
Figure 10:
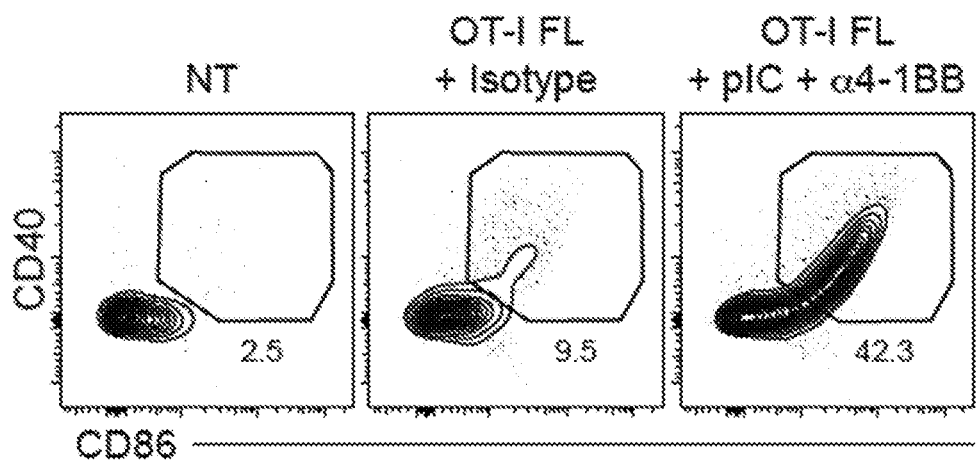
Figure 10:
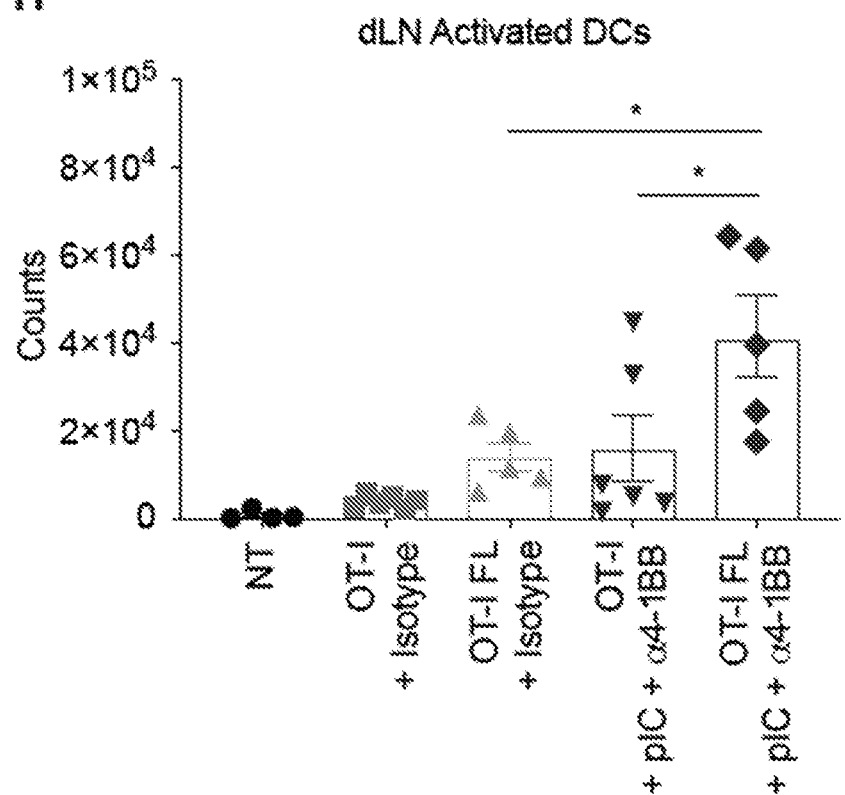
Figure 10:
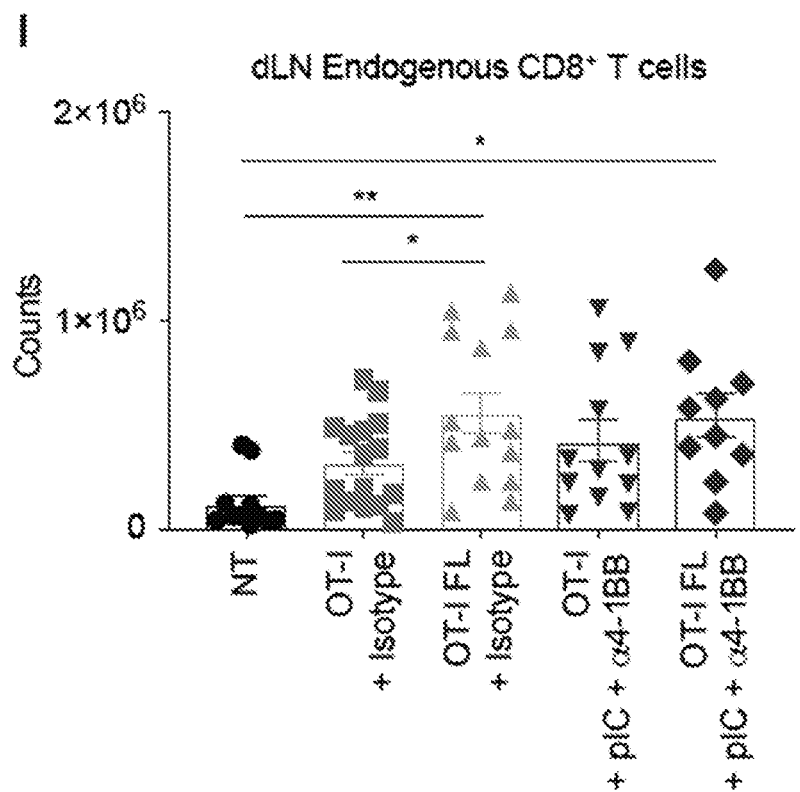
Figure 10:
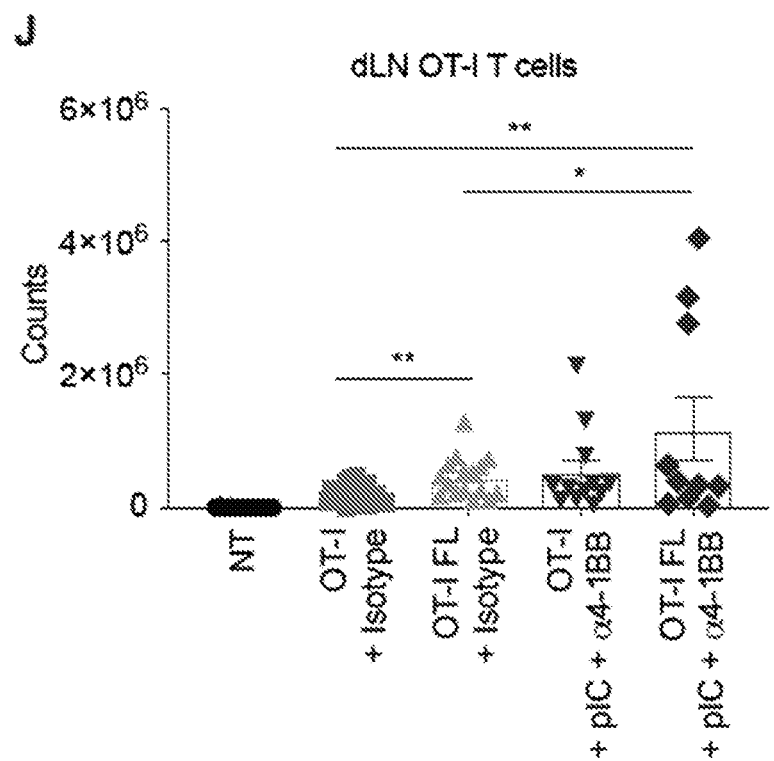

FIG. 10 shows that the combination of FLT3L secreting T cells with immune stimulatory adjuvants inhibits tumour growth associated with increased activation of host T cells. (A-C) A graphical representation of tumour area ($mm^2$; y-axis) in (A) wild type, (B) $Batf3^{-/-}$, or (C) $Rag1^{-/-}$ mice inoculated with $2×10^5$ E0771 OVA cells and treated with transduced OT-I T cells with immune adjuvants pIC (100 µg/mouse) and agonistic anti-4-1BB antibody (100 µg/mouse) against time (days post-treatment; x-axis) measured on days 5 and 8 post-treatment; (D) A graphical representation of gene ontology (GO) biological process gene set enrichment analysis (GSEA) of significantly differentially expressed genes between tumours of mice treated with FLT3L-secreting OT-I T cells with or without adjuvant therapy; (E-F) A graphical representation of the proportion of endogenous $CD8^+$ T cells expressing (E) CD39 and (F) TIM-3 (%; y-axis); (G) A graphical representation of CD40 (y-axis) and CD86 (x-axis) expression on DCs following treatment with OT-I FL with or without adjuvant therapy; (H-J) A graphical representation of the absolute number of (H) activated DCs, (I) host $CD8^+$ and (J) transferred OT-I T cells within tumour draining lymph nodes of mice receiving combination therapy (counts; y-axis). Data is shown as mean±SEM of n=3-12 mice per group of two pooled independent experiments, *p<0.05, p<0.01, **p<0.0001 (A-C two-way ANOVA, E-J one-way ANOVA).

Figure 11:
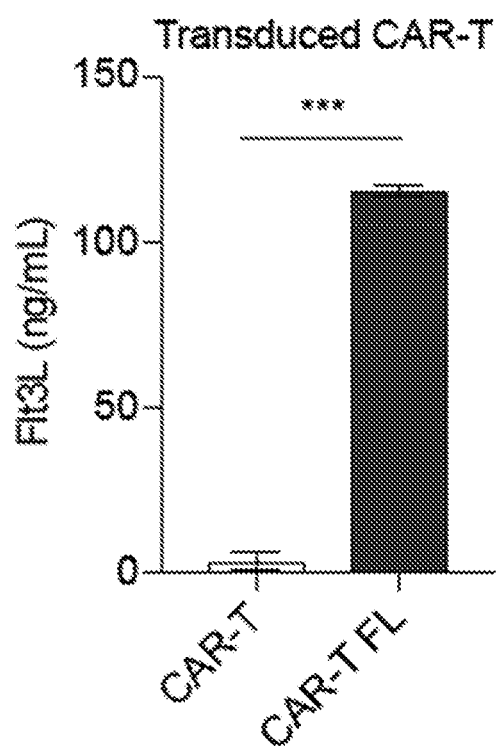
Figure 11:
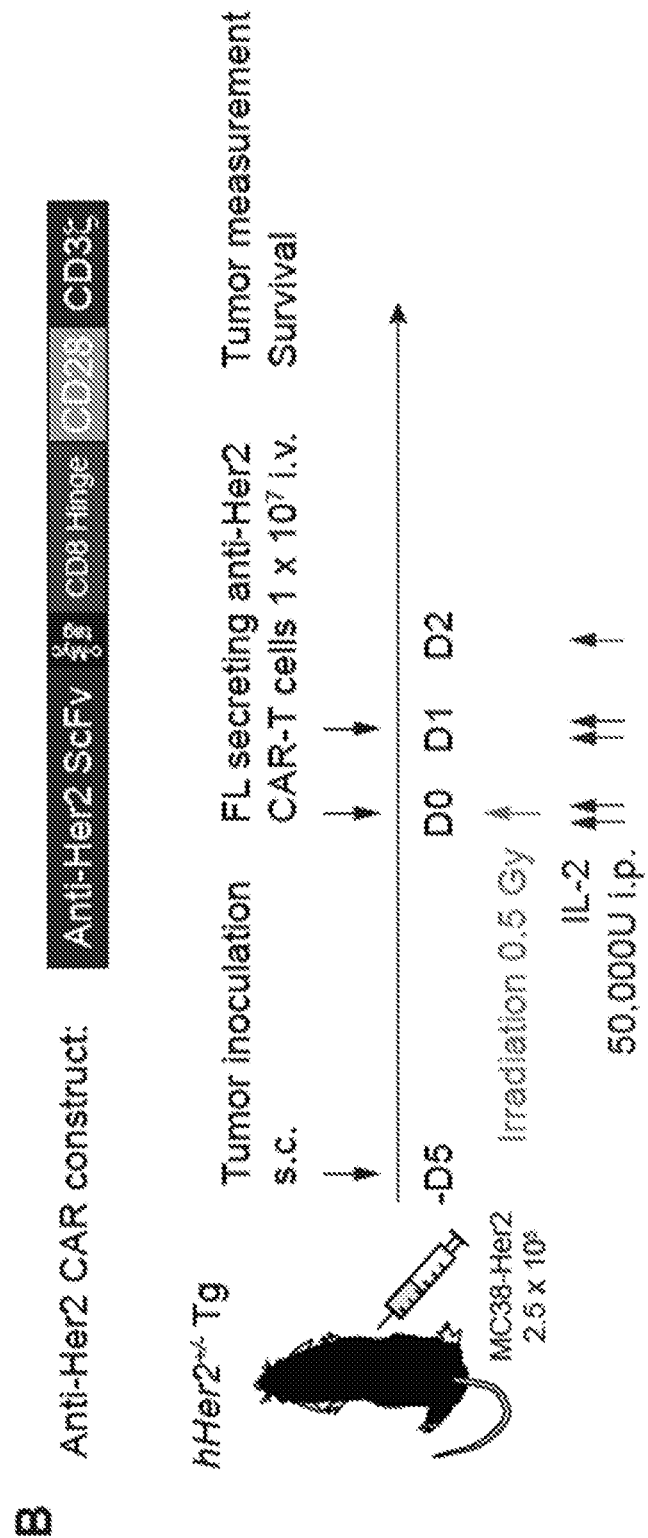
Figure 11:
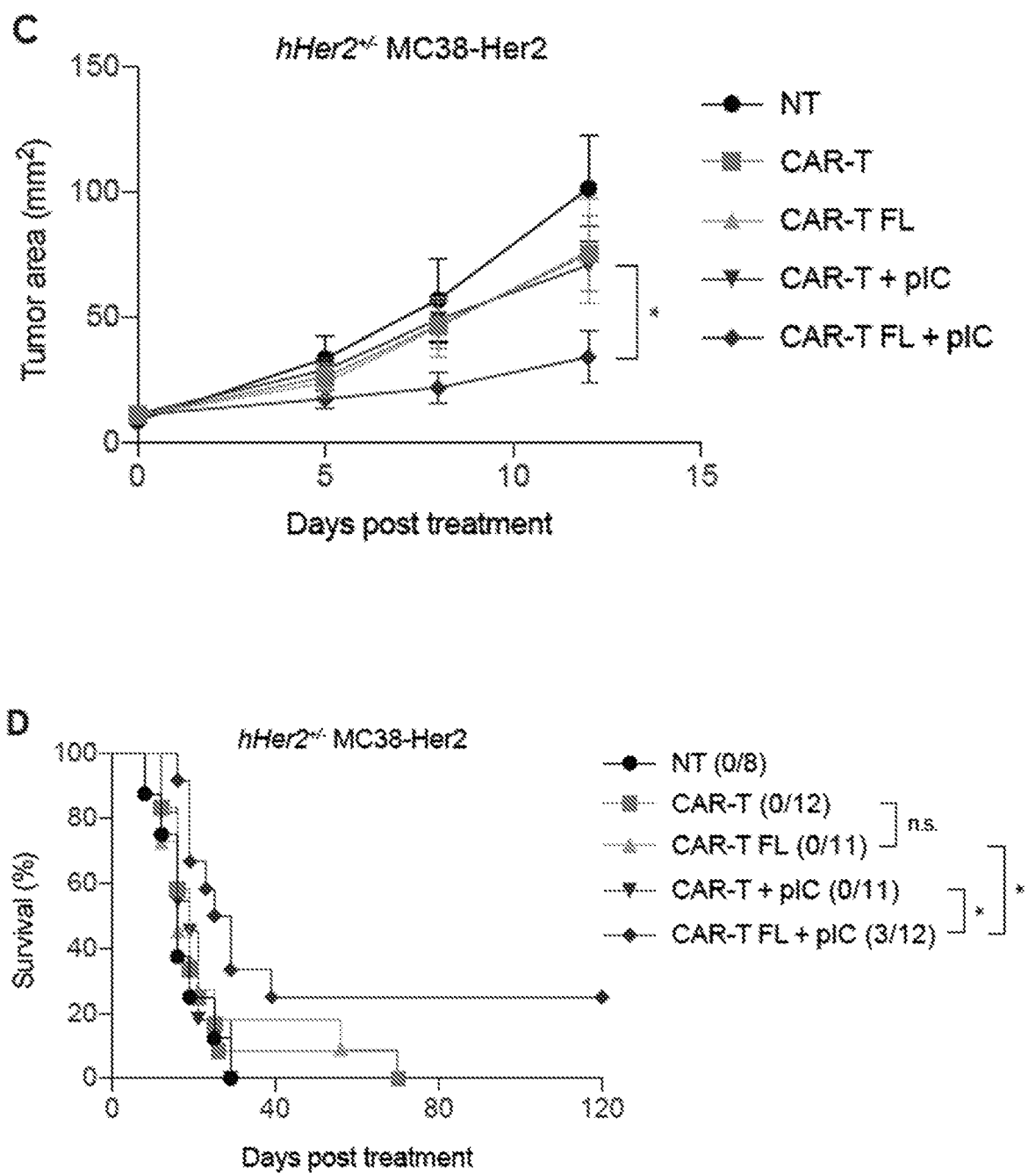
Figure 11:
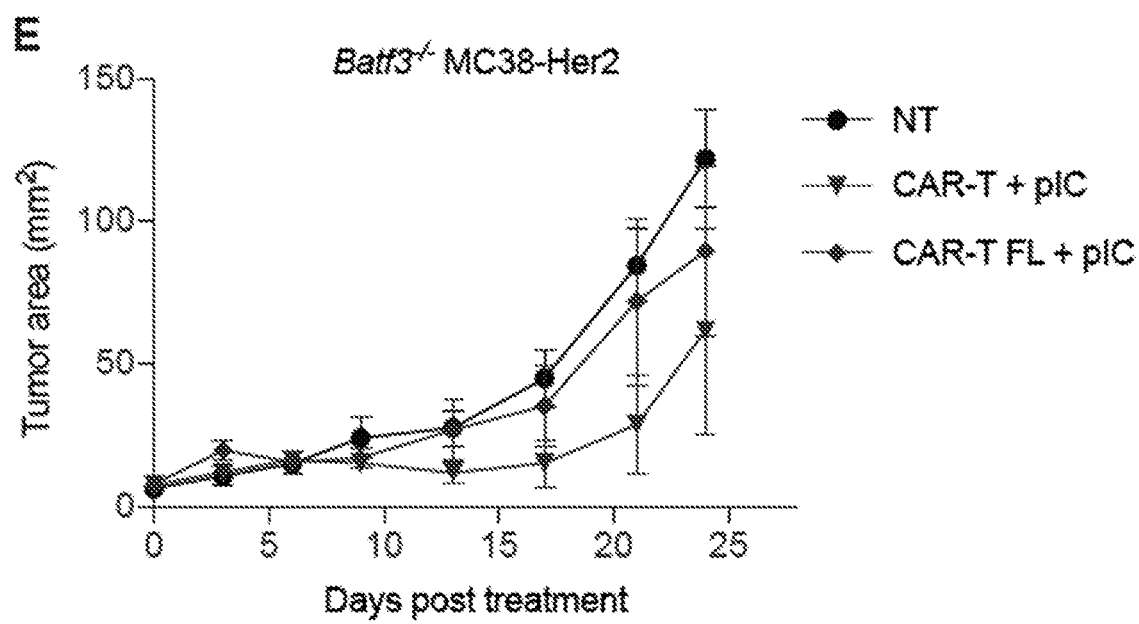
Figure 11:
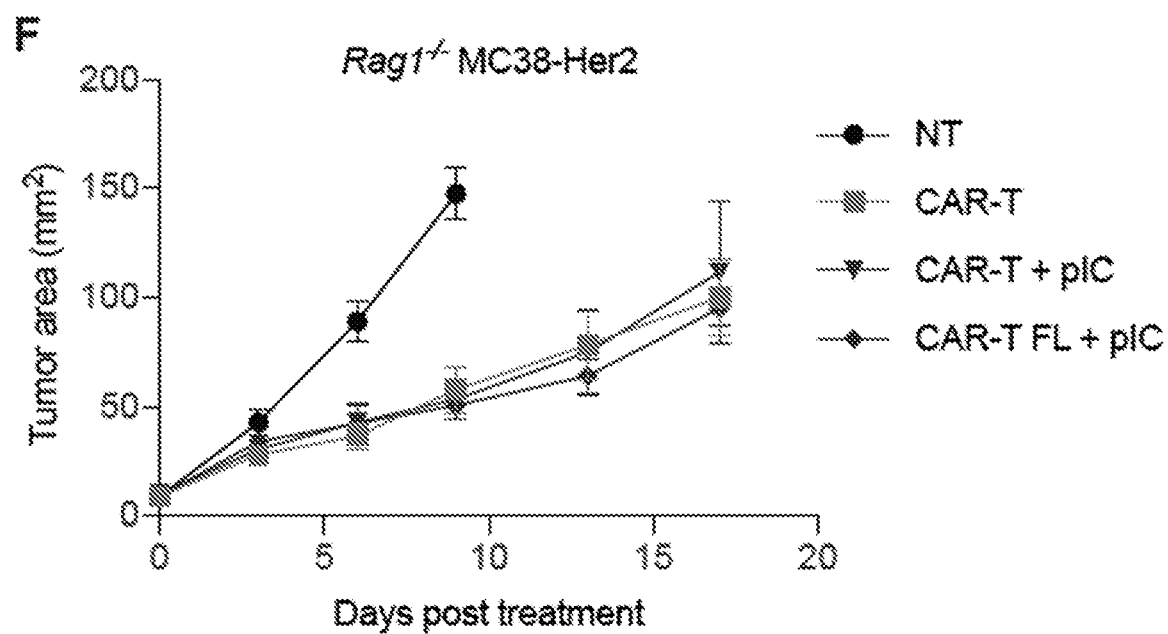

FIG. 11 shows that the combination of FLT3L-secreting CAR T cells and pIC inhibits tumour growth and improves survival. (A) A graphical representation of FLT3L (ng/mL; y-axis) in the supernatants of T cells transduced to express anti-Her2 CAR and FLT3L Cherry (CAR T FL) or control; (B) A schematic representation of CAR T cell adoptive transfer protocol and tumour model; (C) A graphical representation of tumour area ($mm^2$; y-axis) against time (days post-treatment; x-axis) in $hHer2^{+/-}$ MC38-Her2 mice treated with a combination of FLT3L secreting CAR T cells and pIC (100 µg per dose on days 5 and 8 post treatment); (D) A graphical representation of survival (%; y-axis) against time (days post-treatment; x-axis) in $hHer2^{+/-}$ MC38-Her2 mice treated with a combination of FLT3L secreting CAR T cells and pIC (100 µg per dose on days 5 and 8 post treatment); (E-F) A graphical representation of tumour area ($mm^2$; y-axis) against time (days post-treatment; x-axis) in (E) $Batf3^{-/-}$ and (F) $Rag1^{-/-}$ mice treated with a combination of FLT3L secreting CAR T cells and pIC (100 µg per dose on days 5 and 8 post treatment). Data is shown as mean±SEM of n=3-12 mice per group, n.s. not significant, *p<0.05 (C, E and F two-way ANOVA, and D Mantel-Cox test).

Figure 12:
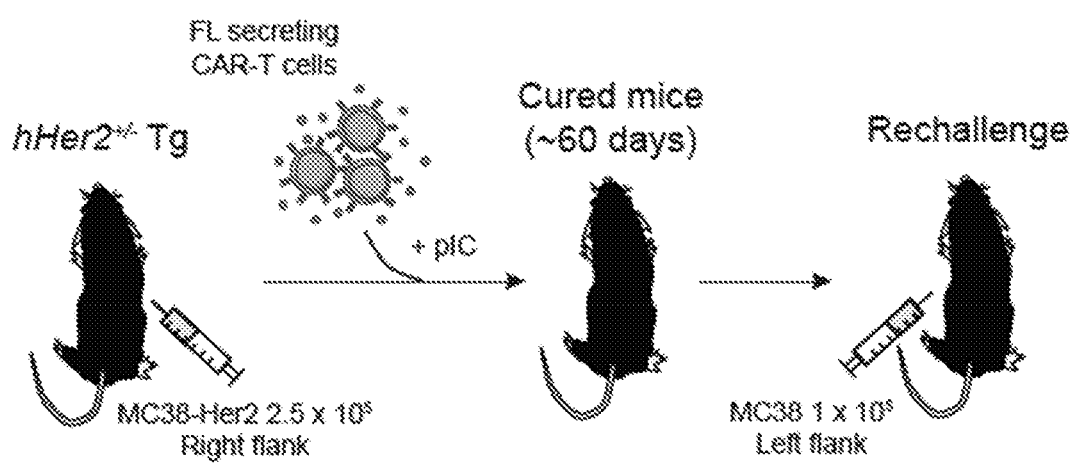
Figure 12:
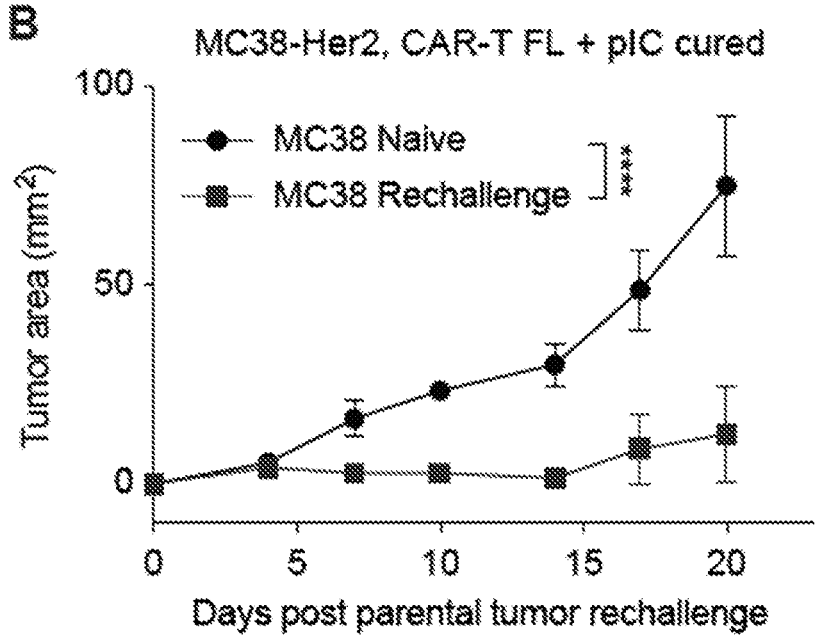
Figure 12:
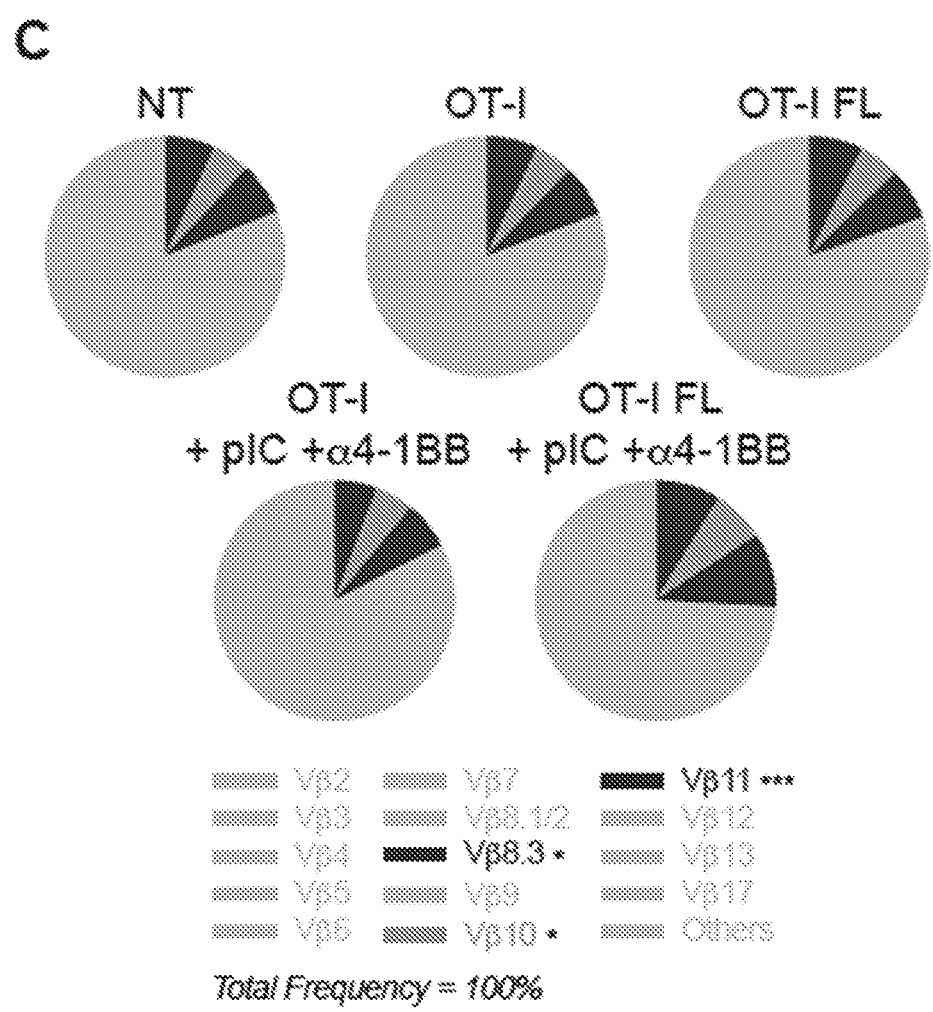
Figure 12:
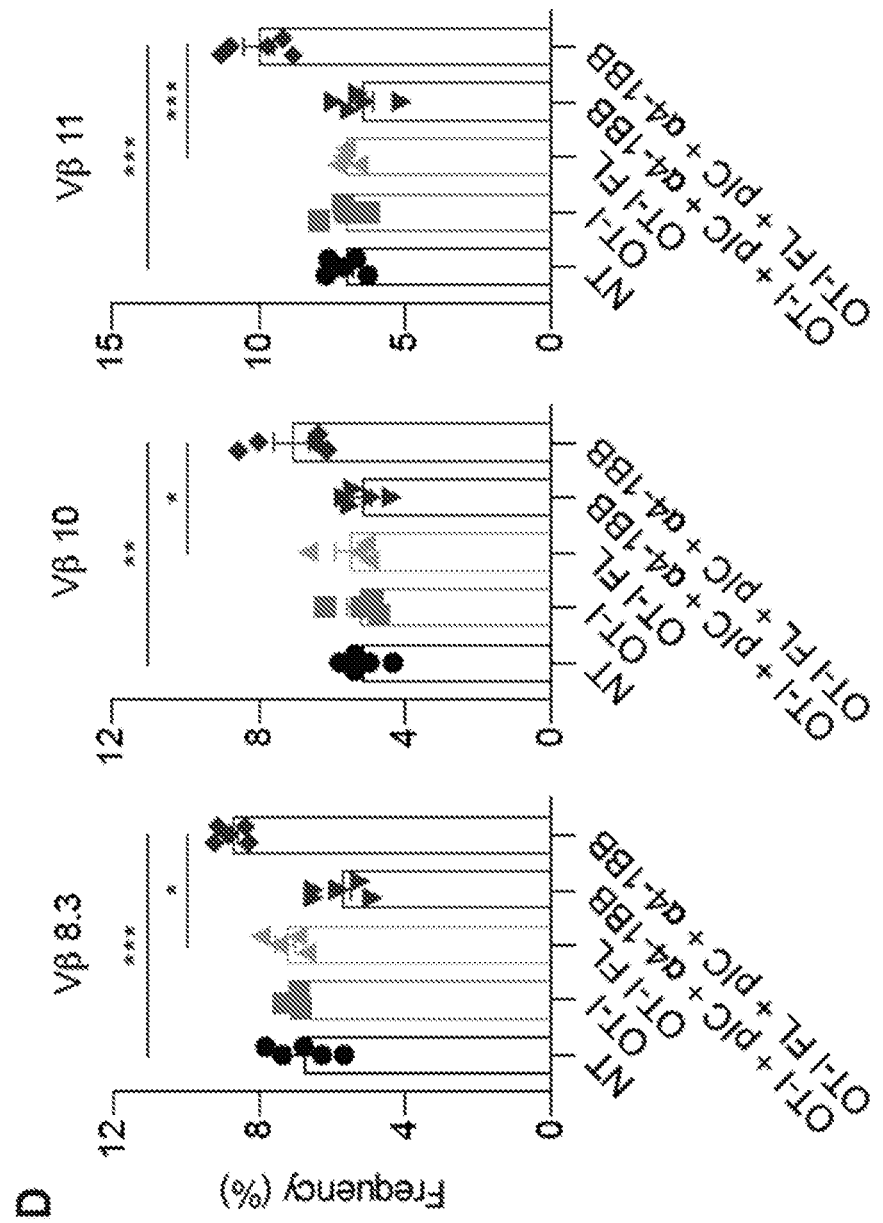
Figure 12:
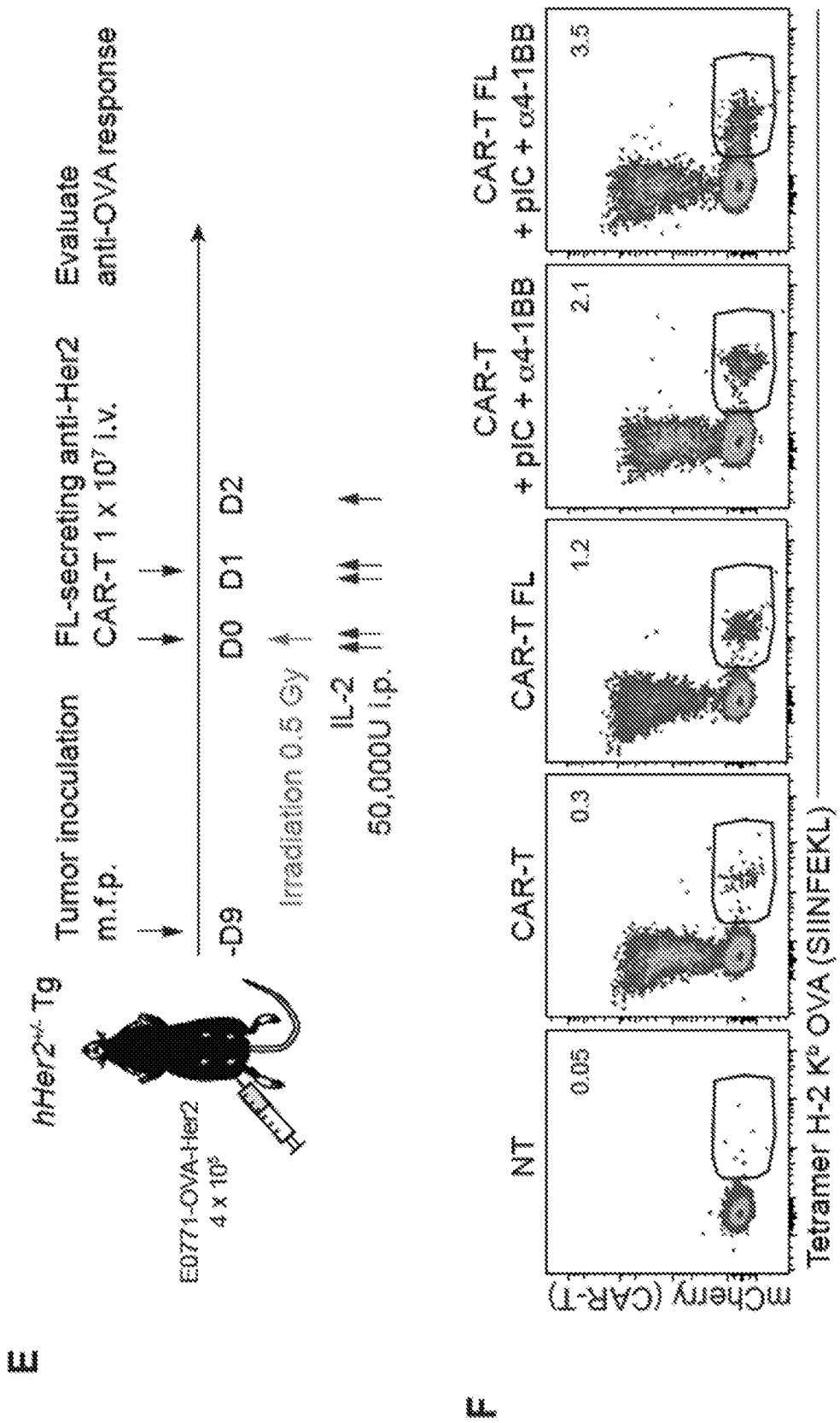
Figure 12:
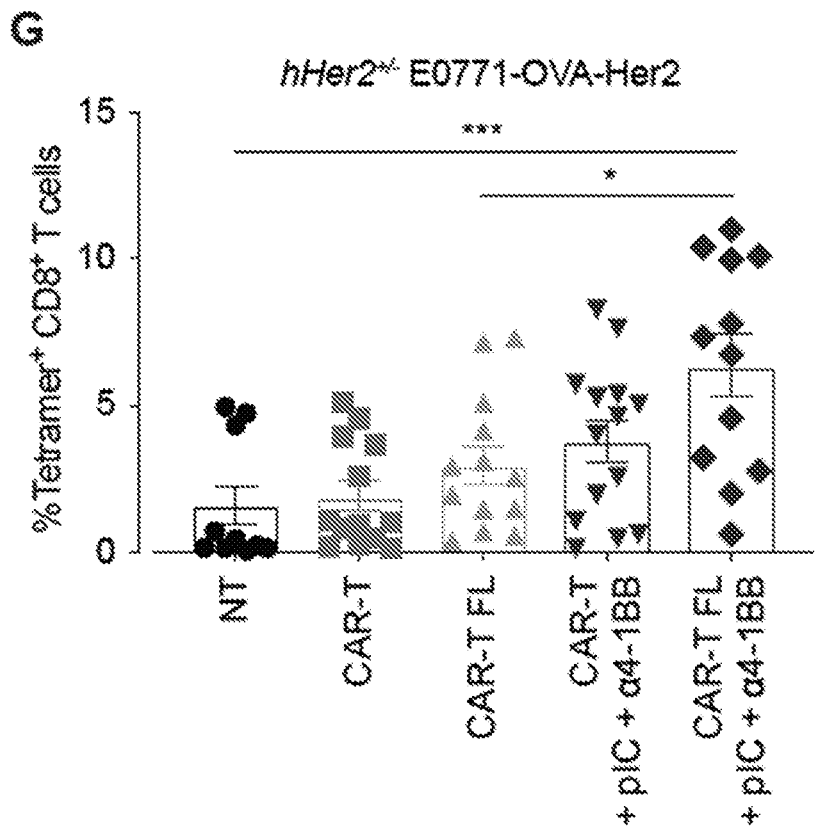
Figure 12:
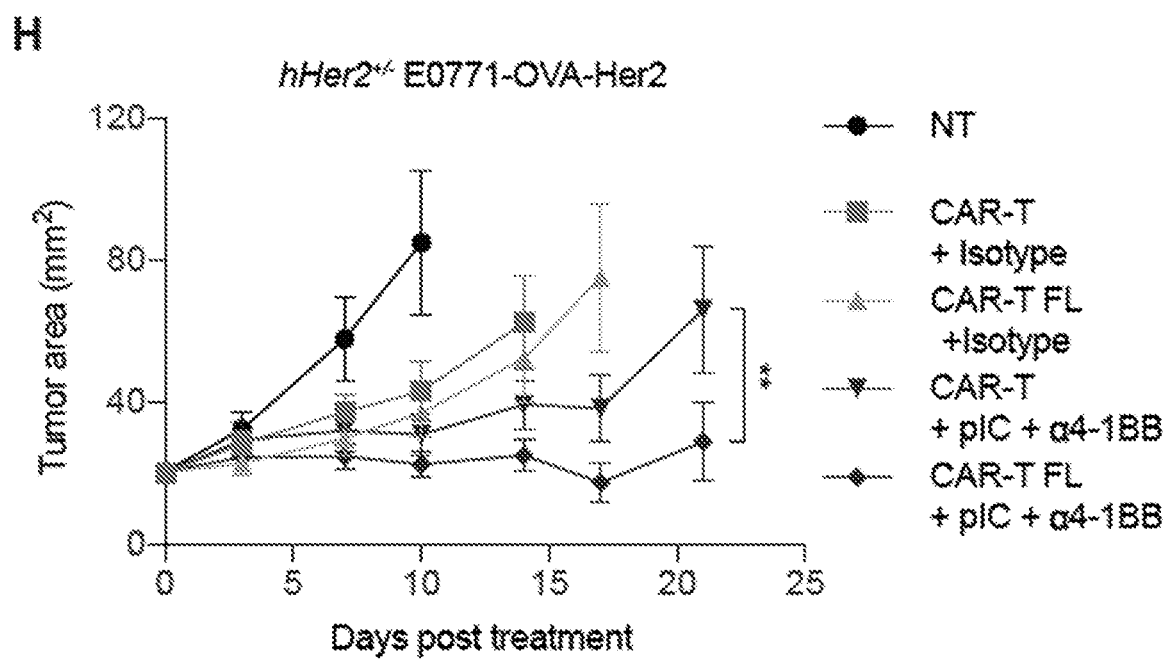

FIG. 12 shows that combination therapy with FLT3L-secreting T cells induces epitope spreading and a memory response. (A) A schematic representation of protocol for inoculation, cure and rechallenge of $hHer2^{+/-}$ mice; (B) A graphical representation of tumour area ($mm^2$; y-axis) against time (days post-parental tumour rechallenge; x-axis) in mice that were cured of their primary MC38-Her2 tumours; (C-D) A graphical representation of TCR (C) diversity and (D) frequency (%; y-axis) of $CD45.1^+$ host congenic mice at day 7 post-treatment, following inoculation with E0771-OVA tumours and adoptive transfer of $CD45.2^+$ OT-I T cells together with adjuvants, as indicated; (E) A schematic representation of the protocol to determine anti-tumour activity against antigens not targeted by the CAR; (F) A graphical representation of frequency of of H-2 Kb OVA Tetramer positive T cells (x-axis) and CAR T cells (y-axis); (G) A graphical representation of the proportion of $Tetramer^+$ $CD8^+$ T cells (%; y-axis) in $hHer2^{+/-}$ E0771-OVA-Her2 mice following treatment with a combination of FLT3L secreting CAR-T cells and adjuvants; and (H) A graphical representation of tumour area ($mm^2$; y-axis) against time (days post-treatment; x-axis) in $hHer2^{+/-}$ E0771-OVA-Her2 mice following treatment with a combination of FLT3L secreting CAR T cells and adjuvants. Data is shown as mean±SEM of n=3-12 mice per group of two pooled independent experiments, *p<0.05, p<0.01, *p<0.001, ****p<0.0001 (A and B two-way ANOVA, C-D and G one-way ANOVA, and H two-way ANOVA).

Figure 13:
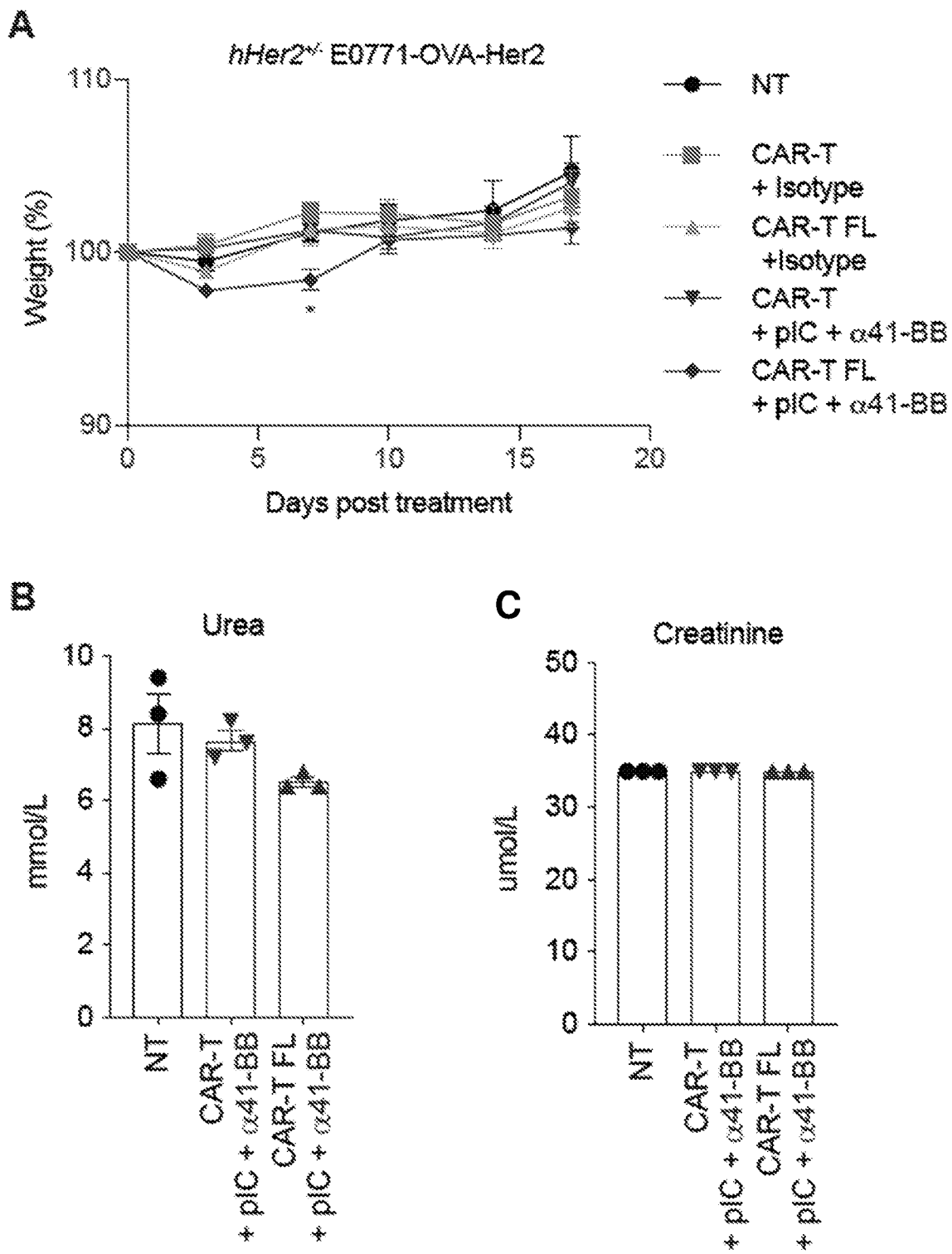
Figure 13:
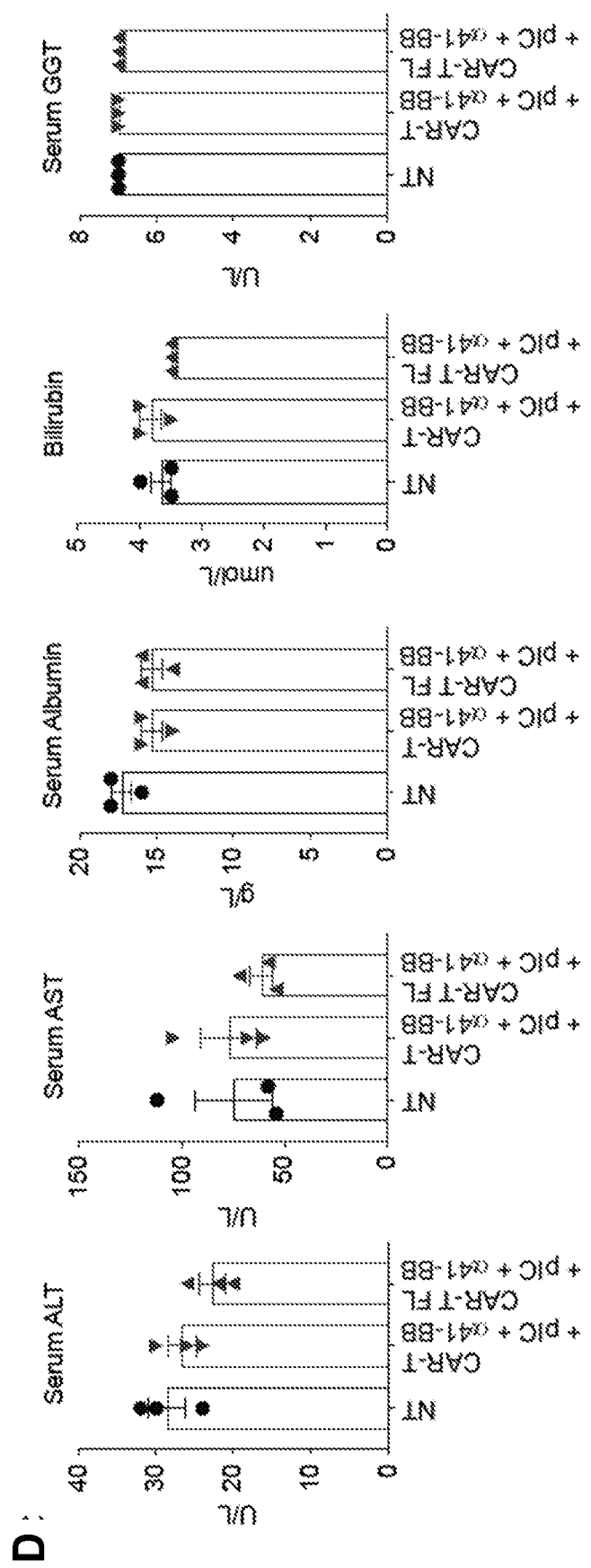
Figure 13:
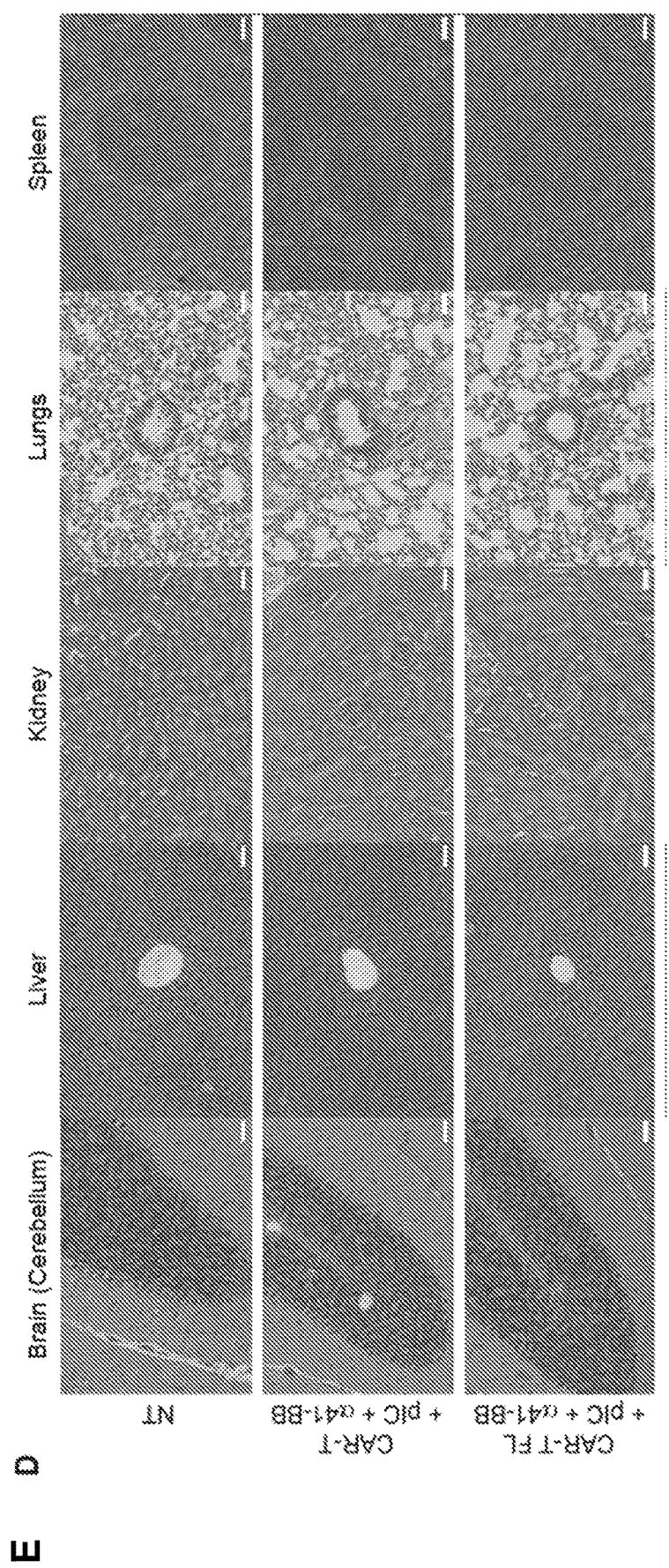
Figure 13:
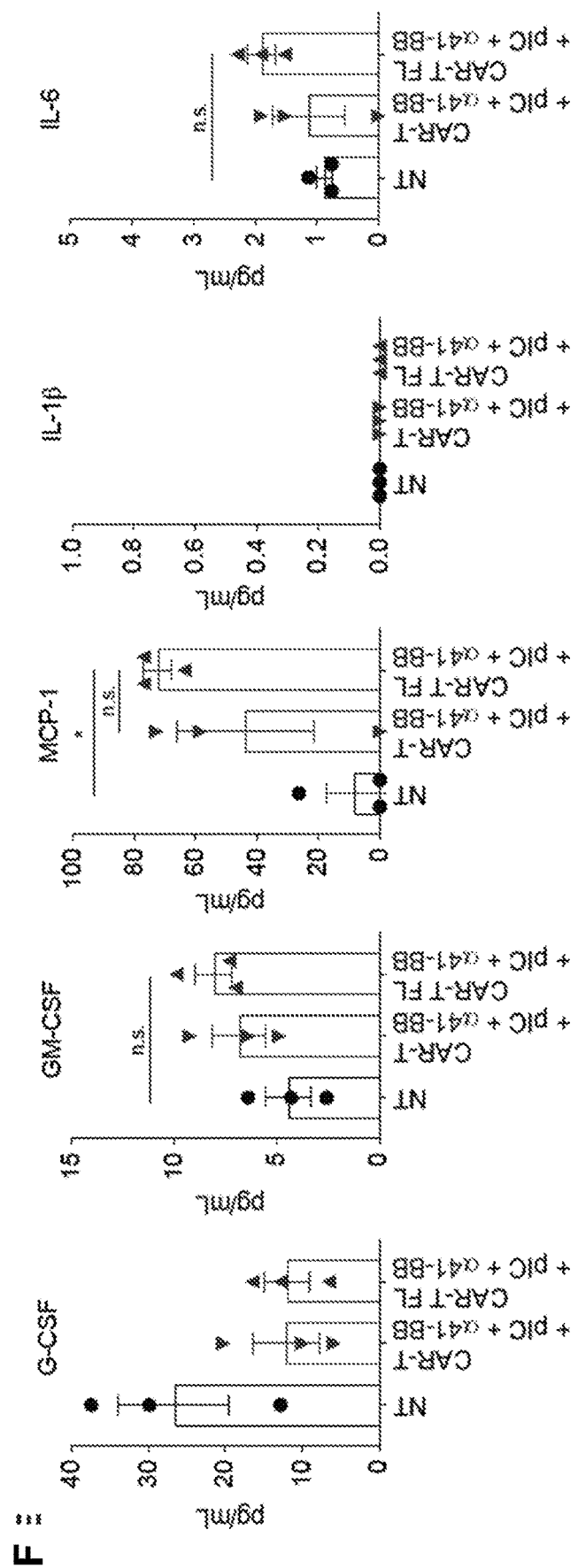

FIG. 13 shows that combination of FLT3L-secreting CAR T cells and adjuvant therapy does not induce significant toxicity. (A) A graphical representation of weight (%; y-axis) against time (days post-treatment; x-axis) in $hHer2^{+/-}$ transgenic mice inoculated with E0771-OVA-Her2 and treated with transduced CAR T cells; (B-D) A graphical representation of concentration of (B) urea, (C) creatinine and (D) ALT, AST, total albumin, bilirubin and gamma-glutamyl transferase (GGT) (U/L; y-axis) in serum at 48 hours post-adjuvant therapy; (E) A photographic representation of hematoxylin and eosin histology staining of cerebellum, liver, kidney, lungs and spleen of control non-treated (NT), CAR T or CAR T FL adjuvant treated mice, white bars indicate 50 µm; and (F) A graphical representation of concentration of cytokines G-CSF, GM-CSF, MCP-1, IL-113 and IL-6 (pg/mL; y-axis). Data shown is representative of n=3-8 mice per group, *p<0.05 (A one-way ANOVA).

Figure 14:
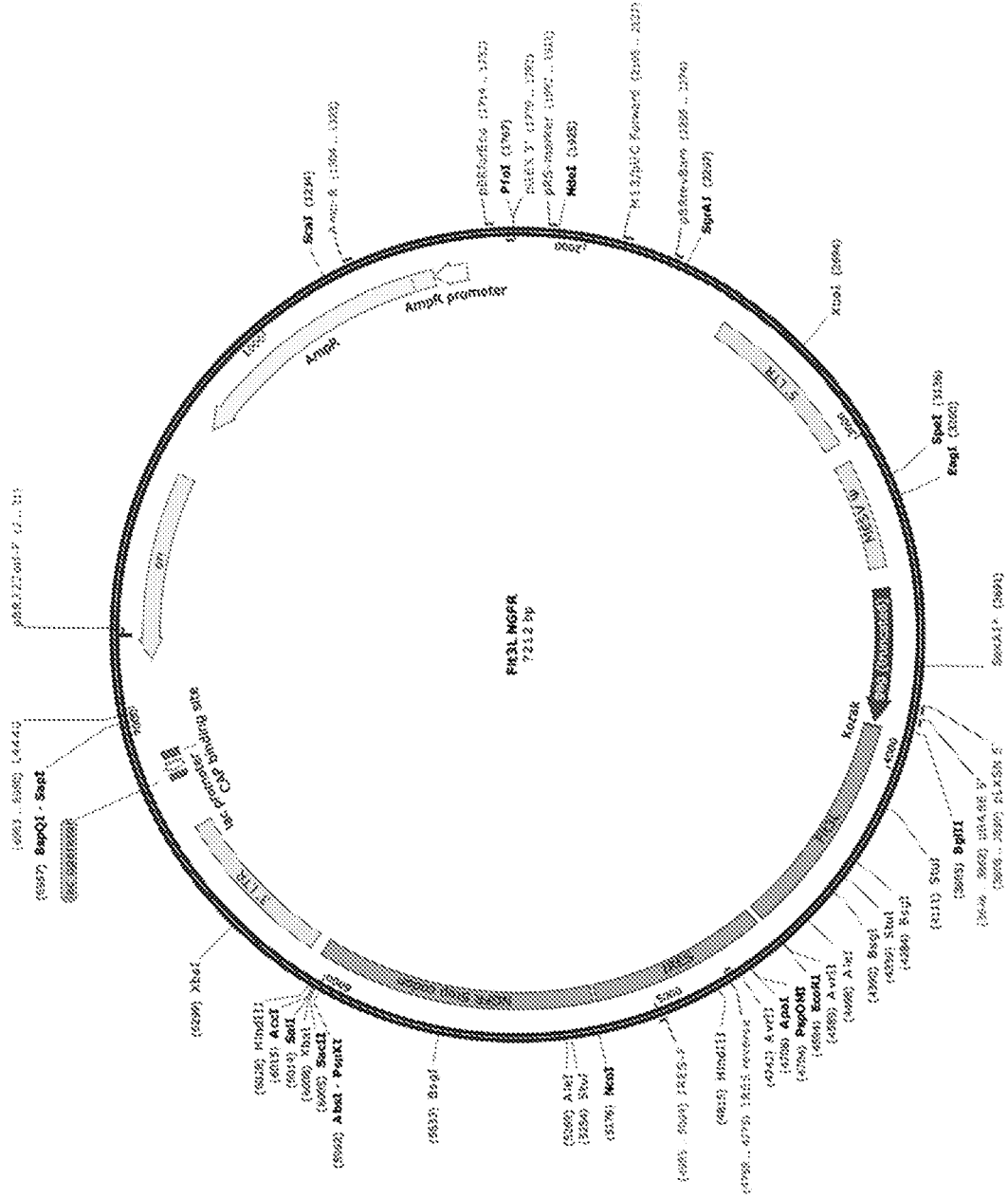

FIG. 14 is a schematic representation of the human nerve growth factor receptor (NGFR)-FLT3L vector.

Figure 15:
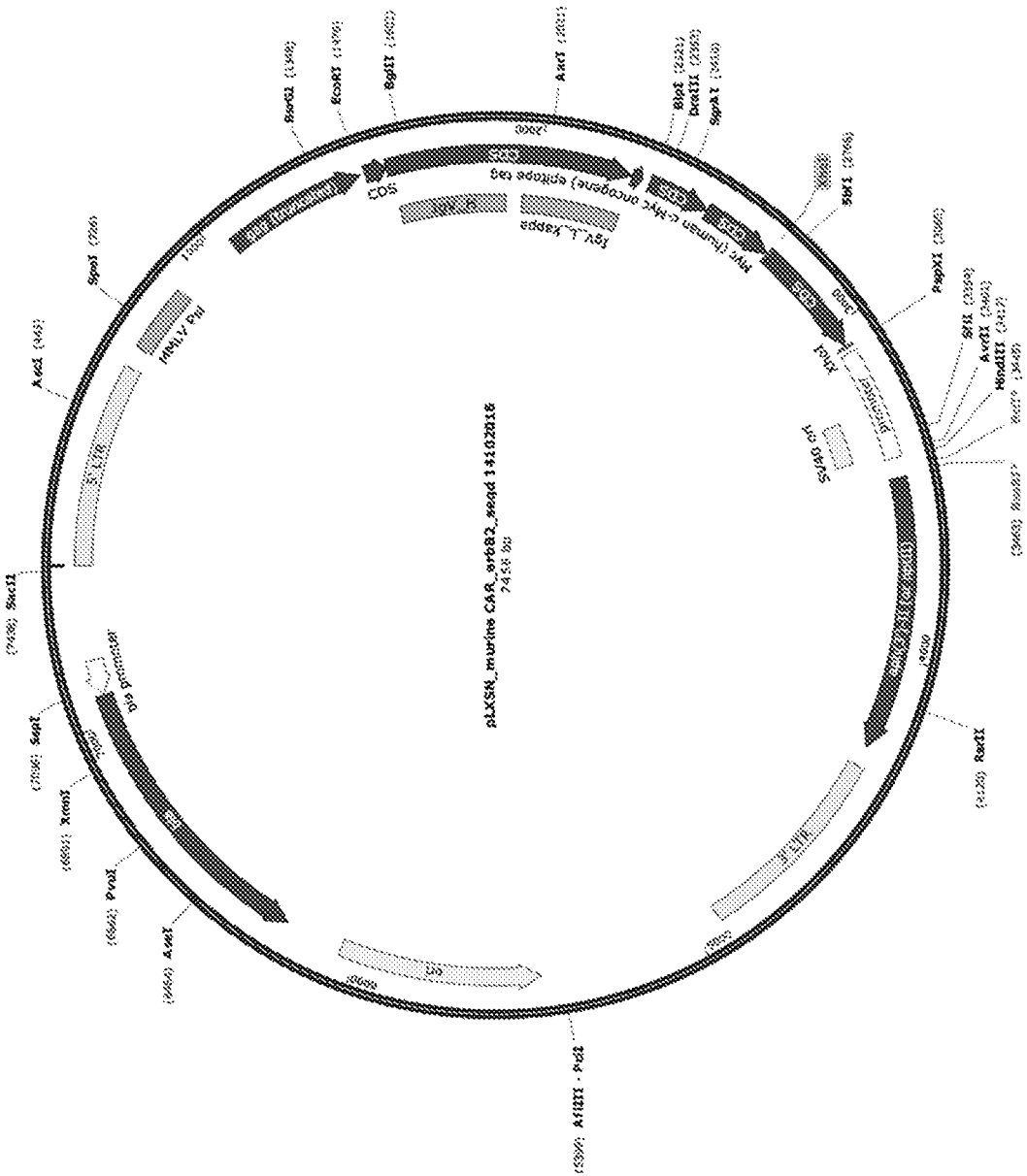

FIG. 15 is a schematic representation of the pLXSN anti-Her2 CAR vector.

Figure 16:
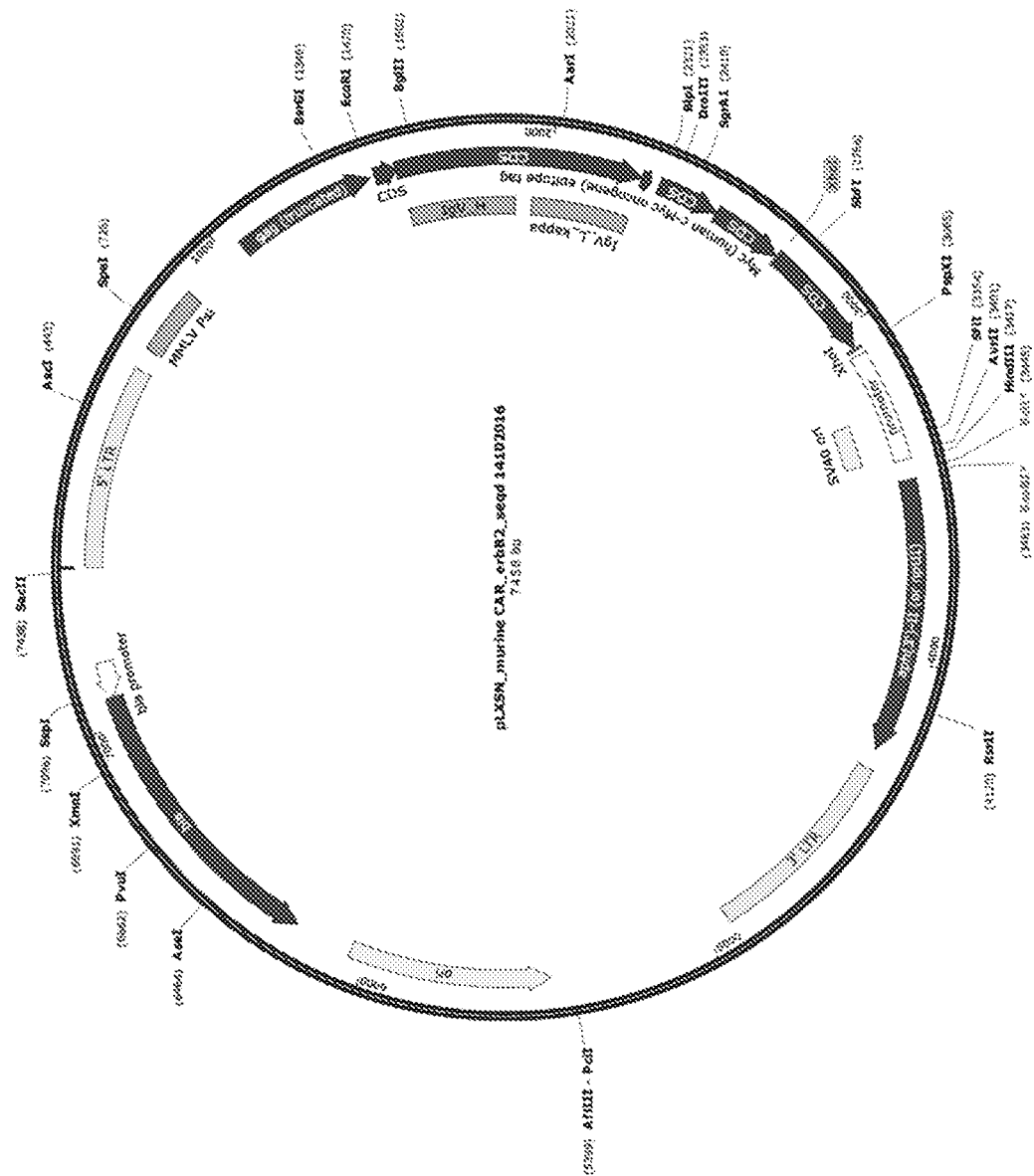

FIG. 16 is a schematic representation of the pSAMEN anti-Her2 CAR vector.

DETAILED DESCRIPTION OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavor to which this specification relates.

Unless specifically defined otherwise, all technical and scientific terms used herein shall be taken to have the same meaning as commonly understood by one of ordinary skill in the art.

Unless otherwise indicated the recombinant protein, cell culture and immunological techniques utilised in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

All publications mentioned in this specification are herein incorporated by reference in their entirety.

It must be noted that, as used in the subject specification, the singular forms "a", "an" and "the" include plural aspects unless the context clearly dictates otherwise. Thus, for example, reference to "a cell" includes a single cell, as well as two or more cells; reference to "an antigen" includes a single antigen, as well as two or more antigens; and so forth.

The present invention is predicated, in part, of the finding that T cells that are modified to express FMS-like tyrosine kinase ligand 3 (FLT3L) can be used to promote the differentiation of CD141$^+$/CD103$^+$ dendritic cells, thereby enhancing anti-tumour T cell responses, including endogenous anti-tumour immune responses, promotion of epitope spreading and enhancement of T cell trafficking. The inventors have surprisingly shown that the modulation of CD141$^+$/CD103$^+$ by modifying T cells to express FLT3L significantly enhances the activity of adoptive cellular therapy using both conventional T cells and chimeric antigen receptor (CAR) T cells. Importantly, the modified T cells of the present invention are particular adapted for the treatment of solid tumours.

FMS-Like Tyrosine Kinase Ligand 3 (FLT3L) Expressing T Cells

Accordingly, in a first aspect, the present invention provides an isolated T cell that is modified to express exogenous FMS-like tyrosine kinase 3 ligand (FLT3L).

The term "isolated" as used herein refers to material, such as a cell, which is substantially or essentially free from components which normally accompany or interact with it as found in its naturally occurring environment. The isolated material optionally comprises material not found with the material in its natural environment.

The terms "T cell" or "T lymphocyte" as well known in the art and refer to include thymocytes, naïve T lymphocytes, immature T lymphocytes, mature T lymphocytes, resting T lymphocytes, activated T lymphocytes or tumour infiltrating lymphocytes (TILs).

Illustrative populations of T cells suitable for use in particular embodiments include but are not limited to helper T cells (HTL; CD4$^+$ T cell), a cytotoxic T cell (CTL; CD8$^+$ T cell), CD4$^+$ CD8$^+$ T cell, CD4$^-$ CD8$^-$ T cell, or any other subset of T cells. Other illustrative populations of T cells suitable for use in particular embodiments include but are not limited to T cells expressing one or more of the following markers: CD3, CD4, CD8, CD27, CD28, CD45RA, CD45RO, CD62L, CD127, CD197, and HLA-DR and if desired, can be further isolated by positive or negative selection techniques.

In an embodiment, the isolated T cell is derived from a mammalian donor. In another embodiment, the isolated T cell is derived from a human donor.

According to the present invention, T cells are isolated from whole blood by any isolation method known in the art. For example, T cells may be isolated from whole blood using antibodies or beads.

In an embodiment, T cells are isolated from whole blood using a Ficoll-Paque separation method. The Ficoll-Paque method is used to isolate mononuclear cells from blood using low viscosity Ficoll and sodium metrizoate or sodium diatrizoate, as described by Bøyum (1968, *Scandinavian Journal of Clinical Laboratory Investigation*, 21 (Suppl. 97, Paper IV): 77-89). This method is well known in the art and adaptable to isolate mononuclear cells from peripheral blood, umbilical cord blood and bone marrow.

Modification of the isolated T cells may be accomplished by genetic engineering to express FLT3L. Methods of genetic engineering are well known in the art (see, for example, Ausubel supra; or Sambrook supra). For example, expression of FLT3L may be achieved by operably linking nucleic acids encoding FLT3L polypeptide or portions thereof to a promoter, and incorporating the construct into an expression vector. The vector can be suitable for replication and integration in eukaryotic cells. Typical cloning vectors contain transcription and translation terminators, initiation sequences and promoters useful for regulation of the expression of the desired nucleic acid sequence. An exemplary vector for the expression of FLT3L is provided in FIG. 14, which corresponds with SEQ ID NO: 1.

The term "modified T cell" as used herein refer to an isolated T cell that has been modified to express FLT3L, or an isolated T cell that has been modified to express both FLT3L and a CAR, wherein the CAR comprises an antigen binding domain and at least one signaling domain. Modified T cells can include both genetic and non-genetic modifications (e.g., episomal or extrachromosomal).

The terms "exogenous" and "ectopic" may be used interchangeably herein and refer to the expression of FLT3L that is not normally expressed in or on T cells or the expression of FLT3L at higher levels than normally observed on T cells.

The terms "FMS-like tyrosine kinase 3 ligand" or "FLT3L" are used herein to refer to a cytokine that regulates proliferation of early haematopoeitic cells. Multiple isoforms of FLT3L have been identified, with the predominant biologically active form being anchored to the cell surface as the extracellular domain of a transmembrane protein (UniProt ID: P49771-1, Isoform 1, human FLT3L; UniProt ID: P49772-1, Isoform 1, murine FLT3L). The membrane-bound isoform can be proteolytically cleaved to generate a biologically active soluble isoform (UniProt ID: P49771-2, Isoform 2, human FLT3L; UniProt ID: P49772-2, Isoform 2, murine FLT3L). Accordingly, the terms "FMS-like tyrosine kinase 3 ligand" or "FLT3L" refer to all isoforms of FLT3L, including the membrane-bound and soluble isoforms.

In an embodiment, the FLT3L isoform that is expressed by the modified T cells of the invention is Isoform 1.

Chimeric Antigen Receptor (CAR)/FLT3L T Cells

In an embodiment, the isolated T cells of the invention are also modified to express a chimeric antigen receptor (CAR), wherein the CAR comprises an antigen binding domain and at least one signaling domain.

The terms "Chimeric Antigen Receptor" or "CAR" as used herein mean a recombinant polypeptide construct comprising at least an antigen binding domain that is linked, via hinge and transmembrane domains, to an intracellular signaling domain.

The antigen binding domain is a functional portion of the CAR that is responsible for transmitting information within the cell to regulate cellular activity via defined signaling pathways. In an embodiment, the antigen binding domain may comprise an antibody or antibody fragment thereof.

The term "antibody" as used herein broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art.

In a full size antibody, each heavy chain comprises a heavy chain variable region (HCVR or VH) and a heavy chain constant region. The heavy chain constant region is comprised of three domains, CH1, CH2 and CH3. Each light chain comprises a light chain variable region (LCVR or VL) and a light chain constant region, CL. The VH and VL regions can be further subdivided into regions of hypervariability, termed complementary determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3 and FR4. Immunoglobulin molecules can be of any type (e.g. IgG, IgE, IgM, IgD, IgA and IgY), class (e.g. IgG1, IgG2, IgG3, IgG4, IgA1 and IgA2) or subclass.

The term "antibody fragment" as used herein means one or more fragments of an antibody that retain the ability to specifically bind to an antigen. Examples of antibody fragments include (i) a Fab fragment, a monovalent fragment consisting of the VL, VH, CL and CH1 domains; (ii) a F(ab')2 fragment, a F(ab')2 fragment, a bivalent fragment comprising two Fab fragments linked by a disulphide bridge at the hinge region; (iii) a Fd fragment consisting of the VH and CH1 domains; (iv) a single-chain variable fragment (scFv) consisting of the VL and VH domains of a single art of an antibody, (v) a dAb fragment (Ward et al. 1989, *Nature,* 341: 544-6), which comprises a single variable domain; and (vi) an isolated CDR.

In an embodiment, the antigen binding domain comprises an antibody fragment. For example, the antigen binding domain may comprise a scFv consisting of a VL and VH sequence of a monoclonal antibody (mAb) specific for a tumour cell surface molecule.

In an embodiment, the antigen binding domain binds to a tumour antigen.

The term "tumour antigen" as used herein means any protein produced by a tumour cell that elicits an immune response. Therefore, the selection of an antigen binding domain will depend on the type of cancer to be treated and the target tumour antigens and tumour cell surface markers that are expressed by the tumour cell. A tumour sample from a subject may be characterised for the presence of certain target tumour antigens and tumour cell surface markers. For example, breast cancer cells from a subject may be positive or negative for each of epidermal growth factor receptor 2 (Her2), estrogen receptor and/or progesterone receptor.

Target tumour antigens and tumour cell surface markers are known in the art and include, for example, CD19, CD20, CD22, CD30, ROR1, CD123, CD33, CD133, CD138, GD2, Her2, Her1, mesothelin, MUC1, gp100, MART-1, MAGE-A3, MUC16, NY-ESO-1 L1-CAM, CEA, FAP, VEGFR2, WT1, TAG-72, CD171, αFR, CAIX, PSMA and Lewis Y.

In an embodiment, the antigen binding domain binds to a tumour antigen that is not substantially expressed by normal cells.

In an embodiment, the antigen binding domain binds to an antigen selected from the group consisting of CD19, CD20, CD22, CD30, ROR1, CD123, CD33, CD133, CD138, GD2, Her2, Her1, mesothelin, MUC1, gp100, MART-1, MAGE-A3, MUC16, NY-ESO-1 L1-CAM, CEA, FAP, VEGFR2, WT1, TAG-72, CD171, αFR, CAIX, PSMA and Lewis Y and combinations thereof. In another embodiment, the antigen binding domain binds to Her2.

Complete and sustained T cell activation and proliferation require a primary initiating signal (signal 1), a secondary co-stimulatory receptor engagement signal (signal 2) and a cytokine receptor engagement signal (signal 3). As CAR T cells do not operate in a MHC-restricted manner, their interaction with antigen-presenting cells (APCs) is generally deficient, with signal 2 and signal 3 being severely compromised. Therefore, the incorporation of one or more signaling domains can impact on the levels and sustenance of the activation of T cells in response to tumour associated antigen, which can result in increased cytokine production.

In an embodiment, the CARs of the present invention comprise at least one signaling domain. In another embodiment, the CARs of the present invention comprise at least two signaling domains.

Examples of CAR signaling domains include CD3, CD28, 41BB, DAP10, OX40, ICOS, DAP12, KIR2DS2, 4-1BB, CD3s, CD35, CD3C, CD25, CD27, CD79A, CD79B, CARD11, FcRa, Fcftp, FcRy, Fyn, HVEM, Lck, LAG3, LAT, LRP, NKG2D, NOTCH1, NOTCH2, NOTCH3, NOTCH4, ROR2, Ryk, SLAMF1, Slip76, pTa, TCRa, TCRP, TRIM, Zap70, PTCH2 and LIGHT.

In an embodiment, the CAR comprises a signaling domain selected from the group consisting of the CD28 and CD3ζ signaling domains. In another embodiment, the CAR comprises both the CD28 and CD3ζ signaling domains.

Modification of the isolated T cells may be accomplished by genetic engineering to express a CAR. Methods of genetic engineering are well known in the art (see, for example, Ausubel supra; or Sambrook supra). For example, expression of a CAR may be achieved by operably linking nucleic acid sequences encoding a CAR polypeptide or portions thereof to a promoter, and incorporating the construct into an expression vector. The vector can be suitable for replication and integration in eukaryotic cells. Typical cloning vectors contain transcription and translation terminators, initiation sequences and promoters useful for regulation of the expression of the desired nucleic acid sequence. Suitable vectors for expression of a CAR are described in Beavis et al, 2017, supra (Her2 CAR), Ritchie et al., 2013, *Molecular Therapy*, 21(11): 2122-2129 (Lewis Y) and Westwood, et al., 2009, *Journal of Immunotherapy*, 32(3): 292-301. Exemplary vectors are provided in FIGS. 14 and 15, which correspond with SEQ ID NOs: 2 and 3.

Pharmaceutical Compositions

In an aspect, the present invention provides a pharmaceutical composition comprising a therapeutically effective amount of an isolated T cell modified to express exogenous FLT3L and at least one pharmaceutically acceptable carrier.

In an embodiment, the pharmaceutical composition comprises a therapeutically effective amount of an isolated T cell modified to express exogenous FLT3L and a CAR, wherein the CAR comprises an antigen binding domain and at least one signaling domain.

In an embodiment, a pharmaceutical composition comprising the modified T cells of the present invention may be administered at a dosage of $10^4$ to $10^9$ cells/kg body weight. In another embodiment, a pharmaceutical composition comprising the modified T cells of the present invention may be administered at a dosage of $10^5$ to $10^6$ cells/kg body weight, including all integer values within those ranges.

Compositions comprising the modified T cells of the present invention may also be administered multiple times at these dosages. The cells can be administered by using infusion techniques that are known in the art (see, for example, Rosenberg et al., 1988, *New England Journal of Medicine*, 319: 1676). The optimal dosage and treatment regimen for a particular subject can be readily determined by one skilled in the art by monitoring the patient for signs of disease and adjusting the treatment accordingly.

The composition of the present invention may be prepared in a manner known in the art and are those suitable for parenteral administration to mammals, particularly humans, comprising a therapeutically effective amount of the composition alone, with one or more pharmaceutically acceptable carriers or diluents.

The term "pharmaceutically acceptable carrier" as used herein means any suitable carriers, diluents or excipients. These include all aqueous and non-aqueous isotonic sterile injection solutions which may contain anti-oxidants, buffers and solutes, which render the composition isotonic with the blood of the intended recipient; aqueous and non-aqueous sterile suspensions, which may include suspending agents and thickening agents, dispersion media, antifungal and antibacterial agents, isotonic and absorption agents and the like. It will be understood that compositions of the invention may also include other supplementary physiologically active agents.

The carrier must be pharmaceutically "acceptable" in the sense of being compatible with the other ingredients of the composition and not injurious to the subject. Compositions include those suitable for parenteral administration, including subcutaneous, intramuscular, intravenous and intradermal administration. The compositions may conveniently be presented in unit dosage form and may be prepared by any method well known in the art of pharmacy. Such methods include preparing the carrier for association with the modified T cells. In general, the compositions are prepared by uniformly and intimately bringing into association any active ingredients with liquid carriers.

In an embodiment, the composition is suitable for parenteral administration. In another embodiment, the composition is suitable for intravenous administration.

Compositions suitable for parenteral administration include aqueous and non-aqueous isotonic sterile injection solutions which may contain anti-oxidants, buffers, bactericides and solutes, which render the composition isotonic with the blood of the intended recipient; and aqueous and non-aqueous sterile suspensions which may include suspending agents and thickening agents.

The invention also contemplates the combination of the composition of the present invention with other drugs and/or in addition to other treatment regimens or modalities such as radiation therapy or surgery. When the composition of the present invention is used in combination with known therapeutic agents the combination may be administered either in sequence (either continuously or broken up by periods of no treatment) or concurrently or as an admixture. In the case of cancer, there are numerous known anti-cancer agents that may be used in this context. Treatment in combination is also contemplated to encompass the treatment with either the composition of the invention followed by a known treatment, or treatment with a known agent followed by treatment with the composition of the invention, for example, as maintenance therapy. For example, in the treatment of cancer it is contemplated that the composition of the present invention may be administered in combination with an alkylating agent (such as mechlorethamine, cyclophosphamide, chlorambucil, ifosfamidecysplatin, or platinum-containing alkylating agents such as cisplatin, carboplatin and oxaliplain), and anti-metabolite (such as a purine or pyrimidine analogue or an anti-folate agent, such as azathioprine and mercaptopurine), an anthracycline (such as daunorubicin, doxorubicin, epirubicin idarubicin, valrubicin, mitoxantrone or anthracycline analog), a plant alkaloid (such as a vinca alkaloid or a taxane, such as vincristine, vinblastine, vinorelbine, vindesine, paclitaxel or doestaxel), a topoisomerase inhibitor (such as a type I or type II topoisomerase inhibitor), a podophyllotoxin (such as etoposide or teniposide), a tyrosine kinase inhibitor (such as imatinib mesylate, nilotinib or dasatinib), an adenosine receptor inhibitor (such as A2aR inhibitors, SCH58261, CPI-444, SYN115, ZM241385, FSPTP or $A2_BR$ inhibitors such as PSB-1115), adenosine receptor agonists (such as CCPA, IB-MECA and CI-IB-MECA), a checkpoint inhibitor, including those of the PDL-1:PD-1 axis, nivolumab, pembrolizumab, atezolizumab, BMS-936559, MEDI4736, MPDL33280A or MSB0010718C), an inhibitor of the CTLA-4 pathway (such as ipilimumab and tremelimumab), an inhibitor of the TIM-3 pathway or an agonist monoclonal antibody that is known to promote T cell function (including anti-OX40, such as MEDI6469; and anti-4-1BB, such as PF-05082566).

In an embodiment, the composition of the presently claimed invention is administered in combination with one or more of the group consisting of an inhibitor of the PDL-1: PD-1 axis, a TLR3 agonist, a 4-1BB agonist, a TLR7 agonist, an inhibitor of TIM-3, and an inhibitor of CTLA-4.

In an embodiment, the composition of the presently claimed invention is administered in combination with one or more immune adjuvants.

The term "immune adjuvant" as used herein refers to a compound or substance that is capable of enhancing a subject's immune response to the immunogen including, for example, the subject's antibody response to the immunogen. An immune adjuvant may therefore assist to enhance the immune response to an isolated T cell modified to express exogenous FLT3L in a subject, compared to the administration of the modified T alone or in the absence of the immune adjuvant.

Suitable immune adjuvants will be familiar to persons skilled in the art, illustrative examples of which include an inhibitor of the PDL-1: PD-1 axis, a TLR3 agonist, a 4-1BB agonist, a TLR7 agonist, an inhibitor of TIM-3, and an inhibitor of CTLA-4. Thus, in an embodiment, the immune adjuvant is selected from the group consisting of an inhibitor of the PDL-1: PD-1 axis, a TLR3 agonist, a 4-1BB agonist, a TLR7 agonist, an inhibitor of TIM-3, and an inhibitor of CTLA-4.

An "inhibitor of the PDL-1: PD-1 axis" is intended to mean any compound or ligand, or a pharmaceutically acceptable salt thereof, which inhibits the PDL-1: PD-1 axis in a cell. For example, the inhibitor of the PDL-1: PD-1 axis may be an allosteric or catalytic inhibitor.

In an embodiment, the inhibitor of the PDL-1: PD-1 axis is selected from the group consisting of nivolumab, pembrolizumab, atezolizumab, BMS-936559, MEDI4736, MPDL33280A and MSB0010718C. In another embodiment, the inhibitor of the PDL-1: PD-1 axis is RMP1-14.

A "Toll-like receptor 3 agonist" or "TLR3 agonist" is intended to mean any compound or ligand, or a pharmaceutically acceptable salt thereof, which initiates a TLR3-mediated immune response.

In an embodiment, the TLR3 agonist is selected from the group consisting of polyinosinic:polycytidylic acid (also referred to as poly IC or pIC), poly ICLC, polyIC$_{12}$U and IPH3102. In a preferred embodiment, the TLR3 agonist is poly IC or poly ICLC.

A "4-1BB agonist" is intended to mean any compound or ligand, or a pharmaceutically acceptable salt thereof, which initiates an immune-stimulatory response when combined with 4-1BB.

In an embodiment, the 4-1BB agonist is an anti-4-1BB antibody.

An "inhibitor of T cell immunoglobulin and mucin domain-3" or "an inhibitor of TIM-3" is intended to mean any compound or ligand, or a pharmaceutically acceptable salt thereof, which inhibits TIM-3 in a cell. For example, the inhibitor of TIM-3 may be an allosteric or catalytic inhibitor.

TIM-3 is an inhibitory T cell receptor, with potential immune checkpoint inhibitory and anti-tumour activity. TIM-3 is expressed on macrophages and cDCs in tumours and normal tissues, with high levels of expression on the cDC1 subset (Pulido et al., 2018, Cancer Cell, 33(1): P60-74.E6). Inhibition of TIM-3 abrogates T cell inhibition, activates antigen-specific T lymphocytes and enhances cytotoxic T cell-mediated tumour cell lysis. Inhibition of TIM-3 using antibodies have also been shown to improve response to chemotherapy in models of triple-negative and luminal B breast cancer, with no evidence of toxicity. This combined effect was CD8$^+$ T cell dependent and associated with increased granzyme B expression (Pulido et al., supra). An inhibitor of TIM-3 indirectly enhances CD8$^+$ T cell response during chemotherapy, and may be adapted for use as an immune adjuvant in accordance with the methods described herein.

In an embodiment, the inhibitor of TIM-3 is an anti-TIM-3 antibody. Suitable anti-TIM-3 antibodies would be known to persons skilled in the art, an illustrative example of which includes the anti-TIM-3 monoclonal antibody, TSR-022.

A "Toll-like receptor 7 agonist" or "TLR7 agonist" is intended to mean any compound or ligand, or a pharmaceutically acceptable salt thereof, which initiates a TLR7-mediated immune response.

TLR7 is an intracellular receptor that recognises single-stranded RNA molecules and detects RNA viruses such as the influenza virus. Stimulation of TLR7 has been shown to produce multiple pro-inflammatory cytokines, including Type I IFN and IL-12. Type I IFN and IL-12 have been shown to be critical mediators of cross-priming induced by TLR7 agonists, which facilitates CD8+ T cell responses by coordinated recruitment and activation of both tissue-derived and lymphoid organ-resident DC subsets through a Type I IFN and IL-12 co-dependent mechanism (Oh, et al., 2011, Blood, 118(11): 3028-3038).

In an embodiment, the TLR7 agonist is selected from the group consisting of TLR7 agonist-antigen conjugates, Imiquimod (Aldara), Resiquimod, Gardiquimod, Loxoribine, poly(dT), TL8-506, CL075, CL097, CL264, and CL307.

An "inhibitor of CTLA-4" is intended to mean any compound or ligand, or a pharmaceutically acceptable salt thereof, which inhibits CTLA-4 in a cell. For example, the inhibitor of CTLA-4 may be an allosteric or catalytic inhibitor.

In an embodiment, the inhibitor of CTLA-4 is ipilimumab.

Vectors

The present invention provides a vector comprising a nucleic acid encoding FLT3L operably linked to a T cell-specific regulatory element.

In an embodiment, the vector further comprises a nucleic acid encoding a CAR, wherein the CAR comprises an antigen binding domain and at least one signaling domain.

The terms "polynucleotide", "polynucleotide sequence", "nucleotide sequence", "nucleic acid" or "nucleic acid sequence" as used herein designate mRNA, RNA, cRNA, cDNA or DNA. The term typically refers to polymeric form of nucleotides of at least 10 bases in length, either ribonucleotides or deoxynucleotides or a modified form or either type of nucleotide. The term includes single and double stranded forms of RNA and DNA.

As used herein, the term "gene" includes a nucleic acid molecule capable of being used to produce mRNA optionally with the addition of elements to assist in this process. Genes may or may not be capable of being used to produce a functional protein. Genes can include both coding and non-coding regions (e.g., introns, regulatory elements, promoters, enhancers, termination sequences and 5' and 3' untranslated regions).

The term "transgene" is used herein to describe genetic material that has been or is about to be artificially introduced into a genome of a host organism and that is transmitted to the progeny of that host. In some embodiments, it confers a desired property to a T cell which it is introduced, or otherwise leads to a desired therapeutic outcome.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

The term "operably connected" or "operably linked" as used herein refers to a juxtaposition wherein the components so described are in a relationship permitting them to function in their intended manner. For example, a transcriptional control sequence "operably linked" to a coding sequence refers to the positioning and/or orientation of the transcriptional control sequence relative to the coding sequence to permit expression of the coding sequence under conditions compatible with the transcriptional control sequence. In another example, a NFAT promoter operably linked to a FLT3L coding sequence refers to the positioning and/or orientation of the NFAT promoter to the FLT3L coding sequence to permit translation of the FLT3L coding sequence in the tumour microenvironment where CAR activation occurs.

As used here the terms "open reading frame" and "ORF" are used interchangeably herein to refer to the amino acid sequence encoded between translation initiation and termination codons of a coding sequence. The terms "initiation codon" (e.g., ATG) and "termination codon" (e.g., TGA, TAA, TAG) refer to a unit of three adjacent nucleotides ('codon') in a coding sequence that specifies initiation and chain termination, respectively, of protein synthesis (mRNA translation).

"Polypeptide", "peptide", "protein" and "proteinaceous molecule" are used interchangeably herein to refer to molecular comprising or consisting of a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

As used herein the term "recombinant" as applied to "nucleic acid molecules", "polynucleotides" and the like is understood to mean artificial nucleic acid structures (i.e., non-replicating cDNA or RNA; or replicons, self-replicating cDNA or RNA) which can be transcribed and/or translated in isolated T cells as described herein. Recombinant nucleic acid molecules or polynucleotides may be inserted into a vector. Non-viral vectors such as plasmid expression vectors or viral vectors may be used. The kinds of vectors and the technique of insertion of the nucleic acid construct according to this invention are known in the art. A nucleic acid molecule or polynucleotide according to the invention does not occur in nature in the arrangement described by the present invention. In other words, a heterologous nucleotide sequence is not naturally combined with elements of a virus genome (e.g., promoter, ORF, polyadenylation signal, ribozyme).

By "regulatory element" or "regulatory sequence" is meant nucleic acid sequences (e.g., DNA) necessary for expression of an operably linked coding sequence in a particular cell. The regulatory sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

In an embodiment, the vector comprises a nucleic acid encoding FLT3L operably linked to a T cell-specific regulatory element. T cell-specific regulatory elements are known in the art and include, for example, the NFAT consensus sequence is T cell activation specific, the NFκB promoter is also activated during T cell activation.

Chimeric constructs suitable for affecting the present modified T cells comprise a nucleic acid sequence encoding FLT3L, which is operably linked to a regulatory element. Such chimeric constructs may also comprise a nucleic acid sequence encoding a CAR, wherein the CAR comprises an antigen binding domain and at least one signalling domain. Alternatively, a separate chimeric construct may be provided comprising a nucleic acid sequence encoding a CAR, wherein the CAR comprises an antigen binding domain and at least one signalling domain, which is operably linked to a regulatory element. The regulatory element suitably comprises transcriptional and/or translational control sequences, which will be compatible for expression in the cell. Typically, the transcriptional and translational control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated. The promoters may be either naturally occurring promoters, or hybrid promoters that combine elements of more than one promoter.

Promoter sequences contemplated may be native to mammalian cells or may be derived from an alternative source, where the region is functional in the chosen organism. The choice of promoter will differ depending on the intended host cell. For example, promoters which could be used for expression in mammalian cells include the metallothionein promoter, which can be induced in response to heavy metals such as cadmium, the (3-actin promoter as well as viral promoters such as the SV40 large T antigen promoter, human cytomegalovirus (CMV) immediate early (IE) promoter, Rous sarcoma virus LTR promoter, the mouse mammary tumour virus LTR promoter, the adenovirus major late promoter (Ad MLP), the herpes simplex virus promoter, and a HPV promoter, particularly the HPV upstream regulatory region (URR), among others. All these promoters are well described and readily available in the art.

In an embodiment, the regulatory element comprises an inducible promoter sequence that restricts expression of transgenes to the tumour microenvironment where CAR activation occurs. Suitable inducible promoters are known in the art, for example, the NFAT promoter is activated downstream of the TCR/CAR, which therefore restricts expression of transgenes to the tumour microenvironment where CAR activation occurs.

In an embodiment, the vector comprises a nucleic acid encoding FLT3L operably linked to a regulatory element, wherein the regulatory element comprises the NFAT promoter sequence. In an embodiment, the vector comprising a nucleic acid encoding FLT3L is the (NGFR)-FLT3L vector shown in FIG. 14, which corresponds with SEQ ID NO: 1.

In an embodiment, the vector comprises a nucleic acid encoding a CAR operably linked to a regulatory element. In another embodiment, the vector comprises a nucleic acid encoding a CAR containing the CD28 and TCR-t signaling domains recognizing the human Her2 antigen (scFv-CD28-

ζ). In another embodiment, the vector comprising a nucleic acid encoding a CAR is the pLXSN anti-Her2 CAR vector shown in FIG. 15, which corresponds with SEQ ID NO: 2. In yet another embodiment, the vector comprising a nucleic acid encoding a CAR is the pSAMEN anti-Her2 CAR vector shown in FIG. 16, which corresponds with SEQ ID NO: 3.

In another embodiment, the vector comprises a nucleic acid encoding FLT3L operably linked to a regulatory element, wherein the regulatory element comprises a constitutively active promoter sequence.

Enhancer elements may also be used herein to increase expression levels of the mammalian constructs. Examples include the SV40 early gene enhancer, as described for example in Dijkema et al. (1985, *EMBO Journal*, 4:761), the enhancer/promoter derived from the long terminal repeat (LTR) of the Rous Sarcoma Virus, as described for example in Gorman et al., (1982, *Proceedings of the National Academy of Science. USA*, 79:6777) and elements derived from human CMV, as described for example in Boshart et al. (1985, *Cell*, 41:521), such as elements included in the CMV intron A sequence.

The chimeric construct may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognized by the presence of homology to the canonical form 5' AATAAA-3' although variations are not uncommon. The 3' non-translated regulatory DNA sequence preferably includes from about 50 to 1,000 nts and may contain transcriptional and translational termination sequences in addition to a polyadenylation signal and any other regulatory signals capable of effecting mRNA processing or gene expression.

In some embodiments, the chimeric construct further contains a selectable marker gene to permit selection of cells containing the construct. Selection genes are well known in the art and will be compatible for expression in the cell of interest.

In one embodiment, expression of FLT3L is under the control of a promoter. In one non-limiting embodiment the promoter is a cellular constitutive promoter, such as human EF1 alpha (human elongation factor 1 alpha gene promoter), DHFR (dihydrofolate reductase gene promoter) or PGK (phosphoglycerate kinase gene promoter) that direct expression of a sufficient level of CP77 to sustain viral propagation in the absence of significant toxic effects on the host cell. Promoters may also be inducible, such as the cellular inducible promoter, MTH (from a metallothionein gene) viral promoters are also employed in mammalian cells, such as CMV, RSV, SV-40, and MoU3. In an embodiment, the promoter is the NFAT consensus sequence.

Viral Transduction

In an aspect, the present invention provides a viral particle comprising a nucleic acid encoding FLT3L.

The term "viral particle" as used herein refers to any virus or viral system used to transduce cells. Suitable viral particles are known in the art and include, for example, retroviruses (e.g., MoMLV, etc), lentiviruses, adenoviruses, AAVs and EBV. In an embodiment, the viral particle is a retrovirus.

In an embodiment, the viral particle further comprises a nucleic acid encoding a CAR, wherein the CAR comprises an antigen binding domain and at least one signaling domain.

"Transduction" refers to the delivery of gene(s) or other polynucleotide sequence, such as a polynucleotide sequence encoding FLT3L or a CAR, to T cells using one or more vectors. In an embodiment, retroviral particles are transduced into a cell through infection and provirus integration. In certain embodiment, a target cell, e.g., a T cell, is "transduced" if it comprises a gene or other polynucleotide sequence delivered to the cell by infection using a viral or retroviral vector.

Modified T Cells for the Treatment of Cancer

The present invention provides a method for treating cancer comprising administering a therapeutically effective amount of an isolated T cell modified to express exogenous FLT3L or a pharmaceutical composition comprising an isolated T cell modified to express exogenous FLT3L to a subject in need thereof.

In an embodiment, the method for treating cancer comprises administering a therapeutically effective amount of an isolated T cell modified to express exogenous FLT3L and a CAR, wherein the CAR comprises an antigen binding domain and at least one signaling domain, or a pharmaceutical composition comprising an isolated T cell modified to express exogenous FLT3L and a CAR, wherein the CAR comprises an antigen binding domain and at least one signaling domain to a subject in need thereof.

In another aspect, the present invention provides a use of an isolated T cell modified to express exogenous FLT3L in the manufacture of a medicament for the treatment of cancer.

In an embodiment, the use comprises an isolated T cell modified to express exogenous FLT3L and a CAR, wherein the CAR comprises an antigen binding domain and at least one signaling domain in the manufacture of a medicament for the treatment of cancer.

In an embodiment, the method further comprises the administration of one or more immune adjuvants.

In an embodiment, the immune adjuvant is selected from the group consisting of an inhibitor of the PDL-1: PD-1 axis, a TLR3 agonist, a 4-1BB agonist, a TLR7 agonist, an inhibitor of TIM-3 and an inhibitor of CTLA-4.

The therapeutic regimen for the treatment of cancer can be determined by a person skilled in the art and will typically depend on factors including, but not limited to, the type, size, stage and receptor status of the tumour in addition to the age, weight and general health of the subject. Another determinative factor may be the risk of developing recurrent disease. For instance, for a subject identified as being at high risk or higher risk or developing recurrent disease, a more aggressive therapeutic regimen may be prescribed as compared to a subject who is deemed at a low or lower risk of developing recurrent disease. Similarly, for a subject identified as having a more advanced stage of cancer, for example, stage III or IV disease, a more aggressive therapeutic regimen may be prescribed as compared to a subject that has a less advanced stage of cancer.

The term "cancer" as used herein means any condition associated with aberrant cell proliferation. Such conditions will be known to persons skilled in the art. In an embodiment, the cancer is a primary cancer (e.g., a tumour). In another embodiment, the cancer is a metastatic cancer. In yet another embodiment, the cancer is a solid cancer.

The terms "treat", "treatment" and "treating" as used herein refers to any and all uses which remedy a condition or symptom, or otherwise prevent, hinder, retard, abrogate or reverse the onset or progression of cancer or other undesirable symptoms in any way whatsoever. Thus, the term "treating" and the like are to be considered in their broadest possible context. For example, treatment does not necessarily imply that a subject is treated until total recovery or cure. In conditions that display or are characterised by multiple symptoms, the treatment need not necessarily remedy, prevent, hinder, retard, abrogate or reverse all of said symptoms, but may remedy, prevent, hinder, retard, abrogate or reverse one or more of said symptoms.

The subject in which cancer is to be treated may be a human or a mammal of economic importance and/or social importance to humans, for instance, carnivores other than humans (e.g., cats and dogs), swine (e.g., pigs, hogs, and wild boars), ruminants (e.g., cattle, oxen, sheep, giraffes, deer, goats, bison, and camels), horses, and birds including those kinds of birds that are endangered, kept in zoos, and fowl, and more particularly domesticated fowl, e.g., poultry, such as turkeys, chickens, ducks, geese, guinea fowl, and the like, as they are also of economic importance to humans. The term "subject" does not denote a particular age. Thus, adult, juvenile and newborn subjects are intended to be covered.

The terms "subject", "individual" and "patient" are used interchangeably herein to refer to any subject to which the present disclosure may be applicable. In an embodiment, the subject is a mammal. In another embodiment, the subject is a human.

The term "therapeutically effective amount" as used herein means the amount of modified T cells when administered to a mammal, in particular a human, in need of such treatment, is sufficient to treat cancer. The precise amount of modified T cells to be administered can be determined by a physician with consideration of individual differences in age, weight, tumour size, extent of infection or metastasis, and condition of the subject.

Typically, administration of T cell therapies is defined by number of cells per kilogram of body weight. However, because T cells will replicate and expand after transfer, the administered cell dose will not resemble the final steady-state number of cells.

In another aspect, the present invention provides a method of "adoptive cellular therapy" or "adoptive immunotherapy" for the treatment of cancer. Accordingly, such methods comprise:
  a. taking a biological sample comprising T cells from a subject;
  b. isolating T cells from the sample;
  c. transducing the isolated T cells in vitro with one or more vectors of the invention;
  d. expanding the modified T cells of step (c) under conditions such that the nucleic acid(s) encoded by the vector(s) is expressed; and
  e. administering a therapeutically effective amount of the modified T cells to the subject.

The terms "sample" or "biological sample" as used herein refers to tissues or body fluids removed from a subject, preferably a mammal, and which contain T cells. Sources of T cells are well known in the art and include peripheral blood, peripheral blood mononuclear cells, bone marrow, lymph nodes tissue, cord blood, thymus tissue, tissue from the site of infection, ascites, pleural effusion, spleen tissue, and tumours. In an embodiment, the biological sample is whole blood taken from the subject.

According to the present invention, T cells are isolated from the sample by any isolation method known in the art. For example, T cells may be isolated from whole blood using antibodies or beads.

In an embodiment, T cells are isolated using a Ficoll-Paque separation method. The Ficoll-Paque method is used to isolate mononuclear cells from blood using low viscosity Ficoll and sodium metrizoate or sodium diatrizoate, as described by Bøyum (1968, *Scandinavian Journal of Clinical Laboratory Investigation*, 21 (Suppl. 97, Paper IV): 77-89). This method is well known in the art and adaptable to isolate mononuclear cells from peripheral blood, umbilical cord blood and bone marrow.

"Transduction" refers to the delivery of gene(s) or other polynucleotide sequence, such as a polynucleotide sequence encoding FLT3L or a CAR, to T cells using one or more vectors. In an embodiment, retroviral vectors are transduced into a cell through infection and provirus integration. In certain embodiment, a target cell, e.g., a T cell, is "transduced" if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

In an embodiment, the modified cells of the invention are produced by transducing T cells with a vector encoding a CAR, such as the vector of FIGS. 15 and 16, corresponding with SEQ ID NOs: 2 and 3. The resulting anti-Her2 CAR T cells are then transduced with a retroviral vector in which FLT3L is expressed, such as the vector of FIG. 14, corresponding with SEQ ID NO: 1. Although this "dual-transduction" method requires the sequential transduction of two or more vectors, the present invention also contemplates other methods of dual-transduction including the simultaneous transduction of two or vectors.

In an embodiment, populations of modified T cells that have been transduced with the vector of the invention are expanded under conditions such that the nucleic acid encoded by the vector is expressed.

"Expansion", "expanding", "propagation" and the like refer to the use of cell culture conditions to increase the number of modified T cells prior to administration to the subject. T cells may be expanded using any cell culture method known in the art, for example, T cells may be expanded in tissue culture as liquid culture, monolayers or the like.

The terms "expressible," "expressed," and variations thereof refer to the ability of a cell to transcribe a nucleotide sequence to RNA and optionally translate the mRNA to synthesize a peptide or polypeptide that provides a biological or biochemical function.

The adoptive cellular therapies contemplated by the present invention are not limited to CART cell therapy. The present invention also contemplates the use of a subject's tumour infiltrating lymphocytes (TILs) using a conventional adoptive cellular therapy approach. The skilled person would understand that the culture conditions necessary to expand cell number and facilitate expression of the relevant nucleic acid would be dependent on the type of T cell that has been transduced in accordance with the invention.

In an embodiment, the method comprises:
  a. providing a biological sample comprising T cells from a subject;
  b. isolating T cells from the sample;
  c. transducing the isolated T cells in vitro with one or more vectors of the invention;

d. expanding the modified T cells of step (c) under conditions such that the nucleic acid(s) encoded by the vector(s) is expressed; and e. administering a therapeutically effective amount of the modified T cells to the subject, wherein the method further comprises the administration of one or more immune adjuvants.

In an embodiment, the immune adjuvant is selected from the group consisting of an inhibitor of the PDL-1: PD-1 axis, a TLR3 agonist, a 4-1BB agonist, a TLR7 agonist, an inhibitor of TIM-3, and an inhibitor of CTLA-4.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Unless otherwise defined, all technical and scientific terms used herein have the same meanings as commonly understood by one of ordinary skill in the art to which this invention belongs.

The various embodiments enabled herein are further described by the following non-limiting examples.

Example 1

Anti-Her2 CAR T Cell Model

Primary murine splenocytes were transduced with a CAR containing the CD28 and TCR-ζ signaling domains recognizing the human Her2 antigen (scFv-CD28-ζ) as described in (Mardiana et al. 2017, *Cancer Research*, 77: 1296-1309; John et al. 2013, *Clinical Cancer Research*, 19: 5636-5646; Beavis et al. 2017, supra).

The syngeneic tumour lines 24JK-Her2 (a sarcoma cell line), E0771-Her2 (a triple negative breast cancer line) and MC38-Her2 (a colon carcinoma cell line) were engineered to express the human Her2 receptor. These lines are of C57/BL6 origin, allowing them to be transplanted into C57/BL6 hHer-2 transgenic mice. Using this model, the human Her2 receptor (minus intracellular signaling domains) is expressed under the control of the whey acidic protein promoter, resulting in expression in the cerebellum and breast tissues.

Figure 1:
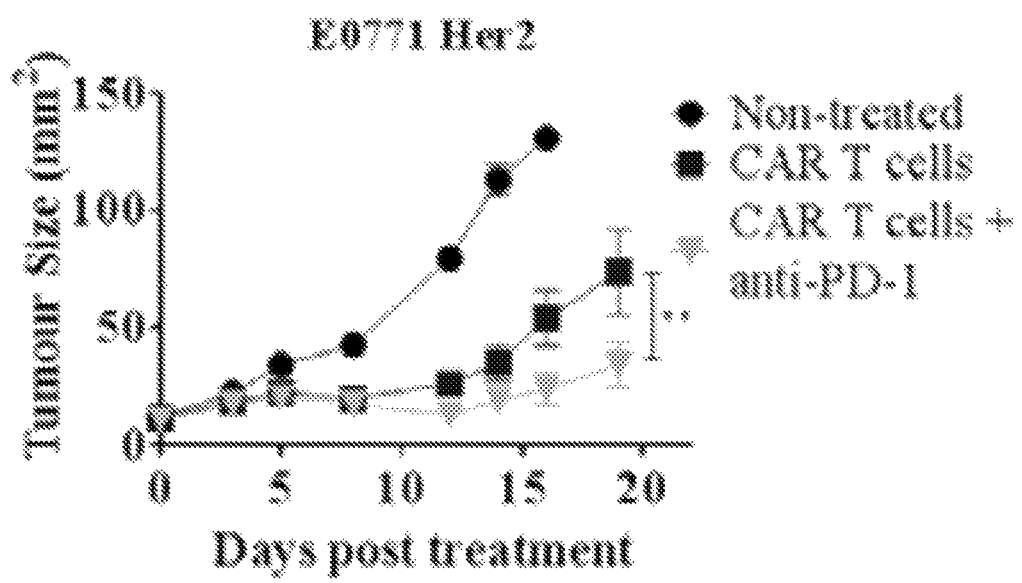
FIG. 1 shows that anti-Her2 CAR T cells mediate anti-tumour effects in vivo. A graphical representation of tumour size ($mm^2$; y-axis) against time (days post treatment; x-axis) in C57/BL6 Her2 transgenic mice bearing established E0771-Her2 tumours following transfer of anti-Her2 CAR T cells after irradiation with 5Gy total body irradiation. Mice were also subject to daily treatment with IL-2 (50000

Anti-Her2 CAR T cells mediate potent anti-tumour efficacy against Her2+ tumour cells in vitro. In vivo treatment of mice bearing Her2+ tumours results in partial responses, but few curative responses even in combination with adjuvant immunotherapies such as anti-PD-1 or 4-1BB (FIG. 1).

Example 2

FLT3L-Generated CD103+ DCs Induce Superior T Cell Expansion In Vitro

T cells were transduced with a retroviral vector in which FLT3L was expressed along with truncated human nerve growth factor receptor (NGFR) as a marker gene to indicate the efficiency of transduction (FIG. 7A). GP+e86 viral-packaging lines were sorted by flow cytometry to generate FLT3L low ($FL^{lo}$), intermediate ($Fl^{int}$) or high ($FL^{high}$) expressing lines. Murine C57BL/6 splenocytes were cultured in IL-2, IL-7 and activated using anti-CD3 and anti-CD28 antibodies before transduction to express NGFR $FL^{lo}$, $Fl^{int}$ or $FL^{high}$. To verify that the transduced cells were expressing FLT3L at low, intermediate and high levels, supernatants were collected at 7 days post-transduction and the presence of FLT3L determined by ELISA (FIGS. 7B and 7C).

To investigate the potential of FLT3L-generated DCs to induce the enhanced proliferation of T cells, bone marrow derived DCs (BMDDCs) were generated in the presence of GMCSF and FLT3L in line with previously published protocols (Mayer et al. 2014, *Blood*, 124: 3081-3091). Supernatant derived from NGFR $FL^{lo}$, $Fl^{int}$ or $FL^{high}$ T cells was able to induce an increased proportion and number of CD11c+ MHCII+ DCs and CD103+ DCs in a dose-dependent manner (FIGS. 7D-7F).

We also examined the ability of DCs generated from either FLT3L-expressing or control CAR T cells to induce T cell proliferation. Naïve CD8+ T cells isolated from OT-I mice (in which all T cells possess a transgenic TCR that recognise the SIINFEKL peptide) were preconditioned with either IL-2 and IL-7, or IL-7 and IL-15 for 5 days. Expression of CD44 and CD62L on preconditioned OT-1 T cells was determined by flow cytometry and compared to naïve OT-I T cells (FIGS. 7G and 7H). $4 \times 10^4$ pre-conditioned OT-I T cells were co-cultured with $2 \times 10^4$ in vitro differentiated OVA257-264 SIINFEKL peptide pulsed GM DCs (no FLT3L supplementation) or FL DCs (with FLT3L supplementation). After 5 days, T cell activation was determined in terms of their fold expansion and cytokine production. DCs generated with FLT3L supplementation exhibited significantly enhanced potential to induce T cell proliferation (FIGS. 7I and 7J).

Example 3

FLT3L Expressing CAR T Cells Induce the Differentiation of CD103+ DCs with Superior Antigen Presentation Function Anti-Her2 CAR T cells were transduced with a retroviral vector in which FLT3L was expressed along with truncated human nerve growth factor receptor (NGFR) as a marker gene to indicate the efficiency of transduction. Dual transduction of murine T cells with the anti-Her2 CAR and the NGFR-FLT3L vector resulted in ~40% NGFR+ cells. To verify that the transduced cells were expressing FLT3L, supernatants were collected at 7 days post transduction. Supernatants derived from NGFR-FLT3L CAR T cells contained high levels (~60000 pg/ml) of FLT3L whereas supernatants from control CAR T cells did not contain detectable levels of FLT3L (FIG. 2A).

To investigate the potential of FLT3L expressing CAR T cells to induce the differentiation of CD103+ DCs, bone marrow derived DCs (BMDDCs) were generated in the presence of GMCSF and FLT3L in line with previously published protocols (Mayer et al. 2014, *Blood*, 124: 3081-3091). Recombinant FLT3L promoted the differentiation of CD103+ dendritic cells (FIG. 2B). Similarly, supernatant derived from NGFR-FLT3L CART cells was able to induce an increased proportion and number of CD103+ DCs (FIG. 2C). By contrast, the supernatant from control NGFR-CAR T cells had no effect (FIG. 2C).

We also examined the ability of DCs generated from either FLT3L-expressing or control CAR T cells to induce de novo T cell responses. Naïve CD8+ T cells isolated from OT-I mice (in which all T cells possess a transgenic TCR that recognise the SIINFEKL peptide) were co-cultured with the respective DCs pulsed with SIINFEKL peptide. After 5 days, T cell activation was determined in terms of their fold expansion and cytokine production. DCs generated in the presence of supernatant from FLT3L CAR T cells exhibited significantly enhanced potential to induce T cell responses in terms of both fold expansion (FIG. 2D) and IFNγ production (FIG. 2E).

Given previous reports have indicated that CD103$^+$ DCs exhibit higher expression of TLR3 (Desch, et al. 2014, *Nature Communications*, 5: 4674; Jelinek et al. 2011, *Journal of Immunology*, 186: 2422-2429), we investigated whether the addition of the TLR3 agonist poly IC could further enhance these effects. The addition of poly IC significantly enhanced the expansion (FIG. 2D) and cytokine production of T cells (FIG. 2E) co-cultured with DCs generated with FLT3L CAR supernatants with a >10 fold increase in IFNγ production relative to control DCs. This data clearly demonstrates that FLT3L-expressing CAR T cells promote the differentiation of CD103$^+$ DCs, which stimulate superior CD8$^+$ T cell responses.

Example 4

FLT3L Enhances Anti-Tumour Immune Responses In Vivo

To characterise the effect of FLT3L on tumour growth in vivo, tumour cells were engineered to express FLT3L using an MSCV-Cherry retroviral vector. This was done as proof of principle, to generate FLT3L within the tumour microenvironment without adoptively transferring FLT3L-expressing T cells. Overexpression of FLT3L by 24JK-Her2 tumours resulted in a significant reduction in tumour growth compared to control tumours with 4/6 FLT3L-expressing tumours being rejected (FIGS. 3A and 6A). This effect was not observed in RAG$^{-/-}$ mice (FIGS. 3B and 6N), indicative of a T cell-dependent mechanism.

Flow cytometry analysis of tumour-infiltrating lymphocytes at day 8 post-tumour injection indicated that T cells isolated from FLT3L expressing tumours were both more abundant and more activated as shown by significantly increased CD69 expression (FIG. 3C). These results indicate that expression of FLT3L in the tumour significantly enhances anti-tumour immune responses, leading us to investigate the therapeutic potential of FLT3L-expressing T cells in the context of ACT.

Example 5

FLT3L Induces Tumour Regression In Vivo

In an additional analysis, human 24JK-Her2 were transduced with FLT3L (FL), Cherry (Cherry FL$^{hi}$) or control vector (Cherry$^{hi}$). 5×10$^5$ cells were subcutaneously injected into the right flank of human Her2 (hHer2$^{+/-}$) transgenic mice and tumour growth was monitored. Mice were euthanised when tumour area exceeds 100 mm$^2$. FLT3L expression resulted in inhibition of tumour growth and enhanced survival (FIGS. 6A and 6B).

Tumours and tumour draining lymph nodes (dLN) were also analysed on day 9 post tumour inoculation by flow cytometry. Increased infiltration of CD8$^+$ T cells and expansion of CD103$^+$ dendritic cells (DCs) were observed in FLT3L-secreting tumours. Increased migratory and resident DCs were detected in the dLN of FLT3L-secreting tumours (FIGS. 6C-6F). Furthermore, the frequency of Cherry+ cells in the tumours and dLN suggests that migratory DCs more efficiency take up and transport tumour antigens in the dLN.

The ability of FLT3L to induce tumour regression was assessed systemically in a bilateral flank tumour model, where mice were inoculated on the right (ipsilateral) flank with either Cherry FL$^{hi}$ or control Cherry$^{hi}$ 24 JK-Her2 cells, as well as the control Cherry$^{hi}$ 24 JK-Her2 cells on the left (contralateral) flank. After injection of ipsilateral Cherry FL$^{hi}$, we observed tumour regression. This effect was not observed following injection of contralateral Cherry$^{hi}$ 24 JK-Her2 cells (FIGS. 6I and 6J). Furthermore, when 247K-Her2 Cherry FL$^{hi}$ cells were titrated at different ratios with Cherry$^{hi}$ control cells and subcutaneously inoculated into the ipsilateral flank of hHer2$^{+/-}$ transgenic mice, reduction in tumour area was observed at 100%, 10% and 1% ratio of Cherry FL$^{hi}$ cells (FIG. 6K). This was despite significantly reduced levels of tumour and serum FLT3L (FIGS. 6L and 6M) at the 10% and 1% ratios of Cherry FL$^{hi}$ cells. This suggests that local concentrations of FLT3L are critical for the therapeutic effect.

Example 6

FLT3L Expression at the Tumour Site Enhances Anti-Tumour Immunity

Her2 transgenic mice were injected sub-cutaneously with 5×10$^5$ 24 JK-Her2 tumour cells, non-lethally irradiated (0.5Gy; to allow CAR T cell engraftment) at day 9 and treated with 1×10$^7$ anti-Her2 CART cells on days 9 and 10. The administration of FLT3L-expressing CAR T cells resulted in a higher concentration of FLT3L in the tumour (FIG. 4A) and a significantly greater therapeutic efficacy (FIG. 4B). Taken together, these results indicate that engineering T cells to express FLT3L can enhance the concentration of FLT3L at the tumour site, engage the host immune system and increase the efficacy of ACT in solid tumours.

Example 7

Investigate the In Vivo Therapeutic Potential of FLT3L-Expressing OT-I T Cells

To test the effects of FLT3L-expressing T cells in a model of conventional ACT, we investigated the efficacy of FLT3L-expressing OT-I T cells adoptively transferred into mice bearing E0771-OVA tumours.

To determine the therapeutic efficacy of FLT3L-expressing OT-I T cells, 2×10$^5$ triple negative breast cancer line E0771 expressing ovalbumin (OVA) (E0771 OVA$^{dim}$) cells were injected into the fourth mammary fat pad of wild-type mice. Once tumours establish (designated day 0) mice were pre-conditioned with non-lethal irradiation (0.5 Gy) to allow T cell engraftment and treated on days 0 and 1 with 1×10$^7$ Cherry (control) or Cherry-FLT3L OT-I T cells. Mice were also intraperitoneally administered with 50,000 U IL-2 to sustain T cell growth (FIG. 8A).

The efficacy of Cherry/Cherry-FLT3L OT-I T cells was also evaluated in combination with poly IC or poly ICLC using the same dose used in Example 3. The therapeutic effect of poly IC or poly ICLC alone was included as a control.

The expression of FLT3L in the blood and sera of mice was also determined by ELISA (FIG. 8B). To investigate the potential of FLT3L-expressing OT-I T cells to induce the expansion of DC precursors (pre-cDC), the proportion of pre-cDC in the bone marrow, tumour and dLN were assessed at day 5 and day 7 post-treatment (FIGS. 8C, 8D and 8I). Significant increases in tumour cDC1, cDC2 and cDC1 precursors was shown (FIG. 8F), while significant increases in total, migratory and resident DCs was also shown in the dLN. Taken together, these results indicate that the adoptive transfer of FLT3L-secreting T cells expands CD130$^+$ cDC1s.

To investigate the broader transcriptional changes that are associated with DC-related genes following treatment with OT-I or OT-1 FLT3L T cells, at day 7 post-treatment, tumours were excised, digested and RNA extracted for analysis using the Nanostring Immune Panel Array. This analysis identified a number of differentially expressed genes (FIGS. 8G and 8H), many of which are expressed by dendritic cells, including cDC1, and is concomitant with the expansion of CD103+ cDC1s after treatment with FLT3 secreting T cells.

E0771-OVA tumour-infiltrating lymphocytes were analysed by flow cytometry following treatment as described in the paragraph above. The number of IL-12- and TNFα-expressing cDC1s and cDC2s at the tumour site was significantly increased by day 7 post-treatment with FLT3L-expressing OT-I T cells (FIG. 9B). Furthermore, corresponding significant increases in endogenous CD8+ T cells expressing IFNγ and TNFα were also observed (FIGS. 9F-9H). These results indicate that DC expansion enhances infiltration of functional host CD8+ T cells at the tumour site.

FLT3L-secreting OT-I T cells significantly increased the proportion of endogenous CD8+ T cells with a CD62L+ TCF7+ phenotype (FIG. 9G). This phenotype has previously been associated with improved responses to immune checkpoint blockade (Sade-Feldman et al., 2018, *Cell*, 175(4): 998-1013) and suggests that this may enhance responses to immune adjuvants such as anti-PD-1 or anti-CTLA-4.

The transcriptional changes associated with T cells and NK cell related genes were also interrogated using the methods described in the paragraph above. This analysis identified a number of differentially expressed genes (FIG. 9K), which may be responsible for the enhanced infiltration of functional host (i.e., endogenous) CD8+ T cells at the tumour site.

To further investigate the in vivo therapeutic effects of combining FLT3L expressing T cells combined with pIC or agonistic anti-41BB antibody using the OT-I model in wild-type, Batf3-/- or Rag1-/- mice inoculated with E0771-OVA cells and treated with transduced OT-I T cells (as per FIG. 8A). Mice were dosed intraperitoneally with pIC (100 μg/mouse) and anti-41BB (100 μg/mouse) at days 5 and 8 post-treatment. Mice were euthanised when tumour area exceeded 150 mm². In wild-type mice, FLT3L expression resulted in inhibition of tumour growth and enhanced survival, while the combination of FL secreting OT-I T cells with pIC and antib-41BB significantly inhibits tumour growth (FIG. 10A). The anti-tumour activity observed in the wild-type mice was diminished in Batf3$^{-/-}$ and Rag1$^{-/-}$ mice, which respectively lack cDC1 DCs and T cells (FIGS. 10B and 10C).

The inhibition of tumour growth observed using the combination of FLT3L-secreting T cells, together with immune stimulatory adjuvants may be associated with differentially expressed genes related to immune cell activation after adjuvant therapy (FIG. 10D). Alternatively, this effect may also be associated with the enhanced activation of cDC1s and/or frequency of tumour antigen-specific T cells within the tumours or dLN (FIGS. 10E-10J).

Despite the significant inhibition of tumour growth observed FLT3L-secreting T cells in combination with immune adjuvants, no significant toxicity was observed (FIG. 13).

Example 8

Investigate the Efficacy of FLT3L-Expressing Anti-Her2 CAR T Cells

C57/BL6 Her2 transgenic mice (hHer2$^{-/-}$) were used as recipients and CAR T cells were generated from WT mice as previously described (John et al., supra; Beavis, et al. 2017, supra; FIG. 11A). Mice were subcutaneously inoculated with 2.5×10⁵ of the Her2 expressing colorectal cancer cell line MC38. At day 5 post-tumour inoculation, mice were treated with 1×10⁷ CAR T or CAR T FL cells following total body irradiation (0.5 Gy) to pre-condition the mice. The mice were also treated with five doses of IL-2 (50,000 units per dose) to sustain T cell growth. Mice were euthanised when tumour area exceeded 150 mm². FTL3L expression by anti-Her2 CART cells was confirmed in vitro (FIG. 11A) and resulted in inhibition of tumour growth and enhanced survival (FIGS. 11C and 11D). The combination of FL secreting CAR T cells and pIC (100 μg per dose on days 5 and 8 post-treatment) significantly inhibited tumour growth and enhanced overall survival (FIGS. 11C and 11D). This effect was not observed in mice lacking functional cDC1 dendritic cells (FIG. 11E) or T cells (FIG. 11F).as CAR T cells do not use DCs to recognise their cognate antigen. Therefore, any effects observed in this system will likely be attributable to epitope spreading and the induction of de novo anti-tumour immune responses.

The effect of epitope spreading was further assessed in hHer2$^{-/-}$ mice subcutaneously inoculated with MC38-Her2 cells on the right flank, followed by treatment with CAR T FL and pIC, as described in FIG. 11A. Mice that were cured of their primary MC38-Her2 tumours were subsequently re-challenged with the parental MC38 line on the left (opposite) flank at day 60 post-treatment (FIG. 12A). Mice that were cured of their primary MC38-Her2 tumours exhibited enhanced tumour growth inhibition during MC38 re-challenge in comparison to naïve mice (FIG. 12B).

To evaluate TCR diversity, CD45.1 host congenic mice were inoculated with E0771-OVA tumours as described in FIG. 10A and adoptively transferred with CD45.2+OT-I T cells with adjuvants. At day 7 post-treatment, tumour dLN were assessed using a panel of 14 TCR Vβ antibodies to evaluate TCR diversity of CD45.1+ host CD8+ T cells. Increased frequency of three TCR Vβ subsets in mice treated with a combination of FLT3L secreting T cells and adjuvants was shown, indicating oligoclonal expansion of host CD8+ T cells (FIGS. 12C and 12D).

Finally, we also assessed anti-OVA responses to determine anti-tumour activity against antigens not targeted by the CAR. hHer2$^{-/-}$ mice were inoculated with 4×10⁵ E0771 cells expressing OVA and Her2 (E0771 OVA Her2 cells) in the fourth mammary fat pad. At day 9 post-tumour inoculation, mice were treated with 1×10⁷ CAR T or CAR T FL cells following total body irradiation (0.5 Gy) to pre-condition the mice. IL-2 (50,000 units per dose) was intraperitoneally administered on days 0 and 2 post-treatment. In addition, mice were also intraperitoneally administered pIC (100 μg) and anti-4-1BB antibody (100 μg) on days 5 and 8 post-treatment. Mice were euthanised when tumour area exceeded 150 mm².

CAR T FL cells in combination with the immune adjuvants significantly enhances tumour growth inhibition (FIG. 12H). This effect is associated with epitope spreading, as indicated by the increased frequency of H-2 K$^b$ OVA Tetramer positive T cells in the blood (FIG. 12F-G).

The invention claimed is:

1. An isolated T cell modified to express and secrete exogenous FMS-like tyrosine kinase 3 ligand (FLT3L), wherein the exogenous FLT3L is a biologically active form of FLT3L.

2. The isolated T cell of claim 1, wherein the isolated T cell is also modified to express a chimeric antigen receptor (CAR), wherein the CAR comprises an antigen binding domain and at least one signaling domain.

3. The isolated T cell of claim 2, wherein the antigen binding domain binds to an antigen selected from the group consisting of CD19, CD20, CD22, CD30, ROR1, CD123, CD33, CD133, CD138, GD2, Her2, Her1, mesothelin, MUC1, gp100, MART-1, MAGE-A3, MUC16, NY-ESO-1, L1-CAM, CEA, FAP, VEGFR2, WT1, TAG-72, CD171, α-FR, CAIX, PSMA, and Lewis Y.

4. The isolated T cell of claim 2, wherein the signaling domain is selected from the group consisting of CD3ζ, CD28, 41BB, DAP10, OX40, ICOS, DAP12, KIR2DS2, 4-1BB, CD3s, CD35, CD3C, CD25, CD27, CD79A, DC79B, CARD11, FcRa, Fcftp, FcRy, Fyn, HVEM, Lck, LAG3, LAT, LRP, NKG2D, NOTCH1, NOTCH2, NOTCH3, NOTCH4, ROR2, Ryk, SLAMF1, Slip76, pTa, TCRa, TCRP, TRIM, Zap70, PTCH2, and LIGHT.

5. The isolated T cell of claim 4, wherein the CAR comprises the CD28 and CD32 signaling domains.

6. A pharmaceutical composition comprising an isolated T cell of claim 1.

7. A method for treating cancer comprising administering a therapeutically effective amount of an isolated T cell of claim 1 to a subject in need thereof.

8. The method of claim 7, further comprising the administration of one or more from the group consisting of an inhibitor of the PDL-1: PD-1 axis, a TLR3 agonist, a 4-1BB agonist, a TLR7 agonist, an inhibitor of TIM-3, and an inhibitor of CTLA-4.

9. The method of claim 7 wherein the cancer is a solid cancer.

* * * * *